(12) United States Patent
Schlingensiepen et al.

(10) Patent No.: US 7,563,778 B2
(45) Date of Patent: Jul. 21, 2009

(54) ANTISENSE OLIGONUCLEOTIDE PREPARATION METHOD

(75) Inventors: Karl-Hermann Schlingensiepen, Göttingen (DE); Wolfgang Brysch, Göttingen (DE)

(73) Assignee: Biognostik Ges. fur biomolekulare Diagnostik mbH, Gottingen (DE)

( * ) Notice: Subject to any disclaimer, the term of this patent is extended or adjusted under 35 U.S.C. 154(b) by 462 days.

(21) Appl. No.: 10/984,919

(22) Filed: Nov. 10, 2004

(65) Prior Publication Data

US 2005/0130927 A1    Jun. 16, 2005

Related U.S. Application Data

(62) Division of application No. 09/341,700, filed as application No. PCT/EP98/00497 on Jan. 30, 1998, now Pat. No. 6,972,171.

(30) Foreign Application Priority Data

Jan. 31, 1997   (EP)   ................................. 97101531

(51) Int. Cl.
*A01N 43/04* (2006.01)
*C11Q 1/68* (2006.01)
*C12P 19/34* (2006.01)
*C07H 21/02* (2006.01)
*C07H 21/04* (2006.01)

(52) U.S. Cl. ............................ 514/44; 435/6; 435/91.1; 435/91.31; 435/375; 435/455; 536/23.1; 536/24.5

(58) Field of Classification Search .................... 435/6, 435/91.1, 91.31, 455, 458, 375; 514/44; 536/23.1, 24.5
See application file for complete search history.

(56) References Cited

U.S. PATENT DOCUMENTS 5,221,620 A * 6/1993 Purchio et al. ............... 435/360
5,801,154 A * 9/1998 Baracchini et al. ........... 514/44
5,948,888 A * 9/1999 de la Monte et al. ......... 530/350

FOREIGN PATENT DOCUMENTS

| WO | WO90/10030 | 9/1990 |
|---|---|---|
| WO | WO93/07883 | 4/1993 |
| WO | WO94/25588 | 11/1994 |
| WO | WO95/00103 | 1/1995 |
| WO | WO95/02422 | 1/1995 |
| WO | WO96/31600 | 10/1996 |
| WO | WO96/39415 | 12/1996 |

OTHER PUBLICATIONS

Reed, J.C. et al., Proc. Natl. Acad. Sci., vol. 87, pp. 3660-3664 (1990).*
Stull et al. Nucleic Acids Res. (1992) vol. 20, No. 13: 3501-3508.*
Probst et al. Trends in Gen. (1996) vol. 12, No. 8: 290-291.*
Stanley T. Crooke, Therapeutic Applications of Oligonucleotides, Annu. Rev. Pharmacol. Toxicol. 1992. 32. pp. 329-376.*
Toon F.C.M. Smetsers et al., Sense and Nucleic Acid Drug Development, 6: pp. 63-67.*
James, W. Antiviral Chem. and Chemotherapy, vol. 2, No. 4, pp. 191-214.*
Milner et al. Nature Biotech., vol. 15, pp. 537-541.*
Ehrlich et al. Antisense Res. and Dev., vol. 4, pp. 173-183.*
Vaerman et al. Blood, vol. 90, No. 1, pp. 331-339.*
Branch, A. Trends in Biochem. Sci., vol. 23, pp. 45-50.*
Crooke, S.T. Antisense Res. and Application, Chapter 1, pp. 1-50, Published by Springer-Verlag.*
Verma et al. Nature, vol. 389, pp. 239-243.*
Crystal, R.G. Science, vol. 270, pp. 404-410.*
Friedmann, T. Scientific American, June Volume, pp. 96-101.*
Yu et al., "Hybrid Oligonucleotides: Synthesis, Biophysical Properties, Stability Studies, and Biological Activity," *Bioorganic & Medicinal Chemistry*, 4(10):1685-1692 (1996).
Zhao et al., "Effect of Different Chemically Modified Oligodeoxynucleotides on Immune Stimulation," *Biochemical Pharmacology*, 51(2):173-182 (1996).
Hatzfeld, "Release of Early Human Hematopoietic Progenitors from Quiescence by Antisense Transforming Growth Factor β1 or or Rb Oligonucleotides," *Journal of Experimental Medicine*, 174(4):925-929 (1991).
Fitzpatrick, et al., "Antisense Oligonucleotides Specific for Transforming Growth Factor β2 Inhibit the Growth of Malignant Mesothelioma Both in Vitro and in Vivo," *Cancer Research*, 57:3200-3207 (1997).

(Continued)

*Primary Examiner*—Jane Zara
(74) *Attorney, Agent, or Firm*—Jacobson Holman PLLC

(57) ABSTRACT

A method for the preparation of an antisense oligonucleotide or derivative thereof comprising the steps of: selecting a target nucleic acid, if necessary elucidating its sequence; generating the antisense oligonucleotide with the proviso that: the oligonucleotide comprises at least 8 residues; the oligonucleotide comprises at maximum twelve elements, which are capable of forming three hydrogen bonds each to cytosine bases; the oligonucleotide does not contain four or more consecutive elements, capable of forming three hydrogen bonds each with four consecutive cytosine bases (CCCC) within the target molecule or alternatively four or more consecutive elements of GGGG; the oligonucleotide does also not contain 2 or more series of three consecutive elements, capable of forming three hydrogen bonds each with three consecutive cytosine bases (CCC) within the target molecule, or alternatively 2 or more series of three consecutive elements of GGG; and the ratio between residues forming two hydrogen bonds per residue (2H-bond-R) with the target molecule and those residues forming three hydrogen bonds per residue (3H-bond-R) with the target molecule, is ruled by the following specifications: 3H-bond-R/3H-bond-R+2H-bond-R≧0.29; and synthesizing the oligonucleotide thus generated in a per se known manner.

5 Claims, 36 Drawing Sheets

OTHER PUBLICATIONS

Pisetsky et al., "Stimulation of in vitro proliferation of murine lymphocytes by synthetic oligonucleotides," *Molecular Biology Reports*, 18(3):217-221 (1993).

Jachimczak et al., "Transforming growth factor β-mediated autocrine growth regulation of gliomas as detected with phosphorothioate antisense oligonucleotides," *International Journal of Cancer*, 65(3): 332-337 (1996).

Jachimczak et al., "The effect of transforming growth factor $\beta_2$-specific phosphorothioate-anti-sense oligonucleotides in reversing cellular immunosuppression in malignant glioma," 78:944-951 (1993).

Agrawal, "Antisense oligonucleotides: towards clinical trials," *Trends in Biotechnology*, 14(10):376-387 (1996).

* cited by examiner

Adenine

Guanine

Cytosine

Thymine

Adenine

Guanine

Cytosine

Uracil

FIG. 3-1

| | | |
|---|---|---|
| 1. | A3 | CCCGGAGGGCGGCATGGGGGA |
| 2. | N1 | CCTCAGGGAGAAGGGCGC |
| 3. | N2 | GTAGGAGGGCCTCGAGGG |
| 4. | N3 | CTGCAGGGGCTGGGGGTC |
| 5. | N4 | AGGGCTGGTTGTGGTGGGG |
| 6. | N5 | GGCATGGGGGAGGCGGCG |
| 7. | N6 | CCGGAGGGCGGCATGGGG |
| 8. | N7 | GGGGGGCTGGCGAGCCGC |
| 9. | N8 | GGACAGGATCTGGCCGCGGATGG |
| 10. | N9 | CCCCCTGGCTCGGGGGGC |
| 11. | N10 | GGGCCGGGCGGCACCTCC |
| 12. | N11 | GGGCAGCGGGCCGGGCGG |
| 13. | N12 | ACGGCCTCGGGCAGCGGG |
| 14. | N13 | GGGTGCTGTTGTACAGGG |
| 15. | N14 | GGGTTTCCACCATTAGCACGCGGG |
| 16. | N15 | TCATAGATTTCGTT |
| 17. | N16 | TTGTCATAGATTT |
| 18. | N17 | AAGAACATATATATG |
| 19. | N18 | AAGAACATATATAT |
| 20. | N19 | TTGAAGAACATATATA |
| 21. | N20 | CCGGGAGAGCAACACGGG |
| 22. | N21 | ACTTTTAACTTGA |
| 23. | N22 | ATTGTTGCTGTATTT |
| 24. | N23 | ATTGTTGCTGTATT |
| 25. | N24 | AATTGTTGCTGTATT |
| 26. | N25 | AATTGTTGCTGTAT |
| 27. | N26 | GGCGAGTCGCTGGGTGCCAGCAGCCGG |
| 28. | N27 | GGCGAGTCGCTGGG |
| 29. | N28 | ACATCAAAAGATAA |
| 30. | N29 | TGACATCAAAAGAT |
| 31. | N30 | GGGCCCTCTCCAGCGGGG |
| 32. | N31 | GGGCTCGGCGGTGCCGGG |
| 33. | N32 | GGGGCAGGGCCCCGAGGCA |
| 34. | N33 | GGCTCCAAATGTAGGGGC |
| 35. | N34 | CGGGTTATGCTGGTTGTACAGGGC |
| 36. | N35 | CGGCGCCGCCGAGGCGCCCGGG |
| 37. | N36 | GGGGCGGGGCGGGACC |
| 38. | N37 | GGGCGGGGCGGGGCGGGG |
| 39. | N38 | GGGCGGGGTGGGGCCGGG |
| 40. | N39 | GGCAAGGCAGCGGGGGCGGGG |
| 41. | TGF-β1-1 | CGGTAGCAGCAGCG |
| 42. | TGF-β1-2 | CCAGTAGCCACAGC |
| 43. | TGF-β1-3 | GCAGGTGGATAGTCC |
| 44. | TGF-β1-4 | CTTGCAGGTGGATAG |
| 45. | TGF-β1-5 | CGATAGTCTTGCAGG |
| 46. | TGF-β1-6 | CCATGTCGATAGTCTTGC |
| 47. | TGF-β1-7 | CTCGATGCGCTTCCG |
| 48. | TGF-β1-8 | CCTCGATGCGCTTCC |
| 49. | TGF-β1-9 | GGATGGCCTCGATGC |
| 50. | TGF-β1-10 | GGACAGGATCTGGCC |
| 51. | TGF-β1-11 | CGCAGCTTGGACAGG |
| 52. | TGF-β1-12 | GAGCCGCAGCTTGG |
| 53. | TGF-β1-13 | CGAGCCGCAGCTTG |
| 54. | TGF-β1-14 | ACCTCCCCCTGGCT |
| 55. | TGF-β1-15 | CCACCATTAGCACG |
| 56. | TGF-β1-16 | GAACTTGTCATAGATTTC |
| 57. | TGF-β1-17 | GCTGTGTGTACTCTGC |
| 58. | TGF-β1-18 | GCTCCACGTGCTGC |
| 59. | TGF-β1-19 | GAATTGTTGCTGTATTTC |
| 60. | TGF-β1-20 | GCCAGGAATTGTTGC |
| 61. | TGF-β1-21 | GTGACATCAAAAGATAAC |
| 62. | TGF-β1-22 | GGCTCAACCTGCC |
| 63. | TGF-β1-23 | GCTGTCACAGGAGC |
| 64. | TGF-β1-24 | CCTGCTGTCACAGG |
| 65. | TGF-β1-25 | GCAGTGTGTTATCCCTGC |
| 66. | TGF-β1-26 | GCAGTGTGTTATCCC |

FIG. 3-2

| | | |
|---|---|---|
| 67. | TGF-β1-27 | CCAGGTCACCTCGG |
| 68. | TGF-β1-28 | GCCATGAATGGTGGC |
| 69. | TGF-β1-29 | GCCATGAATGGTGG |
| 70. | TGF-β1-30 | CCATGAGAAGCAGG |
| 71. | TGF-β1-31 | GGAAGTCAATGTACAGC |
| 72. | TGF-β1-32 | CCACGTAGTACACGATGG |
| 73. | TGF-β1-33 | GCACTTGCAGGAGC |
| 74. | p53-1 | CCATGGCAGTGACC |
| 75. | p53-2 | GGCTCCTCCATGGC |
| 76. | p53-3 | GCTAGGATCTGACTGC |
| 77. | p53-4 | CCTGACTCAGAGGG |
| 78. | p53-5 | GGTCTGAAAATGTTTCC |
| 79. | p53-6 | CCATTGCTTGGGACGG |
| 80. | p53-7 | GCATCAAATCATCC |
| 81. | p53-8 | CCATTGTTCAATATCG |
| 82. | p53-9 | GGTCTTCAGTGAACC |
| 83. | p53-10 | GGAGCTTCATCTGGACC |
| 84. | p53-11 | CCTCTGGCATTCTGG |
| 85. | p53-12 | AGGGACAGAGATG |
| 86. | p53-13 | GTTTTCTGGGAAGG |
| 87. | p53-14 | GGTTTTCTGGGAAG |
| 88. | p53-15 | AGGTTTTCTGGGAAG |
| 89. | p53-16 | GTAGGTTTTCTGGG |
| 90. | p53-17 | GGTAGGTTTTCTGG |
| 91. | p53-18 | CCAGAATGCAAGAAGCC |
| 92. | p53-19 | GCTGTCCCAGAATGC |
| 93. | p53-20 | GCAAGTCACAGACTTGGC |
| 94. | p53-21 | CCACAGCTGCACAGG |
| 95. | p53-22 | GGTGTGGAATCAACC |
| 96. | p53-23 | GTCATGTGCTGTGA |
| 97. | p53-24 | CGCTATCTGAGCAGCG |
| 98. | p53-25 | CCAGTGTGATGATGG |
| 99. | p53-26 | CCAGTAGATTACCACTGG |
| 100. | p53-27 | GGCACAAACACGCACC |
| 101. | p53-28 | CCACGGATCTGAAGG |
| 102. | p53-29 | CGGAACATCTCGAAGCG |
| 103. | p53-30 | CCTCATTCAGCTCTCGG |
| 104. | p53-31 | CCTTGAGTTCCAAGG |
| 105. | p53-32 | CCTTTTTGGACTTCAGG |
| 106. | p53-33 | GGAGGTAGACTGACCC |
| 107. | p52-N-1 | AAAATGTTTCCT |
| 108. | p52-N-2 | TGAAAATGTTTC |
| 109. | p52-N-3 | CTGAAAATGTTT |
| 110. | p52-N-4 | TCTGAAAATGTTT |
| 111. | p52-N-5 | TCTGAAAATGTT |
| 112. | p52-N-6 | AAATCATCCATT |
| 113. | p52-N-7 | TTGTTCAATATC |
| 114. | p52-N-8 | ATTGTTCAATATC |
| 115. | p52-N-9 | ATTGTTCAATAT |
| 116. | p52-N-10 | CATTGTTCAATAT |
| 117. | p52-N-11 | CATTGTTCAATA |
| 118. | p52-N-12 | AAAAGTGTTTCT |
| 119. | p52-N-13 | ACATGATTTTTTAT |
| 120. | p52-N-14 | AACATGAGTTTTTTAT |
| 121. | p52-N-15 | ACATGAGTTTTTTA |
| 122. | p52-N-16 | AACATGAGTTTTTTA |
| 123. | p52-N-17 | AACATGAGTTTTTT |
| 124. | p52-N-18 | AAAACATCTTGTT |
| 125. | p53-T-1 | CAGAGGGGGCTCGACGC |
| 126. | p53-T-2 | CTGACTCAGAGGGGGCTC |
| 127. | p53-T-3 | AGGGGGACAGAACG |
| 128. | p53-T-4 | TTGGGACGGCAAGGGGGACAGAA |
| 129. | p53-T-5 | TGGGACGGCAAGGGGA |

FIG. 3-3

| | | |
|---|---|---|
| 130. | p53-T-6 | GCCACGGGGGGAGCA |
| 131. | p53-T-7 | GCAGGGGCCACGGGGGGAG |
| 132. | p53-T-8 | AGGGGCCACGGGGG |
| 133. | p53-T-9 | CAGGGGCCACGGGG |
| 134. | p53-T-10 | GGTGCAGGGGCCACG |
| 135. | p53-T-11 | TGGTGCAGGGGCCGCCGG |
| 136. | p53-T-12 | GGGGCTGGTGCAGGGGCC |
| 137. | p53-T-13 | AGGGGGCTGGTGCAGGGG |
| 138. | p53-T-14 | GGGCTGGTGCAGGG |
| 139. | p53-T-15 | GAGGGGGCTGGTGCAG |
| 140. | p53-T-16 | AGGAGGGGGCTGGTG |
| 141. | p53-T-17 | GGGCCAGGAGGGGCTGG |
| 142. | p53-T-18 | AGGGGCCAGGAGGGGGCT |
| 143. | p53-T-19 | GGGGCCAGGAGGGG |
| 144. | p53-T-20 | CAGGGGCCAGGAGGG |
| 145. | p53-T-21 | TCTGGGAAGGGACAGA |
| 146. | p53-T-22 | TGAGGGCAGGGGAGTA |
| 147. | p53-T-23 | TTGAGGGCAGGGGAG |
| 148. | p53-T-24 | CGGGTGCCGGGCGGGGGTG |
| 149. | p53-T-25 | CGGACGCGGGTGCCGGGCGGGGGT |
| 150. | p53-T-26 | CGGGTGCCGGGCGGG |
| 151. | p53-T-27 | GGACGCGGGTGCCGGGCG |
| 152. | p53-T-28 | TGGGGGCAGCGCCTCACA |
| 153. | p53-T-29 | GGTGGGGGCAGCGCCT |
| 154. | JunB-1 | CCATTTTAGTGCACATCCGG |
| 155. | JunB-2 | CCATTTTAGTGCACATCC |
| 156. | JunB-3 | GCTGTTCCATTTTAGTGC |
| 157. | JunB-4 | GTAGTCGTGTAGAG |
| 158. | JunB-5 | GTTTGTAGTCGTGTAG |
| 159. | JunB-6 | GTTTCAGGAGTTTGTAG |
| 160. | JunB-7 | CCAGCTCCGAAGAGG |
| 161. | JunB-8 | CGTCGTCGTGATCACG |
| 162. | JunB-9 | GGTAAAAGTACTGTTCC |
| 163. | JunB-10 | GGCTTTGACAAAGCC |
| 164. | JunB-11 | CTTGTGCAGATCGTCCAG |
| 165. | JunB-12 | CGTGGTTCATCTTGTGC |
| 166. | JunB-13 | CACGTGGTTCATCTTGTG |
| 167. | JunB-14 | CCTCCTTGAAGGTGG |
| 168. | JunB-15 | CGCTCCACTTTGATGCG |
| 169. | JunB-16 | CCTTGTCCTCCAGG |
| 170. | JunB-17 | GGTACTCGACAGCC |
| 171. | JunB-18 | CTGACGTGGGTCATG |
| 172. | JunB-19 | CCGTTGCTGACGTGG |
| 173. | JunD-1 | CATCCTCCGCCTCC |
| 174. | JunD-2 | GTTTCCATCCTCCG |
| 175. | JunD-3 | GGTGTTTCCATCCTCC |
| 176. | JunD-4 | GGTGTTTCCATCCTC |
| 177. | JunD-5 | GCTCAGCGCCTCATC |
| 178. | JunD-6 | CCTTCTTCATCATGCTGC |
| 179. | JunD-7 | CCTTCTTCATCATGCT |
| 180. | JunD-8 | CCTTCTTCATCATGC |
| 181. | JunD-9 | GCGTCCTTCTTCATCATGC |
| 182. | JunD-10 | CCTGCTCACTCAGG |
| 183. | JunD-11 | CGCAGGCTTGAGCG |
| 184. | JunD-12 | GCCAGCTTCAGCAGC |
| 185. | JunD-13 | GGTGGTGACCAGCC |
| 186. | JunD-14 | CCTCGGCGAACTCC |
| 187. | JunD-15 | GCTTGTGTAAATCC |
| 188. | JunD-16 | GGTTCTGCTTGTGTAAATCC |
| 189. | JunD-17 | GCTGCTCAGGTTCGC |
| 190. | JunD-18 | GAAGGCGACCGTCG |
| 191. | JunD-19 | CGAAGGCGACCGTC |
| 192. | JunD-20 | GCACCGTCTCTGTGGC |
| 193. | JunD-21 | CGTGTCCATGTCGATGG |
| 194. | JunD-22 | CGTGTCCATGTCGATG |

FIG. 3-4

| | | |
|---|---|---|
| 195. | JunD-23 | GCGTGTCCATGTCG |
| 196. | JunD-24 | CCAGCTTGCGCTTGC |
| 197. | JunD-25 | CGCTCCAGCTTGCG |
| 198. | JunD-26 | CGTGTTCTGACTCTTGAG |
| 199. | JunD-27 | CGTGTTCTGACTCTTG |
| 200. | JunD-28 | GCTGTTGACGTGGC |
| 201. | JunD-29 | CGACTCAGTACGCC |
| 202. | JunD-30 | GCCATGCCCGACTC |
| 203. | JunD-31 | CCCTTGGAGGTGGC |
| 204. | JunB-N-1 | TTTTAGTGCACAT |
| 205. | JunB-N-2 | TGTTCCATTTTAGT |
| 206. | JunB-N-3 | AAAAAAAGTGGAAG |
| 207. | JunB-N-4 | TACAAAAAAAAGTG |
| 208. | JunB-N-5 | ATACAAAAAAAAGT |
| 209. | JunB-N-6 | CATACAAAAAAAGT |
| 210. | JunB-N-7 | CATACAAAAAAAAG |
| 211. | JunB-N-8 | GAAAAAAAACATAC |
| 212. | JunB-N-9 | CAGAAAAAAAAACATAC |
| 213. | JunB-N-10 | CAGAAAAAAAAACAT |
| 214. | JunB-N-11 | TTCAATATGAATCG |
| 215. | JunB-N-12 | TATTCAATATGAATCG |
| 216. | JunB-N-13 | TATTCAATATGAATC |
| 217. | JunB-N-14 | TATTCAATATGAAT |
| 218. | JunB-N-15 | TATATTCAATATGAA |
| 219. | JunB-N-16 | TTATATTCAATATGA |
| 220. | JunB-N-17 | TATTATATTCAATATGA |
| 221. | JunB-N-18 | TTATATTCAATATG |
| 222. | JunB-N-19 | TATTATATTCAATATG |
| 223. | JunB-N-20 | ATTATATTCAATAT |
| 224. | JunB-N-21 | TATTATATTCAATAT |
| 225. | JunB-N-22 | ATATATTATATTCAATAT |
| 226. | JunB-N-23 | AAATATATTTATATTCAATAT |
| 227. | JunB-N-24 | TATTATATTCAATA |
| 228. | JunB-N-25 | ATATATTATATTCAATA |
| 229. | JunB-N-26 | CAAATATATTATATTCAATA |
| 230. | JunB-N-27 | TATATTATATTCAAT |
| 231. | JunB-N-28 | AATATATTATATTCAAT |
| 232. | JunB-N-29 | TATATTATATTCAA |
| 233. | JunB-N-30 | CAAATATATTATATTCAA |
| 234. | JunB-N-31 | CAAATATATTATATTCA |
| 235. | JunB-N-32 | CAAATATATTATATTC |
| 236. | JunB-N-33 | CACAAATATATTATATTC |
| 237. | JunB-N-34 | AAATATATTATATT |
| 238. | JunB-N-35 | CAAATATATTATATT |
| 239. | JunB-N-36 | CAAATATATTATAT |
| 240. | JunB-N-37 | CACAAATATATTATAT |
| 241. | JunB-N-38 | CACAAATATATTAT |
| 242. | JunB-N-39 | TACACAAATATATTAT |
| 243. | JunB-N-40 | TACACAAATATATTA |
| 244. | JunB-N-41 | TAAATACACAAATATATT |
| 245. | JunB-N-42 | AATACACAAATATA |
| 246. | JunB-N-43 | GTTAAATACACAAATA |
| 247. | JunB-N-44 | TGTTAAATACACAA |
| 248. | JunB-N-45 | TTTAGAGACTAAGT |
| 249. | JunB-N-46 | ATAAACTCTTTAGA |
| 250. | JunB-N-47 | TAAAATAAACTCTTTAG |
| 251. | JunB-N-48 | TAAAATAAACTCTTTA |
| 252. | JunB-N-49 | TTAAAATAAACTCTTT |
| 253. | JunB-N-50 | CTTAAAATAAACTC |
| 254. | JunB-N-51 | TAAAAAGAACAAACA |
| 255. | JunB-N-52 | TAAAAAAGAACAAAC |
| 256. | JunB-N-53 | CAATAAAAAGAACAA |
| 257. | JunB-N-54 | TCAATAAAAAGAACAA |
| 258. | JunB-N-55 | TCAATAAAAAGAAC |
| 259. | JunB-N-56 | TTCAATAAAAAGAA |
| 260. | JunB-N-57 | TAGATTCAATAAAAAGA |

FIG. 3-5

| # | Name | Sequence |
|---|---|---|
| 261. | JunB-T-1 | TGGCGCGGGCGGGTAGC |
| 262. | JunB-T-2 | GGGCTGGCGGCGGGCGGGTAG |
| 263. | JunB-T-3 | TCGGGGGCTGGCGCGGGCGGG |
| 264. | JunB-T-4 | TGGGTGCCTGGTCGCGCGTTCTCGGG |
| 265. | JunB-T-5 | AGGGTCCCTGCGGGGCCG |
| 266. | JunB-T-6 | GGGAGGGTCCCTGCGGGG |
| 267. | JunB-T-7 | GGGAGGGTCCCTGCGG |
| 268. | JunB-T-8 | TGGGCCGGGTCCGC |
| 269. | JunB-T-9 | TCCCGGGGGTGTAG |
| 270. | JunB-T-10 | AGTACTGTCCCGGGGGTGT |
| 271. | JunB-T-11 | GGGACACGTTGGGGGGTG |
| 272. | JunB-T-12 | GCCGGGGCCCCCGGTAGC |
| 273. | JunB-T-13 | CGGGCCCAGCCGGGGGC |
| 274. | JunB-T-14 | CGGGCCCAGCCGGG |
| 275. | JunB-T-15 | GGGAGGTGGCTCCGGGCCGG |
| 276. | JunB-T-16 | AGGGCGGCCGCGTGTGGA |
| 277. | JunB-T-17 | GGGTGGCCACCGGCGAAGGG |
| 278. | JunB-T-18 | AGGGGCAGGGGACGT |
| 279. | JunB-T-19 | TAAAGGGGCAGGGGACGT |
| 280. | JunB-T-20 | AGGGGGTGTCCGTAAAGGGG |
| 281. | JunD-T-1 | GGGGACGCGAACGTGCCGCCG |
| 282. | JunD-T-2 | CGGGGAACAAGCGGCCCGGG |
| 283. | JunD-T-3 | GGCCGTCGGGGGCG |
| 284. | JunD-T-4 | GCGGCCGTCGGGGGC |
| 285. | JunD-T-5 | AGGGGGGTAGGAGGCGGG |
| 286. | JunD-T-6 | GCGCTGGGGGCGCC |
| 287. | JunD-T-7 | GGCCGTCGGGGGGT |
| 288. | JunD-T-8 | GGGGAGGCCAGCTTC |
| 289. | JunD-T-9 | GGCCGCCACCTTGGGG |
| 290. | JunD-T-10 | GCGGCCGCCGCCGGGG |
| 291. | JunD-T-11 | GGGCGCGGCCGCCGCCGGGG |
| 292. | JunD-T-12 | GGGGTGGCGGCGGCGG |
| 293. | JunD-T-13 | GGGGGTGGCGGCGGCC |
| 294. | JunD-T-14 | TGGGGCAGCAGCTGGCAG |
| 295. | JunD-T-15 | CGGGGCGCCCACGACACC |
| 296. | JunD-T-16 | CGGGGCGCCCACGACAC |
| 297. | JunD-T-17 | GGGCCGCACCCTCTCCAAGTCCGGGG |
| 298. | ErbB-2-1 | GCAGCAGTCAGTGG |
| 299. | ErbB-2-2 | CCATTGTCTAGCACGG |
| 300. | ErbB-2-3 | GGTCTCCATTGTCTAGC |
| 301. | ErbB-2-4 | GGTGGTATTGTTCAGC |
| 302. | ErbB-2-5 | GCTGGATCAAGACCC |
| 303. | ErbB-2-6 | CCACAAAATCGTGTCC |
| 304. | ErbB-2-7 | CCTTCCACAAAATCGTGTCC |
| 305. | ErbB-2-8 | GGTTGTTCTTGTGG |
| 306. | ErbB-2-9 | CCTCTTGGTTGTGC |
| 307. | ErbB-2-10 | CCAGAGTCTCAAACACTTGG |
| 308. | ErbB-2-11 | GGTAACCTGTGATCTCTTCC |
| 309. | ErbB-2-12 | CCTGCAGTACTCGG |
| 310. | ErbB-2-13 | GGCATTCACATACTCC |
| 311. | ErbB-2-14 | GCAAACAGTGCCTGGC |
| 312. | ErbB-2-15 | CGCATCGTGTACTTCCG |
| 313. | ErbB-2-16 | GCACGTTCCGAGCG |
| 314. | ErbB-2-17 | GGTACCAGATACTCC |
| 315. | ErbB-2-18 | CCAGTGGAGACCTGG |
| 316. | ErbB-2-19 | CCTGAGGACACATCAGG |
| 317. | ErbB-2-20 | CCTCACTTGGTTGTGAGC |
| 318. | ErbB-2-21 | GGAAGATGTCCTTCC |
| 319. | ErbB-2-22 | GCACACTGCTCATGGC |
| 320. | ErbB-2-23 | GCTGTCACCTCTTGG |
| 321. | ErbB-2-24 | CCTCTGCTGTCACC |
| 322. | ErbB-2-25 | CCACACATCACTCTGG |
| 323. | ErbB-2-26 | CCTCCTCTTCAGAGG |

FIG. 3-6

| | | |
|---|---|---|
| 324. | ErbB-2-27 | CCTTCTGGTTCACACTGG |
| 325. | ErbB-2-28 | CATGGTGCTCACTGCG |
| 326. | ErbB-2-29 | CTTGGTTGTGAGCG |
| 327. | ErbB-2-30 | GGACAGGCAGTCAC |
| 328. | ErbB-2-31 | GTCACCTCTTGGTTGTGC |
| 329. | ErbB-2-32 | CCAGAGTCTCAAACAC |
| 330. | ErbB-2-33 | CACATACTCCCTGG |
| 331. | ErbB-2-34 | GACCAGCACGTTCCG |
| 332. | ErbB-2-35 | GTTGGTGTCTATCAGTG |
| 333. | ErbB-2-36 | CCCTGGTAGAGGTG |
| 334. | ErbB-2-37 | CTCAAACACTTGGAGC |
| 335. | ErbB-2-38 | CACACATCACTCTGGTGG |
| 336. | ErbB-2-39 | GCACAGACAGTGCGC |
| 337. | ErbB-2-40 | CATGGCAGCAGTCAG |
| 338. | ErbB-2-41 | CTGCTCATGGCAGCAG |
| 339. | ErbB-2-42 | CATCTGGAAACTTCCAGATG |
| 340. | ErbB-2-43 | CTGGAAACTTCCAG |
| 341. | ErbB-2-44 | CATAACTCCACACATCACTC |
| 342. | ErbB-2-45 | CACCATAACTCCACACATC |
| 343. | ErbB-2-46 | CTGGTGGGTGAACC |
| 344. | ErbB-2-47 | CGGATTACTTGCAGG |
| 345. | ErbB-2-48 | CGCTAGGTGTCAGCG |
| 346. | ErbB-2-49 | GCCATCACGTATGC |
| 347. | ErbB-2-50 | GCATACACCAGTTCAGC |
| 348. | ErbB-2-51 | CCATCAAATACATCGG |
| 349. | ErbB-2-52 | CCAGCAGAAGTCAGG |
| 350. | ErbB-2-53 | GCTTCATGTCTGTGC |
| 351. | ErbB-2-54 | GGTGAGTTCCAGGTTTCC |
| 352. | ErbB-2-55 | CCACAAAATCGTGTCCTGG |
| 353. | ErbB-2-56 | CCCTTACACATCGG |
| 354. | ErbB-2-57 | GCAGCTCACAGATGC |
| 355. | ErbB-2-58 | GCACTGGTAACTGC |
| 356. | ErbB-2-59 | CCTGGATATTGGCACTGG |
| 357. | ErbB-2-60 | CCAGCAAACTCCTGG |
| 358. | ErbB-2-61 | GCAGAAATGCCAGGC |
| 359. | ErbB-2-62 | CCATTGTGCAGAATTCG |
| 360. | ErbB-2-63 | CCCTGCAGTACTCGG |
| 361. | ErbB-2-64 | GGCATTCACATACTCCC |
| 362. | ErbB-2-65 | GGTCAGGTTTCACACC |
| 363. | ErbB-2-66 | CCAGGTCCACACAGG |
| 364. | ErbB-2-67 | CCTTGTCATCCAGG |
| 365. | ErbB-2-68 | GGATCCCAAAGACC |
| 366. | ErbB-2-69 | CCTCAACACTTTGATGG |
| 367. | ErbB-2-70 | GCTGTGTCACCAGC |
| 368. | ErbB-2-71 | GGTCTAAGAGGCAGCC |
| 369. | ErbB-2-72 | GGCAATCTGCATACACC |
| 370. | ErbB-2-73 | CCTGTGTACGAGCC |
| 371. | ErbB-2-74 | CCATCCACTTGATGG |
| 372. | ErbB-2-75 | CCCACACAGTCACACC |
| 373. | ErbB-2-76 | CCATCGTAAGGTTTGG |
| 374. | ErbB-2-77 | CCTTTTCCAGCAGG |
| 375. | ErbB-2-78 | GGAGAATTCAGACACC |
| 376. | ErbB-2-79 | CCAAGTCCTCATTCTGG |
| 377. | ErbB-2-80 | CCATCAGTCTCAGAGG |
| 378. | ErbB-2-81 | CCTTTGAAGGTGCTGG |
| 379. | ErbB-2-82 | GGCATGGCAGGTTCC |
| 380. | ErbB-2-83 | CCTGGCATGGCAGG |
| 381. | ErbB-2-N-1 | AGATGTATAGGTAA |
| 382. | ErbB-2-N-2 | ATTTTCACATTCTC |
| 383. | ErbB-2-N-3 | AATTTTCACATTCTC |
| 384. | ErbB-2-N-4 | AATTTTCACATTCT |
| 385. | ErbB-2-N-5 | GAATTTTCACATTC |
| 386. | ErbB-2-N-6 | GGAATTTTCACATT |
| 387. | ErbB-2-N-7 | AGATTTCTTTGTTG |
| 388. | ErbB-2-N-8 | AAGATTTCTTTGTTG |
| 389. | ErbB-2-N-9 | AAGATTTCTTTGTT |

FIG. 3-7

| | | |
|---|---|---|
| 390. | ErbB-2-N-10 | TAAGATTTCTTTGTT |
| 391. | ErbB-2-N-11 | CTAAGATTTCTTTGTT |
| 392. | ErbB-2-N-12 | TAAGATTTCTTTGT |
| 393. | ErbB-2-N-13 | CTAAGATTTCTTTGT |
| 394. | ErbB-2-N-14 | CTAAGATTTCTTTG |
| 395. | ErbB-2-N-15 | TCTAAGATTTCTTT |
| 396. | ErbB-2-N-16 | GTCTAAGATTTCTTT |
| 397. | ErbB-2-N-17 | GTCTAAGATTTCTT |
| 398. | ErbB-2-N-18 | TTCGTCTAAGATTT |
| 399. | ErbB-2-N-19 | ATTTTGACATGGTT |
| 400. | ErbB-2-N-20 | AATTTTGACATGGTT |
| 401. | ErbB-2-N-21 | AATTTTGACATGGT |
| 402. | ErbB-2-N-22 | TAATTTTGACATGGT |
| 403. | ErbB-2-N-23 | TAATTTTGACATGG |
| 404. | ErbB-2-N-24 | GTAATTTTGACATG |
| 405. | ErbB-2-N-25 | TGTAATTTTGACATG |
| 406. | ErbB-2-N-26 | TGTAATTTTGACAT |
| 407. | ErbB-2-N-27 | TCTGTAATTTTGACAT |
| 408. | ErbB-2-N-28 | CTGTAATTTTGACA |
| 409. | ErbB-2-N-29 | TCTGTAATTTTGACA |
| 410. | ErbB-2-N-30 | TCTGTAATTTTGAC |
| 411. | ErbB-2-N-31 | GTCTGTAATTTTGA |
| 412. | ErbB-2-N-32 | AAGTCTGTAATTTTGA |
| 413. | ErbB-2-N-33 | AGTCTGTAATTTTG |
| 414. | ErbB-2-N-34 | AAGTCTGTAATTTTG |
| 415. | ErbB-2-N-35 | AAGTCTGTAATTTT |
| 416. | ErbB-2-N-36 | GAAGTCTGTAATTTT |
| 417. | ErbB-2-N-37 | GAAGTCTGTAATTT |
| 418. | ErbB-2-N-38 | ATGTAGACATCAAT |
| 419. | ErbB-2-N-39 | ATCATCCAACATTT |
| 420. | ErbB-2-N-40 | AATCATCCAACATTT |
| 421. | ErbB-2-N-41 | AATCATCCAACATT |
| 422. | ErbB-2-N-42 | ACCATCAAATACAT |
| 423. | ErbB-2-N-43 | AAAAACGTCTTTGA |
| 424. | ErbB-2-N-44 | TTTTGTTCTTAGACA |
| 425. | ErbB-2-N-45 | TTTTGTTCTTAGAC |
| 426. | ErbB-2-N-46 | TAAACAGAAAAGCA |
| 427. | ErbB-2-N-47 | ACTAAACAGAAAAG |
| 428. | ErbB-2-N-48 | AAACTAAACAGAAAAG |
| 429. | ErbB-2-N-49 | AACTAAACAGAAAA |
| 430. | ErbB-2-N-50 | AAACTAAACAGAAAA |
| 431. | ErbB-2-N-51 | AAACTAAACAGAAA |
| 432. | ErbB-2-N-52 | TAAAAACTAAACAGAAA |
| 433. | ErbB-2-N-53 | AAAACTAAACAGAA |
| 434. | ErbB-2-N-54 | GTAAAAACTAAACAGAA |
| 435. | ErbB-2-N-55 | AAAAACTAAACAGA |
| 436. | ErbB-2-N-56 | TAAAAACTAAACAGA |
| 437. | ErbB-2-N-57 | TAAAAACTAAACAG |
| 438. | ErbB-2-N-58 | GTAAAAACTAAACA |
| 439. | ErbB-2-N-59 | AAAAAGTAAAAACTAAACA |
| 440. | ErbB-2-N-60 | AGTAAAAACTAAAC |
| 441. | ErbB-2-N-61 | AAAAAAAGTAAAAACTAAAC |
| 442. | ErbB-2-N-62 | AAGTAAAAACTAAA |
| 443. | ErbB-2-N-63 | AAAAAAAGTAAAAACTAAA |
| 444. | ErbB-2-N-64 | AAAGTAAAAACTAA |
| 445. | ErbB-2-N-65 | AAAAGTAAAAACTA |
| 446. | ErbB-2-N-66 | AAAAAAAGTAAAAACTA |
| 447. | ErbB-2-N-67 | AAAAAGTAAAAACT |
| 448. | ErbB-2-N-68 | AAAAAAAGTAAAAACT |
| 449. | ErbB-2-N-69 | AAAAAAAGTAAAAAC |
| 450. | ErbB-2-N-70 | CAAAAAAAGTAAAAAC |
| 451. | ErbB-2-N-71 | AAAAAAAAGTAAAAA |
| 452. | ErbB-2-N-72 | CAAAAAAAGTAAAA |
| 453. | ErbB-2-N-73 | AACAAAACAAAAAAAGTAAA |
| 454. | ErbB-2-N-74 | AAACAAAAAAAGTA |
| 455. | ErbB-2-N-75 | CAAAACAAAAAAAGTA |
| 456. | ErbB-2-N-76 | CAAAACAAAAAAAGT |

FIG. 3-8

| | | |
|---|---|---|
| 457. | ErbB-2-77 | CAAAACAAAAAAAG |
| 458. | ErbB-2-78 | CTTTAAAAAAACAAAAC |
| 459. | ErbB-2-79 | TCTTTAAAAAAACAAA |
| 460. | ErbB-2-80 | GTCTTTAAAAAAACAAA |
| 461. | ErbB-2-81 | GTCTTTAAAAAAACA |
| 462. | ErbB-2-82 | GTCTTTAAAAAAAC |
| 463. | ErbB-2-83 | TTTATTTCGTCTTT |
| 464. | ErbB-2-84 | TCTTTATTTCGTCT |
| 465. | ErbB-2-85 | TATTTGCAAATGGA |
| 466. | ErbB-2-86 | TATATTTGCAAATGG |
| 467. | ErbB-2-87 | TATATTTGCAAATG |
| 468. | ErbB-2-88 | CAAAATATATTTGCAAATG |
| 469. | ErbB-2-89 | CAAAATATATTTGCAAAT |
| 470. | ErbB-2-90 | CAAAATATATTTGCA |
| 471. | ErbB-2-91 | CAAAATATATTTGC |
| 472. | ErbB-2-92 | TTCCAAAATATATTG |
| 473. | ErbB-2-93 | TTTTCCAAAATATATTT |
| 474. | ErbB-2-94 | GTTTTCCAAAATATATT |
| 475. | ErbB-2-95 | GTTTTCCAAAATAT |
| 476. | c-fos-1 | GGTTAGGCAAAGCC |
| 477. | c-fos-2 | CCGAGAACATCATCGTGG |
| 478. | c-fos-3 | CCGAGAACATCATCGTG |
| 479. | c-fos-4 | CCGAGAACATCATCG |
| 480. | c-fos-5 | CGTAGTCTGCGTTGAAGC |
| 481. | c-fos-6 | CCATGCTGGAGAAGG |
| 482. | c-fos-7 | CCGTGCAGAAGTCC |
| 483. | c-fos-8 | GGAATGAAGTTGGC |
| 484. | c-fos-9 | TGACCGTGGGAATG |
| 485. | c-fos-10 | TGGCAGTGACCGTG |
| 486. | c-fos-11 | AGATGGCAGTGACC |
| 487. | c-fos-12 | CGAGATGGCAGTGACC |
| 488. | c-fos-13 | CCAGCCACTGCAGG |
| 489. | c-fos-14 | GCACCAGCCACTGC |
| 490. | c-fos-15 | CCCTGGAGTAAGCC |
| 491. | c-fos-16 | GGAGATAACTGTTCCACC |
| 492. | c-fos-17 | GGAGATAACTGTTCC |
| 493. | c-fos-18 | CTTCTAGTTGGTCTG |
| 494. | c-fos-19 | CATCTTCTAGTTGG |
| 495. | c-fos-20 | TCTCATCTTCTAGTTGG |
| 496. | c-fos-21 | CTGCAAAGCAGACTTCTC |
| 497. | c-fos-22 | CCTTCAGCAGGTTGG |
| 498. | c-fos-23 | CCCAGGTCATCAGG |
| 499. | c-fos-24 | CCAGTCAGATCAAGG |
| 500. | c-fos-25 | GGTGAAGGCCTCCTC |
| 501. | c-fos-26 | CAGGGTGAAGGCCTC |
| 502. | c-fos-27 | CCTGGATGATGCTGG |
| 503. | c-fos-28 | CCACTGTGCAGAGG |
| 504. | c-fos-29 | GGAGTACAGGTGACC |
| 505. | c-fos-30 | GCTCATTGCTGCTGC |
| 506. | c-fos-31 | GGAAGGCTCATTGCTGC |
| 507. | c-fos-N-1 | TTTTCTCTTCTTCT |
| 508. | c-fos-N-2 | ATCTTATTCCTTTC |
| 509. | c-fos-N-3 | CATCTTATTCCTTT |
| 510. | c-fos-N-4 | TAGTTTTTCCTTCT |
| 511. | c-fos-N-5 | TCTAGTTTTTCCTT |
| 512. | c-fos-N-6 | AACTCTAGTTTTTC |
| 513. | c-fos-N-7 | GAACTCTAGTTTTT |
| 514. | c-fos-N-8 | TGAACTCTAGTTTTT |
| 515. | c-fos-N-9 | ATGAACTCTAGTTTTT |
| 516. | c-fos-N-10 | TGAACTCTAGTTTT |
| 517. | c-fos-N-11 | ATGAACTCTAGTTTT |
| 518. | c-fos-N-12 | ATGAACTCTAGTTT |
| 519. | TGF-B2-1 | GCACACAGTAGTGC |

FIG. 3-9

| | | |
|---|---|---|
| 520. | TGF-B2-2 | GCAGGATCAGAAAAGC |
| 521. | TGF-B2-3 | GCAGGTAGACAGGC |
| 522. | TGF-B2-4 | GCTTGCTCAGGATCTGC |
| 523. | TGF-B2-5 | GCAAGTCCCTGGTGC |
| 524. | TGF-B2-6 | CCTGGAGCAAGTCC |
| 525. | TGF-B2-7 | CGTAGTACTCTTCGTCG |
| 526. | TGF-B2-8 | CGTAGTACTCTTCG |
| 527. | TGF-B2-9 | GTAAACCTCCTTGG |
| 528. | TGF-B2-10 | GTCTATTTTGTAAACCTCC |
| 529. | TGF-B2-11 | GCATGTCTATTTTGTAAACC |
| 530. | TGF-B2-12 | GGCATCAAGGTACCC |
| 531. | TGF-B2-13 | GGCATCAAGGTACC |
| 532. | TGF-B2-14 | GCTTTCACCAAATTGGAAGC |
| 533. | TGF-B2-15 | GAGAATCTGATATAGCTC |
| 534. | TGF-B2-16 | GGAGATGTTAAATCTTTGG |
| 535. | TGF-B2-17 | GCTGTCGATGTAGC |
| 536. | TGF-B2-18 | CCAGGTTCCTGTCTTTATGG |
| 537. | TGF-B2-19 | CAGCAGGGACAGTG |
| 538. | TGF-B2-20 | CTTGCTTCTAGTTCTTCAC |
| 539. | TGF-B2-21 | GCCATCAATACCTGC |
| 540. | TGF-B2-22 | GGTGCCATCAATACC |
| 541. | TGF-B2-23 | CCACTGGTATATGTGG |
| 542. | TGF-B2-24 | GGACTTTATAGTTTTCTG |
| 543. | TGF-B2-25 | CTCAAGTCTGTAGGAG |
| 544. | TGF-B2-26 | GGTCTGTTGTGACTC |
| 545. | TGF-B2-27 | CAATTATCCTGCACATTTC |
| 546. | TGF-B2-28 | GCAGCAATTATCCTGC |
| 547. | TGF-B2-29 | GGCAGCAATTATCC |
| 548. | TGF-B2-30 | GGTTCGTGTATCCATTTCC |
| 549. | TGF-B2-31 | GCACAGAAGTTGGC |
| 550. | TGF-B2-32 | CCAGCACAGAAGTTGG |
| 551. | TGF-B2-33 | GTGCTGAGTGTCTG |
| 552. | TGF-B2-34 | CCTGCTGTGCTGAGTG |
| 553. | TGF-B2-35 | GCTCAGGACCCTGC |
| 554. | TGF-B2-36 | GCAGCAAGGGAAGC |
| 555. | TGF-B2-37 | CCAATGTAGTAGAGAATGG |
| 556. | TGF-B2-38 | GCTGCATTTGCAAG |
| 557. | TGF-B2-N-1 | AAAAAAGAAATCAA |
| 558. | TGF-B2-N-2 | AAAAAAAGAAATCAA |
| 559. | TGF-B2-N-3 | AAAAAAAAGAAATCAA |
| 560. | TGF-B2-N-4 | TAAAAAAAAGAAATCAA |
| 561. | TGF-B2-N-5 | ATAAAAAAAAGAAATCAA |
| 562. | TGF-B2-N-6 | AATAAAAAAAAGAAATCAA |
| 563. | TGF-B2-N-7 | GAATAAAAAAAAGAAAT |
| 564. | TGF-B2-N-8 | AGAATAAAAAAAAGAAAT |
| 565. | TGF-B2-N-9 | CAGAATAAAAAAAA |
| 566. | TGF-B2-N-10 | TCAGAATAAAAAAAA |
| 567. | TGF-B2-N-11 | TTGTTTTTAAAAGT |
| 568. | TGF-B2-N-12 | AGTTGTTTTTAAAA |
| 569. | TGF-B2-N-13 | AAGTTGTTTTTAAAA |
| 570. | TGF-B2-N-14 | AAAGTTGTTTTTAAAA |
| 571. | TGF-B2-N-15 | AAAAGTTGTTTTTAAAA |
| 572. | TGF-B2-N-16 | AAAAAGTTGTTTTTAAAA |
| 573. | TGF-B2-N-17 | AAAAAAGTTGTTTTTAAAA |
| 574. | TGF-B2-N-18 | AAAAAAAGTTGTTTTTAAAA |
| 575. | TGF-B2-N-19 | AAAAAAAAGTTGTTTTTAA |
| 576. | TGF-B2-N-20 | TTTTTAAAAAAGTG |
| 577. | TGF-B2-N-21 | TTTTTTAAAAAAGTG |
| 578. | TGF-B2-N-22 | ATTTTTTAAAAAAGTG |
| 579. | TGF-B2-N-23 | CATTTTTTAAAAAAGT |
| 580. | TGF-B2-N-24 | GCATTTTTTAAAAAAA |
| 581. | TGF-B2-N-25 | TGCATTTTTTAAAAAAA |
| 582. | TGF-B2-N-26 | AGCTTATTTTAAAT |
| 583. | TGF-B2-N-27 | AAGCTTATTTTAAAT |
| 584. | TGF-B2-N-28 | TAAGCTTATTTTAAAT |
| 585. | TGF-B2-N-29 | TGTAATTATTAGAT |

FIG. 3-10

| | | |
|---|---|---|
| 586. | TGF-B2-N-30 | ATGTAATTATTAGAT |
| 587. | TGF-B2-N-31 | TGATGTAATTATTA |
| 588. | TGF-B2-N-32 | ATGATGTAATTATTA |
| 589. | TGF-B2-N-33 | ATGGTATTATATAA |
| 590. | TGF-B2-N-34 | TATGGTATTATATAA |
| 591. | TGF-B2-N-35 | TTATGGTATTATATAA |
| 592. | TGF-B2-N-36 | TTTATGGTATTATATAA |
| 593. | TGF-B2-N-37 | ATTTATGGTATTATATAA |
| 594. | TGF-B2-N-38 | AATCATATTAGAAA |
| 595. | TGF-B2-N-39 | TTACAATCATATTA |
| 596. | TGF-B2-N-40 | TTTACAATCATATTA |
| 597. | rb-1 | GGCATGACGCCTTTCC |
| 598. | rb-2 | GCATGACGCCTTTC |
| 599. | rb-3 | GCCTGACGAGAGGC |
| 600. | rb-4 | CTCAAGCCTGACGAG |
| 601. | rb-5 | CCACAGTTCCTTTTTC |
| 602. | rb-6 | GCTGCAATAAAGATACAG |
| 603. | rb-7 | GCTGCAATAAAGATAC |
| 604. | rb-8 | GGACACTGATTTCTATG |
| 605. | rb-9 | GCATTATCAACTTTGG |
| 606. | rb-10 | ACTTTTAGCACCAATG |
| 607. | rb-11 | CCAAGAAACTTTTAGCACC |
| 608. | rb-12 | CCAGATCATCTTCC |
| 609. | rb-13 | AGTCAAGGACACATAG |
| 610. | rb-14 | TCTTTGAGCAACATGG |
| 611. | rb-15 | GGGTATAACAGCTG |
| 612. | rb-16 | GAGGTGAACCATTAATGG |
| 613. | rb-17 | TCTTCGTATCGTTTAG |
| 614. | rb-18 | TGTTGGATAGTGTTC |
| 615. | rb-19 | GTTGATCACTTGCTG |
| 616. | rb-20 | GGATTCCATTACTCG |
| 617. | rb-21 | GACATATGAAAAATGTTGTC |
| 618. | rb-22 | GCCAATAAAGACATATG |
| 619. | rb-23 | CCAGAATCAAGATTCTG |
| 620. | rb-24 | CTGTTCCAGAATCAAG |
| 621. | rb-25 | GACAAATCTGTTCCAGAATC |
| 622. | rb-26 | GGAAAGACAAATCTGTTCC |
| 623. | rb-27 | GATTAAGAGGACAAGC |
| 624. | rb-28 | GGAAGATTAAGAGG |
| 625. | rb-29 | GCAGTGTGATTATTCTGG |
| 626. | rb-30 | GGAGAAAGATACATATCTG |
| 627. | rb-31 | GGAGATCTTACAGG |
| 628. | rb-32 | GCATTTGCAGTAGAATTTAC |
| 629. | rb-33 | CAGTGAAAGAGAGG |
| 630. | rb-34 | GCTAGCCGATACAC |
| 631. | rb-35 | GGAAGATCCTTGTATGC |
| 632. | rb-36 | GCATGAGGAAGATCC |
| 633. | rb-37 | GGAGTCATTTTTGTTG |
| 634. | rb-38 | CCAATTGATACTAAGATTC |
| 635. | rb-39 | TCTTTTGAGCACACG |
| 636. | rb-40 | CCTTCAGCACTTCTTTTG |
| 637. | rb-41 | GGTTGCTTCCTTCAGC |
| 638. | rb-42 | CAGTGGTTTAGGAG |
| 639. | rb-43 | CCTGAGATCCTCATTTC |
| 640. | rb-44 | CCAAGGTCCTGAGATCC |
| 641. | rb-45 | GGTGTACACAGTGTCC |
| 642. | rb-N-1 | TATCTTTAATTTCT |
| 643. | rb-N-2 | TCTTTTGAATATAA |
| 644. | rb-N-3 | TTCTTTTGAATATAA |
| 645. | rb-N-4 | TTTCTTTTGAATATAA |
| 646. | rb-N-5 | TTTTCTTTTGAATATAA |
| 647. | rb-N-6 | TTTTTCTTTTGAATATAA |
| 648. | rb-N-7 | ATTTCTATGTTTTT |
| 649. | rb-N-8 | TTAAAGAATTTATG |
| 650. | rb-N-9 | GTTAAAGAATTTAT |

FIG. 3-11

| # | ID | Sequence |
|---|---|---|
| 651. | rb-N-10 | AGTTAAAGAATTTAT |
| 652. | rb-N-11 | AAGTTAAAGAATTTAT |
| 653. | rb-N-12 | TAAGTTAAAGAATTTAT |
| 654. | rb-N-13 | TTTAGTAAGTTAAA |
| 655. | rb-N-14 | TTTTAGTAAGTTAAA |
| 656. | rb-N-15 | ATTTCTTTTAGTAA |
| 657. | rb-N-16 | AATTTCTTTTAGTAA |
| 658. | rb-N-17 | ATCAATTTCTTTTA |
| 659. | rb-N-18 | TATCAATTTCTTTTA |
| 660. | rb-N-19 | AATATATAAGTTCA |
| 661. | rb-N-20 | AAATATATAAGTTCA |
| 662. | rb-N-21 | CAAATATATAAGTT |
| 663. | rb-N-22 | TCAAATATATAAGTT |
| 664. | rb-N-23 | TGTCAAATATATAA |
| 665. | rb-N-24 | AATTTATTTCAGTA |
| 666. | rb-N-25 | AATAAAAATGTGAT |
| 667. | rb-N-26 | TAATAAAAATGTGAT |
| 668. | rb-N-27 | TAGCTAATAAAAAT |
| 669. | rb-N-28 | TTAGCTAATAAAAAT |
| 670. | rb-N-29 | TTTAGCTAATAAAAAT |
| 671. | rb-N-30 | AATAAAATAGTCAA |
| 672. | rb-N-31 | TAATAAAATAGTCAA |
| 673. | rb-N-32 | TTAATAAAATAGTCAA |
| 674. | rb-N-33 | TTTAATAAAATAGTCAA |
| 675. | rb-N-34 | GTTTAATAAAATAGT |
| 676. | rb-N-35 | AGTTTAATAAAATAGT |
| 677. | rb-N-36 | GAGTTTAATAAAATA |
| 678. | rb-N-37 | AGAGTTTAATAAAATA |
| 679. | rb-N-38 | AATAATTCTTGTAT |
| 680. | rb-N-39 | TATATTACATTCAT |
| 681. | rb-N-40 | ATCTATATTACATT |
| 682. | rb-N-41 | ATAAACATTTTTCA |
| 683. | rb-N-42 | AATAAACATTTTTCA |
| 684. | rb-N-43 | AAATAAACATTTTTCA |
| 685. | rb-N-44 | GAAATAAACATTTTT |
| 686. | rb-N-45 | TGAAATAAACATTTTT |
| 687. | rb-N-46 | TTGAAATAAACATTTTT |
| 688. | rb-N-47 | TTTGAAATAAACATTTTT |
| 689. | rb-N-48 | TTTTGAAATAAACATTTTT |
| 690. | rb-N-49 | TTTTTGAAATAAACATTTT |
| 691. | rb-N-50 | ATTTTTGAAATAAACATTTT |
| 692. | rb-N-51 | AATTTTTTGAAATAAACATT |
| 693. | rb-N-52 | AAATTTTTTGAAATAAACATT |
| 694. | rb-N-53 | AAAATTTTTGAAATAAACAT |
| 695. | rb-N-54 | TAAAATTTTTGAAATAAACA |
| 696. | rb-N-55 | ATAAAATTTTTGAAATAAAC |
| 697. | rb-N-56 | TATAAAATTTTTGAAATAAA |
| 698. | rb-N-57 | GTATAAAATTTTTGAAAT |
| 699. | rb-N-58 | GGTATAAAATTTTT |
| 700. | rb-N-59 | AGGTATAAAATTTTT |
| 701. | rb-N-60 | AAGGTATAAAATTTTT |
| 702. | rb-N-61 | AAAGGTATAAAATTTTT |
| 703. | rb-N-62 | AAAAGGTATAAAATTTTT |
| 704. | rb-N-63 | TAAAAGGTATAAAATTTTT |
| 705. | rb-N-64 | ATAAAAGGTATAAAATTTTT |
| 706. | rb-N-65 | TTTAGAAAGATTTTT |
| 707. | rb-N-66 | AAGATAAATTTCTT |
| 708. | rb-N-67 | TAAGATAAATTTCTT |
| 709. | rb-N-68 | TTAAGATAAATTTCTT |
| 710. | rb-N-69 | TTTAAGATAAATTTCTT |
| 711. | rb-N-70 | TTTTAAGATAAATTTCTT |
| 712. | rb-N-71 | TTTTTAAGATAAATTTCTT |
| 713. | rb-N-72 | ATTTTTAAGATAAATTTCTT |
| 714. | rb-N-73 | TATTTTTAAGATAAATTTCT |
| 715. | rb-N-74 | TTATTTTTAAGATAAATT |
| 716. | rb-N-75 | TTTATTTTTAAGATAAATT |
| 717. | rb-N-76 | CTTTATTTTTAAGATAAAT |

FIG. 3-12

| # | Name | Sequence |
|---|---|---|
| 718. | rb-N-77 | TCTTTATTTTTAAGATAAAT |
| 719. | rb-N-78 | ATCTTTATTTTTAAGATAAA |
| 720. | rb-N-79 | ATCTTTATTTTTAA |
| 721. | rb-N-80 | GATCTTTATTTTTAA |
| 722. | rb-N-81 | AGATCTTTATTTTTAA |
| 723. | rb-N-82 | TAGATCTTTATTTTTAA |
| 724. | rb-N-83 | AATCATCATTAATT |
| 725. | rb-N-84 | AAATCATCATTAATT |
| 726. | rb-N-85 | AAAATCATCATTAATT |
| 727. | rb-N-86 | TAAAATCATCATTAATT |
| 728. | rb-N-87 | TTAAAATCATCATTAATT |
| 729. | rb-N-88 | TTTAAAATCATCATTAATT |
| 730. | rb-N-89 | ATTTAAAATCATCATTAATT |
| 731. | rb-N-90 | AATTTAAAATCATCATTAA |
| 732. | rb-N-91 | GAATTTAAAATCAT |
| 733. | rb-N-92 | TGAATTTAAAATCAT |
| 734. | rb-N-93 | TTAAAATAGGAAAT |
| 735. | rb-N-94 | AATTTCTCTTTAAA |
| 736. | rb-N-95 | AAATTTCTCTTTAAA |
| 737. | rb-N-96 | TAAAATTTTGAATG |
| 738. | rb-N-97 | CTAAAATTTTGAAT |
| 739. | rb-N-98 | TTTGCTAAAATTTT |
| 740. | rb-N-99 | ATATGAAAAATGTT |
| 741. | rb-N-100 | TTTTAAATTAAGCA |
| 742. | rb-N-101 | TTGTAAAAATCAAA |
| 743. | rb-N-102 | TTTGTAAAAATCAAA |
| 744. | rb-N-103 | TTTGATAAAACTTT |
| 745. | rb-N-104 | ATGTTTTATCATTT |
| 746. | rb-N-105 | AATGTTTTATCATTT |
| 747. | rb-N-106 | AAATGTTTTATCATTT |
| 748. | rb-N-107 | TAAATGTTTTATCATTT |
| 749. | rb-N-108 | TCTAAATGTTTTAT |
| 750. | rb-N-109 | TTCTAAATGTTTTAT |
| 751. | rb-N-110 | TAAGATCAAATAAA |
| 752. | rb-N-111 | ATAAGATCAAATAAA |
| 753. | rb-N-112 | AATAAGATCAAATAAA |
| 754. | rb-N-113 | TAATAAGATCAAATAAA |
| 755. | rb-N-114 | TTAATAAGATCAAATAAA |
| 756. | rb-N-115 | TTTAATAAGATCAAATAAA |
| 757. | rb-N-116 | TTGTTTAATAAGAT |
| 758. | rb-N-117 | ATTGTTTAATAAGAT |
| 759. | rb-N-118 | TGATTGTTTAATAA |
| 760. | rb-N-119 | TTGATTGTTTAATAA |
| 761. | rb-N-120 | TTTGATTGTTTAATAA |
| 762. | rb-N-121 | TTTTATAAAACAGT |
| 763. | rb-N-122 | TTTTTATAAAACAGT |
| 764. | rb-N-123 | TTTTTTATAAAACAGT |
| 765. | rb-N-124 | CTTTTTTATAAAACA |
| 766. | rb-N-125 | ACTTTTTTATAAAACA |
| 767. | rb-N-126 | CACTTTTTTATAAAA |
| 768. | rb-N-127 | ACACTTTTTTATAAAA |
| 769. | rb-N-128 | TACACTTTTTTATAAAA |
| 770. | rb-N-129 | ATACACTTTTTTATAAAA |
| 771. | rb-N-130 | ATTTTGAATTTAAG |
| 772. | rb-N-131 | GATTTTGAATTTAA |
| 773. | rb-N-132 | TGATTTTGAATTTAA |
| 774. | rb-N-133 | ATGATTTTGAATTTAA |
| 775. | rb-N-134 | AATGATTTTGAATTTAA |
| 776. | rb-N-135 | ATAATAGAATCATA |
| 777. | rb-N-136 | TATAATAGAATCATA |
| 778. | rb-N-137 | TATAATAGAATCAT |
| 779. | rb-N-138 | TACTATAATAGAAT |
| 780. | rb-N-139 | ATACTATAATAGAAT |
| 781. | rb-N-140 | AATACTATAATAGAAT |
| 782. | rb-N-141 | AGAATACTATAATA |
| 783. | rb-N-142 | TAGAATACTATAATA |
| 784. | rb-N-143 | ATAGAATACTATAATA |

FIG. 3-13

| | | |
|---|---|---|
| 785. | rb-N-144 | TATAGAATACTATAATA |
| 786. | rb-N-145 | TTATAGAATACTATAATA |
| 787. | rb-N-146 | AATATTTGTTTTCA |
| 788. | rb-N-147 | AAATATTTGTTTTCA |
| 789. | rb-N-148 | AAAATATTTGTTTCA |
| 790. | rb-N-149 | CAAAATATTTGTTTT |
| 791. | rb-N-150 | AAATTTTATATGGA |
| 792. | rb-N-151 | TGAAATTTTATATG |
| 793. | rb-N-152 | CTGAAATTTTATAT |
| 794. | rb-N-153 | TCTGAAATTTTATAT |
| 795. | rb-N-154 | TTCTGAAATTTTATAT |
| 796. | rb-N-155 | ATCTGATTTATTTT |
| 797. | rb-N-156 | AAGATATTAAATGT |
| 798. | rb-N-157 | TGAAGATATTAAAT |
| 799. | rb-N-158 | ATAAATAACAATGA |
| 800. | rb-N-159 | TATAAATAACAATGA |
| 801. | rb-N-160 | GTATAAATAACAAT |
| 802. | rb-N-161 | TGTATAAATAACAAT |
| 803. | rb-N-162 | TTGTATAAATAACAAT |
| 804. | rb-N-163 | TCTTGTATAAATAA |
| 805. | rb-N-164 | ATCTTGTATAAATAA |
| 806. | rb-N-165 | ATTCTTGTATAAATAA |
| 807. | rb-N-166 | ACAACTTTTTAAAAT |
| 808. | rb-N-167 | TACAACTTTTTAAAT |
| 809. | rb-N-168 | TACAACTTTTTAAA |
| 810. | rb-T-1 | CGGGGGGTTTTGGGCGGCATG |
| 811. | rb-T-2 | TTTTCGGGGGGTTTTGGGCGGCA |
| 812. | rb-T-3 | TCGGGGGGTTTTGGGCGG |
| 813. | rb-T-4 | GGTGGCGGCCGTTTTTCGGGGGGT |
| 814. | rb-T-5 | CCGGGGGTTCCGCGGCGGCAGCG |
| 815. | rb-T-6 | CGGGGGTTCCGCGGCGG |
| 816. | rb-T-7 | GGCGGCGGTGCCGGGGGTTCCGC |
| 817. | rb-T-8 | GGAGGGGGCGGCGGCGGCGGTG |
| 818. | rb-T-9 | GGGGCGGCGGCGGCGG |
| 819. | rb-T-10 | GGGCGGCGGCGGCG |
| 820. | rb-T-11 | AGGGGGCCTGGTGGAAG |
| 821. | rb-T-12 | TAGGGGGCCTGGTG |
| 822. | rb-T-13 | GTAGGGGGCCTGGT |
| 823. | rb-T-14 | GAGGTATTGGTGACAAGGTAGGGGGC |
| 824. | rb-T-15 | TCTTCAGGGGTGAAATATAGATGTTC |
| 825. | rb-T-16 | GGACTCTTCAGGGGTG |

FIG. 4-1

| | |
|---|---|
| 826 | TCGGACTATA CTGC |
| 827 | CAGTTCGGAC TATACT |
| 828 | AAGCCTAAGA CGCA |
| 829 | GCCCAAGTTC AACA |
| 830 | TGAAAAGTCG CGGT |
| 831 | GGTTAATTAA GATGCCTC |
| 832 | TCTCTAAGAG CGCA |
| 833 | ACGTGAGGTT AGTTTG |
| 834 | CACGTGAGGT TAGT |
| 835 | CATAGAACAG TCCG |
| 836 | CAGTCATAGA ACAGTC |
| 837 | CTTTGCAGTC ATAGAACA |
| 838 | TGCAGTCATA GAAC |
| 839 | GGTCGTTTCC ATCT |
| 840 | CATAGAAGGT CGTTTC |
| 841 | CGTCATAGAA GGTC |
| 842 | CATCGTCATA GAAGG |
| 843 | GGACGGGAGG AACGAGGCGT TGAG |
| 844 | TAGCCATAAG GTCC |
| 845 | GGTTACTGTA GCCA |
| 846 | GGTTACTGTA GCCA |
| 847 | AGTTCTTGGC GCGGAGGT |
| 848 | AGGTGAGGAG GTCCGAGT |
| 849 | TGGACTGGAT TATCAG |
| 850 | GTGGTGGTGA TGTGCCCG |
| 851 | TGTCACGTTC TTGG |
| 852 | CTCATCTGTC ACGT |
| 853 | CGAAGCCCTC GGCGAACC |
| 854 | GCGTGTTCTG GCTGTGCAGT TCGG |
| 855 | CTGCCCCGTT GACC |
| 856 | AGGTTTGCGT AGAC |
| 857 | GGTTGAAGTT GCTG |
| 858 | CTGGGTTGAA GTTG |
| 859 | TGCTGCACGG GCATCTGCTG |
| 860 | GGCACTGTCT GAGGCTCCTC CTTCAGG |
| 861 | ACTCCATGTC GATG |
| 862 | CTCTCCGCCT TGATCC |
| 863 | GTTCCTCATG CGTTC |
| 864 | CTGAGCTTTC AAGG |
| 865 | GCGATTCTCT CCAGCTTCCT TTTTCG |
| 866 | CTGAGCTTTC AAGGTTTTCA CTTTTTCCTC |
| 867 | TCCCTGAGCA TGTT |
| 868 | TCTGTTTAAG CTGTGC |
| 869 | CTTTCTGTTT AAGCTGTG |
| 870 | GGTTCATGAC TTTCTG |
| 871 | CGTGGTTCAT GACT |
| 872 | ACTGTTAACG TGGTTC |
| 873 | CCACTGTTAA CGTG |
| 874 | CCCACTGTTA ACGT |
| 875 | AGCATGAGTT GGCA |
| 876 | GCGTTAGCAT GAGT |
| 877 | GTTTGCAACT GCTG |
| 878 | CAAAATGTTT GCAACTGC |

FIG. 4-2

| | |
|---|---|
| 879 | TCCATTTTAG TGCACATC |
| 880 | CTGTTCCATT TTAGTGCA |
| 881 | GTGTATGAGT CGTC |
| 882 | CTGTGTATGA GTCG |
| 883 | CGTAGCTGTG TATG |
| 884 | TCGTGTAGAG AGAG |
| 885 | AGTTTGTAGT CGTGTAGA |
| 886 | GTTTGTAGTC GTGTAG |
| 887 | AGTTTGTAGT CGTG |
| 888 | GGAGTTTGTA GTCG |
| 889 | TCAGGAGTTT GTAGTC |
| 890 | GTTTCAGGAG TTTGTAGT |
| 891 | TCGGTTTCAG GAGT |
| 892 | TTGAGACTCC GGTA |
| 893 | ACCAGAAAAG TAGCTG |
| 894 | CCTGACCAGA AAAG |
| 895 | ATTCAGGCGT TCCA |
| 896 | GGTAAAAGTA CTGTCC |
| 897 | GGGTAAAAGT ACTGTC |
| 898 | GCACCTCCAC CGCTGCCA |
| 899 | CTCCTGCTCC TCGGTGAC |
| 900 | GCTTTGACAA AGCC |
| 901 | CTTGTGCAGA TCGT |
| 902 | TCATCTTGTG CAGATC |
| 903 | GTTCATCTTG TGCAGA |
| 904 | CGTGGTTCAT CTTG |
| 905 | TCACGTGGTT CATC |
| 906 | GGTTGGTGTA AACG |
| 907 | TACGAGCTCC CGGTCCCGAC |
| 908 | TAGCTGATGG TGGT |
| 909 | TCCTTGAAGG TGGA |
| 910 | TCTTCCATGT TGATGG |
| 911 | CTTTGATGCG CTCT |
| 912 | CTCCACTTTG ATGC |
| 913 | GCTCCAGCTT CCGCTTCCGG CACTTGGTGG |
| 914 | GGCCTTGAGC GTCTTCACCT TGTCCTCCAG |
| 915 | TGACCTTCTG TTTGAG |
| 916 | CATGACCTTC TGTTTG |
| 917 | GTCATGACCT TCTG |
| 918 | CGAGAACATC ATCG |
| 919 | GTAGTCTGCG TTGA |
| 920 | GCTGCAGCGG GAGGATGACG |
| 921 | AGTAAGAGAG GCTATC |
| 922 | GTAGTAAGAG AGGC |
| 923 | GGTAGTAAGA GAGG |
| 924 | GTGAGTGGTA GTAAGA |
| 925 | GTCCGTGCAG AAGTCCTG |
| 926 | GAATGAAGTT GGCACT |
| 927 | CGAATGAAGT TGGC |
| 928 | GGGAATGAAG TTGG |
| 929 | GCTGCACCAG CCACTGCAGG TCCGGACTGG |
| 930 | TCATGGTCTT CACAAC |
| 931 | CAATGCTCTG CGCTCGGCCT CCTGTCATGG |

FIG. 4-3

| | |
|---|---|
| 932 | CTAGAGTTCC TCAC |
| 933 | GAGTACGCTA GAGT |
| 934 | GAAGAGTACG CTAG |
| 935 | CTGCTTCCCA CCCAGCCCCC ACATTCCC |
| 936 | TTCATCCTCT GTACTGGGCT |
| 937 | GTTACGGATG TGCA |
| 938 | CAGTTACGGA TGTG |
| 939 | CCAGTTACGG ATGT |
| 940 | AGAGGTCTGAG TTGG |
| 941 | GTGAGACTCA GAGT |
| 942 | TCTTAGGGTG AGAC |
| 943 | GAGAGTACTT CTTAGG |
| 944 | GGAAGAAACT ATGAGAGT |
| 945 | CTTAGGGAAG AAACTATG |
| 946 | CGGTAAGAAA CTTAGG |
| 947 | AGCATGCGGT AAGA |
| 948 | GTCTGAAAGC ATGC |
| 949 | AGAACAAAGA AGAGCC |
| 950 | CAAGAGAACA AAGAAGAG |
| 951 | CAGCAAGAGA ACAAAG |
| 952 | TCCTCAGCAA GAGA |
| 953 | AGGTGTGACT TGCA |
| 954 | GAATAGGTGT GACTTG |
| 955 | CAGAATAGGT GTGACT |
| 956 | GCAGAATAGG TGTG |
| 957 | CAGTTGCAGA ATAGGT |
| 958 | GAAACCATTT CTGACC |
| 959 | TGTGAAACCA TTTCTGAC |
| 960 | CACTGTGAAA CCATTTCT |
| 961 | CCACTGTGAA ACCA |
| 962 | AGAACTGGCT CCTGCAGCTT CCCTGCTTCC |
| 963 | CACCTCCATT CACCC |
| 964 | CAGTAAAAGT GTCTGC |
| 965 | CGACATTCAG TAAAAGTG |
| 966 | GACCGACATT CAGT |
| 967 | CTTCTGGAGA TAACTAGA |
| 968 | CATCTTATTC CTTTCCCT |
| 969 | CAGCCATCTT ATTCCT |
| 970 | TGCAGCCATC TTATTC |
| 971 | GAGTGTATCA GTCAG |
| 972 | GGAGTGTATC AGTC |
| 973 | CTTGGAGTGT ATCAGT |
| 974 | ACAGAGTACC TACC |
| 975 | CCAACTTTCC CTTAAG |
| 976 | CCTTATGCTC AATCTC |
| 977 | GTCTTACTCA AGGG |
| 978 | ACAGTCTTAC TCAAGG |
| 979 | CATAAGACAC AGTCTTAC |
| 980 | GAAAGCATAA GACACAGT |
| 981 | GGAAAGCATA AGACAC |
| 982 | AGGGATAAAG GAAAGC |
| 983 | CCTGTATACA GAGG |
| 984 | TGTCTCCTGT ATACAG |

FIG. 4-4

| | |
|---|---|
| 985 | CATCTTCTAG TTGGTC |
| 986 | CTCATCTTCT AGTTGG |
| 987 | CTTCTCATCT TCTAGTTG |
| 988 | CAAAAGCAGAC TTCTCA |
| 989 | CTGCAAAGCA GACT |
| 990 | CTAGTTTTTC CTTCTCCT |
| 991 | TCTAGTTTTT CCTTCTCC |
| 992 | CAGGATGAAC TCTAGT |
| 993 | TCGTAGAAGG TCGT |
| 994 | AGGGTTACTG TAGC |
| 995 | GTAGTGGTGA TGTG |
| 996 | CGTCGTAGAA GGTC |
| 997 | TTTCGTGCAC ATCC |
| 998 | AGTTTGTAGT CGTGAAGA |
| 999 | CGAGAACATC ATGG |
| 1000 | GTAGTAGGAA AGGC |
| 1001 | GGTAGTAGGA AAGG |
| 1002 | GGAATGGTAG TAGG |
| 1003 | GGTCATTGAG AAGAG |
| 1004 | GCTAATGTTC TTGACC |
| 1005 | GCCAAGGTCCTCAT |
| 1006 | GGAGTCTATCTCCA |
| 1007 | CCAAAGAATCCTGACT |
| 1008 | CACATGCTTAGTGG |
| 1009 | CTCGTAAATGACCG |
| 1010 | AGGAATCTCGTAAATGAC |
| 1011 | CAGCAGCGATTCAT |
| 1012 | GGAGATCATCAAAGGA |
| 1013 | CTCAGCAATGGTCA |
| 1014 | GATCTCGAACACCT |
| 1015 | CACAATCTCGATCTTTCT |
| 1016 | CCTTCTTAAAGATTGGCT |
| 1017 | CACATACCAACTGG |
| 1018 | AGCTTGATGTGAGG |
| 1019 | GAAGTTGTAGCTTGATGT |
| 1020 | GCTTGAAGTTGTAGCT |
| 1021 | CTGCTTGAAGTTGTAG |
| 1022 | GACACAACTCCTCT |
| 1023 | TCCTTTGATAGACACAAC |
| 1024 | CTCGTTTGATAGACAC |
| 1025 | GGTTAGCACACACT |
| 1026 | GGTAACGGTTAGCA |
| 1027 | CGTAACACATTTAGAAGC |
| 1028 | CTCATCCGTAACAC |
| 1029 | CCGGTAAGTATTGTAGTT |
| 1030 | GGTGTATTTCCTTGAC |
| 1031 | ACATACCAACTGGTGT |
| 1032 | GTCCCTATACGAAC |
| 1033 | TTCATGTCTG TGCC |
| 1034 | GTAGGTGAGT TCCA |
| 1035 | GTTGTGAGCG ATGA |
| 1036 | CATAGTTGTC CTCAAAGA |
| 1037 | GGCATAGTTG TCCT |

FIG. 4-5

| | |
|---|---|
| 1038 | CATTGTCTAG CACG |
| 1039 | CTCCATTGTC TAGC |
| 1040 | GTATTGTTCA GCGG |
| 1041 | TACCGATCTC TGTGAG |
| 1042 | CACAAAATCG TGTCCT |
| 1043 | TCCTTCCACA AAATCG |
| 1044 | GTGGAAGATG TCCT |
| 1045 | TCTTGTGGAA GATGTC |
| 1046 | TCTATCAGTG TGAGAG |
| 1047 | GGTTGGTGTC TATC |
| 1048 | ACATCGGAGA ACAG |
| 1049 | CCTTACACAT CGGA |
| 1050 | ACAATCCTCA GAACTC |
| 1051 | GCTCTGACAA TCCT |
| 1052 | TGGTTGAAGT GGAG |
| 1053 | CTGTGGTTGA AGTG |
| 1054 | GTTGTAGGTG ACCA |
| 1055 | CTGTGTTGTA GGTG |
| 1056 | GACTCAAACG TGTC |
| 1057 | CATGGACTCA AACG |
| 1058 | CGAATGTATA CCGG |
| 1059 | CCGAATGTAT ACCG |
| 1060 | GCCGAATGTA TACC |
| 1061 | GTAGTTGTAG GGAC |
| 1062 | TAGAAAGGTA GTTGTAGG |
| 1063 | GTAGAAAGGT AGTTGTAG |
| 1064 | CGTAGAAAGG TAGTTG |
| 1065 | CCGTAGAAAG GTAG |
| 1066 | GACCATAGCA CACT |
| 1067 | GGATATTGGC ACTG |
| 1068 | CCTGGATATT GGCA |
| 1069 | GCTCCCAAAG ATCT |
| 1070 | CCCATCAAAG CTCT |
| 1071 | CAAACACTTG GAGC |
| 1072 | GTCTCAAACA CTTGGA |
| 1073 | GAGTCTCAAA CACTTG |
| 1074 | GTAACCTGTG ATCTCT |
| 1075 | GGTAACCTGT GATC |
| 1076 | GTATAGGTAA CCTGTG |
| 1077 | TGAGATGTAT AGGTAACC |
| 1078 | TGCTGAGATG TATAGG |
| 1079 | CCATGCTGAG ATGT |
| 1080 | GGATTACTTG CAGG |
| 1081 | TGTTATGGTG GATGAG |
| 1082 | GGTGTTATGG TGGA |
| 1083 | GCAGTTGACA CACT |
| 1084 | AGTACTCGGC ATTC |
| 1085 | CATTCACATA CTCCCT |
| 1086 | TCCAAAACAG GTCACT |
| 1087 | GGTCCTTATA GTGG |
| 1088 | CAGAATGCCA ACCA |
| 1089 | ACGAGAATGC CAAC |
| 1090 | GATCCCAAAG ACCA |

FIG. 4-6

| | |
|---|---|
| 1091 | TCGCTTGATG AGGA |
| 1092 | CATCGTGTAC TTCC |
| 1093 | GCATCGTGTA CTTC |
| 1094 | ACTGTGCCAA AAGC |
| 1095 | CTTGTAGACT GTGC |
| 1096 | CCCTTGTAGA CTGT |
| 1097 | TCAACACTTT GATGGC |
| 1098 | CCCTCAACAC TTTG |
| 1099 | GTGTTTTCCC TCAACA |
| 1100 | GTATGCTTCG TCTAAG |
| 1101 | CGTATGCTTC GTCT |
| 1102 | CCATCACGTA TGCT |
| 1103 | GCATAAGCTG TGTC |
| 1104 | CATGGTCTAA GAGG |
| 1105 | CAATCTGCAT ACACCA |
| 1106 | GGCAATCTGC ATAC |
| 1107 | CTGTCTCGTC AATG |
| 1108 | CATAACTCCA CACATC |
| 1109 | AGTCACACCA TAACTC |
| 1110 | ACAGTCACAC CATAAC |
| 1111 | CCCCAAAAGT CATC |
| 1112 | TCGTTAAGGTT TGGC |
| 1113 | GATCCCATCG TAAG |
| 1114 | CAATGGTGCA GATG |
| 1115 | GACATCAATG GTGC |
| 1116 | GTAGACATCA ATGGTG |
| 1117 | CATGATCATG TAGACATC |
| 1118 | CCATGATCAT GTAGAC |
| 1119 | CATTTGACCA TGATCATG |
| 1120 | CCAACATTTG ACCATG |
| 1121 | TCATCCAACA TTTGACCA |
| 1122 | GAGTCAATCA TCCAACAT |
| 1123 | CAGAGTCAAT CATCCA |
| 1124 | CCGACATTCA GAGT |
| 1125 | GAATTCAGAC ACCAAC |
| 1126 | GATGACCACA AAGC |
| 1127 | CCATCAAATA CATCGG |
| 1128 | TCACCATCAA ATACATCG |
| 1129 | CAACGTAGCC ATCA |
| 1130 | ACGTCTTTGA CGAC |
| 1131 | CAAAACGTC TTTGACGA |
| 1132 | GGCAAAAACG TCTTTG |
| 1133 | CAAAGGCAAA AACGTC |
| 1134 | GTGTCAAGTA CTCG |
| 1135 | GTAATAGAGG TTGTCG |
| 1136 | CCCAGTAATA GAGG |
| 1137 | CATGGTGCTC ACTG |
| 1138 | GTGCCTGTAC GTAC |
| 1139 | TGCAGGTGGA TAGT |
| 1140 | CATGTCGATA GTCTTGCA |
| 1141 | GTCGATAGTC TTGC |
| 1142 | CCATGTCGAT AGTC |
| 1143 | CTCCATGTCG ATAG |

FIG. 4-7

| | |
|---|---|
| 1144 | CTTGGACAGG ATCT |
| 1145 | TGCTGTTGTA CAGG |
| 1146 | GTGCTGTTGT ACAG |
| 1147 | TTGGCGTAGT AGTC |
| 1148 | TCCACCATTA GCAC |
| 1149 | GATTTCGTTG TGGG |
| 1150 | GTCATAGATT TCGTTGTG |
| 1151 | TGTACTCTGC TTGAAC |
| 1152 | GTGTACTCTG CTTG |
| 1153 | TGCTGTGTGT ACTC |
| 1154 | CTGATGTGTT GAAGAACA |
| 1155 | CTCTGATGTG TTGAAG |
| 1156 | GCTCTGATGT GTTG |
| 1157 | GAGCTCTGAT GTGT |
| 1158 | CACTTTTAAC TTGAGCCT |
| 1159 | CTCCACTTTT AACTTGAG |
| 1160 | TGCTGTATTT CTGGTACA |
| 1161 | CCAGGAATTG TTGC |
| 1162 | TTGCTGAGGT ATCG |
| 1163 | GATAACCACT CTGG |
| 1164 | CAAAAGATAA CCACTCTG |
| 1165 | CGGTGACATC AAAAG |
| 1166 | CCTCAATTTC CCCT |
| 1167 | GTTATCCCTG CTGT |
| 1168 | GCAGTGTGTT ATCC |
| 1169 | GATGTCCACT TGCA |
| 1170 | TAGTGAACCC GTTG |
| 1171 | TGCCATGAAT GGTG |
| 1172 | GTTCATGCCA TGAATG |
| 1173 | CATGAGAAGC AGGA |
| 1174 | GCTTTGCAGA TGCT |
| 1175 | GAGCTTTGCA GATG |
| 1176 | TAGTTGGTGT CCAG |
| 1177 | CTGAAGCAAT AGTTGG |
| 1178 | AGCTGAAGCA ATAGTTGG |
| 1179 | GGAGCTGAAG CAAT |
| 1180 | CAATGTACAG CTGC |
| 1181 | GGAAGTCAAT GTACAG |
| 1182 | GGAAGTCAAT GTACAG |
| 1182 | CGGAAGTCAA TGTAC |
| 1183 | GCGGAAGTCA ATGT |
| 1184 | AGTTGGCATG GTAG |
| 1185 | GCAGAAGTTG GCAT |
| 1186 | CTCCAAATGT AGGG |
| 1187 | ACCTTGCTGT ACTG |
| 1188 | TGCTGGTTGT ACAG |
| 1189 | GGTTATGCTG GTTG |
| 1190 | GTAGTACACG ATGG |
| 1191 | CGTAGTACAC GATG |
| 1192 | CACGTAGTAC ACGA |
| 1193 | CATGTTGGAC AGCT |
| 1194 | GCACGATCAT GTTG |
| 1195 | CACACAGTAG TGCA |
| 1196 | GATCAGAAAA GCGC |

FIG. 4-8

| | |
|---|---|
| 1197 | ACCGTGACCA GATG |
| 1198 | GTAGACAGGC TGAG |
| 1199 | TATCGAGTGT GCTG |
| 1200 | TTGCGCATGA ACTG |
| 1201 | TTGCTCAGGA TCTG |
| 1202 | ACTGGTGAGC TTCA |
| 1203 | GCTCAGGATA GTCT |
| 1204 | TGTAGATGGA AATCACCT |
| 1205 | TGGTGCTGTT GTAG |
| 1206 | TTCTCCTGGA GCAA |
| 1207 | TACTCTTCGT CGCT |
| 1208 | CTTGGCGTAG TACT |
| 1209 | CGGCATGTCT ATTTTGTA |
| 1210 | CGGGATGGCA TTTT |
| 1211 | CTGTAGAAAG TGGG |
| 1212 | ACAATTCTGA AGTAGGGT |
| 1213 | ATTGCTGAGA CGTCAAAT |
| 1214 | TCTCCATTGC TGAG |
| 1215 | TCACCAAATT GGAAGCAT |
| 1216 | CTCTGAACTC TGCT |
| 1217 | AACGAAAGAC TCTGAACT |
| 1218 | TGGGTTCTGC AAAC |
| 1219 | CTGGCTTTTG GGTT |
| 1220 | GTTGTTCAGG CACT |
| 1221 | TCTGATATAG CTCAATCC |
| 1222 | TCTTTGGACT TGAGAATC |
| 1223 | TGGGTTGGAG ATGT |
| 1224 | TGCTGTCGAT GTAG |
| 1225 | ACAACTTTGC TGTCGA |
| 1226 | ATTCGCCTTC TGCT |
| 1227 | GAAGGAGAGC CATT |
| 1228 | TCAGTTACAT CGAAGG |
| 1229 | TGAAGCCATT CATGAACA |
| 1230 | TCCTGTCTTT ATGGTG |
| 1231 | AAATCCCAGG TTCC |
| 1232 | GGACAGTGTA AGCTTATT |
| 1233 | GTACAAAAGT GCAGCA |
| 1234 | TAGATGGTAC AAAAGTGC |
| 1235 | CACTTTTATT TGGGATGATG |
| 1236 | GCAAATCTTG CTTCTAGT |
| 1237 | GTGCCATCAA TACC |
| 1238 | GGTATATGTG GAGG |
| 1239 | TCTGATCACC ACTG |
| 1240 | TCCTAGTGGA CTTTATAG |
| 1241 | TTTTTCCTAG TGGACT |
| 1242 | CAATAACATT AGCAGG |
| 1243 | AAGTCTGTAG GAGG |
| 1244 | TCTGTTGTGA CTCAAG |
| 1245 | GTTGGTCTGT TGTG |
| 1246 | CAAAGCACGC TTCT |
| 1247 | TTTCTAAAGC AATAGGCC |
| 1248 | GCAATTATCC TGCACA |
| 1249 | ACGTAGGCAG CAAT |

FIG. 4-9

```
1250    ATCAATGTAA AGTGGACG
1251    CTAGATCCCT CTTG
1252    CCATTTCCAC CCTA
1253    TGGGTTCGTG TATC
1254    TGGCATTGTA CCCT
1255    TCCAGCACAG AAGT
1256    ATAAATACGG GCATGC
1257    AGTGTCTGAA CTCC
1258    TGTGCTGAGT GTCT
1259    ATAAGCTCAG GACC
1260    AGGAGAAGCA GATG
1261    AGCAAGGAGA AGCA
1262    AATCTTGGGA CACG
1263    TAGAGAATGG TTAGAGGT
1264    GTTTTGCCAA TGTAGTAG
1265    CTTGGGTGTT TTGC
1266    GCAAGACTTT ACAATC
1267    GCATTTGCAA GACTTTAC
1268    TTTAGCTGCA TTTGCAAG
1269    GCCACTTTTC CAAG
1270    TTGGTCTTGC CACT
1271    CAGCACACAG TAGT
1272    CGATAGTCTT GCAG
```

FIG. 5-1

| | | |
|---|---|---|
| 1273 | TGF-B2-14/1 | CTTTCACCAAATTGGAAG |
| 1274 | TGF-B2-14/2 | CACCAAATTGGAAGC |
| 1275 | TGF-B2-14/3 | TCACCAAATTGGAAGC |
| 1276 | TGF-B2-14/4 | CTCTGGCTTTTGGG |
| 1277 | TGF-B2-14/5 | CGGCATGTCTATTTTG |
| 1278 | relA-1 | CACTACAGACGAGC |
| 1279 | relA-2 | CGTGCACTACAGACG |
| 1280 | relA-3 | GGAACAGTTCGTCC |
| 1281 | relA-4 | GAACAGTTCGTCCATG |
| 1282 | relA-5 | CCAGAGTTTCGGTTC |
| 1283 | relA-6 | CTAGGACTGGGACAG |
| 1284 | relA-7 | CGCACTTGTAGCG |
| 1285 | relA-8 | CTCGCACTTGTAGC |
| 1286 | relA-9 | GCACTTGTAGC |
| 1287 | relA-10 | GCGCACTGTCCCTG |
| 1288 | relA-11 | CCAGGGAGATGCGC |
| 1289 | relA-12 | GCCGGTGAGGAGG |
| 1290 | relA-13 | CCGGTGAGGAGGG |
| 1291 | relA-14 | CGGTTCACTCGGC |
| 1292 | relA-15 | GAGTTTCGGTTCACTC |
| 1293 | relA-16 | GGCACGATTGTCAAAG |
| 1294 | relA-17 | CAGGCGTCACCCCC |
| 1295 | relA-18 | GCAGGCGTCACCC |
| 1296 | p105/p50-1 | CTCCCTCCTAAGC |
| 1297 | p105/p50-2 | CCCTCCTAAGCGG |
| 1298 | p105/p50-3 | CGAGTCCGCGTTCG |
| 1299 | p105/p50-4 | CATCTTCTGCCATTC |
| 1300 | p105/p50-5 | GTGTTTTCCCACCAG |
| 1301 | p105/p50-6 | GGTTTTGGTTCACTAG |
| 1302 | p105/p50-7 | GCATCTTCACGTCTCC |
| 1303 | p105/p50-8 | CTTCACGTCTCCTGTC |
| 1304 | p105/p50-9 | GTCACCGCGTAGTC |
| 1305 | p105/p50-10 | CAAATAGGCAAGGTC |
| 1306 | p105/p50-11 | CTTGCAAATAGGCAAG |
| 1307 | p105/p50-12 | TGCTTGCAAATAGG |
| 1308 | p105/p50-13 | CTGCTTGCAAATAGG |
| 1309 | p105/p50-14 | GCAGGTGGATATTT |
| 1310 | p105/p50-15 | CTGCTGTTGGCAG |
| 1311 | p105/p50-16 | CACTAGTTTCCAAGT |
| 1312 | p105/p50-17 | GTTTTGGTTCACTAG |
| 1313 | p105/p50-18 | CTTTGATTTCAGGATAG |

FIG. 5-2

| | | |
|---|---|---|
| 1314 | p105/p50-19 | GCACTTCTTCTTTATCT |
| 1315 | p105/p50-20 | CCAAGTCAGATTTCC |
| 1316 | p105/p50-21 | GTTTCCAAGTCAGATTTC |
| 1317 | p105/p50-22 | GGTTCACTAGTTTCC |
| 1318 | p105/p50-23 | GGTTTTGGTTCACTAG |
| 1319 | p105/p50-24 | CCGAAAAATTGGGCA |
| 1320 | p105/p50-25 | CCGAAAAATTGGG |
| 1321 | p105/p50-26 | CTATCCGAAAAATTGG |
| 1322 | p105/p50-27 | GTTGATAATGTCATCAG |
| 1323 | p105/p50-28 | CTCATGTTGATAATGTC |
| 1324 | p105/p50-29 | CTGTCACCGCGTAG |
| 1325 | p105/p50-30 | CGTCTCCTGTCACCG |
| 1326 | p105/p50-31 | CTTCACGTCTCCTG |
| 1327 | p105/p50-32 | GAGAACTTTATCATGTC |
| 1328 | p105/p50-33 | GCTATATGCAGGG |
| 1329 | p105/p50-34 | CCAGCTGCTATATGCAGG |
| 1330 | p105/p50-35 | AGGCTAAATTTTGCCT |
| 1331 | p105/p50-36 | GGCTAAATTTTGCC |
| 1332 | p105/p50-37 | GGCTAAATTTTGCCTTC |
| 1333 | p105/p50-38 | GCAGGCTAAATTTTGCC |
| 1334 | p105/p50-39 | GAGTTACCCAAGCG |
| 1335 | p105/p50-40 | CAGAGTTACCCAAGCG |
| 1336 | p105/p50-41 | CAGAGTTACCCAAG |
| 1337 | p105/p50-42 | ACAGAGTTACCAAG |
| 1338 | p105/p50-43 | GGTGCAAAACAGAG |
| 1339 | p105/p50-44 | CTAGGTGCAAAACAG |
| 1340 | p105/p50-45 | GAGAACTTTATCATGTCC |
| 1341 | p105/p50-46 | GCTAGATGAATGGC |
| 1342 | p105/p50-47 | GCAAACATGGCAGGC |
| 1343 | p105/p50-48 | CAGCAAACATGGCA |
| 1344 | p105/p50-49 | GCAGCAAACATGGC |
| 1345 | p105/p50-50 | AGCAGCAAACATGG |
| 1346 | p105/p50-51 | CAGCAGCAAACATG |
| 1347 | p105/p50-52 | AGCAGCAGCAAACA |
| 1348 | p105/p50-53 | CAGCAGCAGCAAACA |
| 1349 | p105/p50-54 | CAGCAGCAGCAAAC |
| 1350 | p105/p50-55 | CACCAGCAGCAGCA |
| 1351 | p105/p50-56 | GCATTGACGTCAGC |
| 1352 | p105/p50-57 | GATGTTGTCGTGCTC |
| 1353 | p105/p50-58 | TGAGATGTTGTCGTGCT |
| 1354 | p105/p50-59 | TGAGATGTTGTCGTG |

FIG. 5-3

| | | |
|---|---|---|
| 1355 | p105/p50-60 | GCCAATGAGATGTTG |
| 1356 | p105/p50-61 | CTGCCAATGAGATG |
| 1357 | p105/p50-62 | CACATGGGCATCAC |
| 1358 | p105/p50-63 | TGTCCACATGGCA |
| 1359 | p105/p50-64 | GTACTGTCCACATG |
| 1360 | p105/p50-65 | CAGCTGCTATATGC |
| 1361 | p105/p50-66 | GTTCTCCACCAGGG |
| 1362 | p105/p50-67 | AGTTCTCCACCAGG |
| 1363 | p105/p50-68 | CAAAGTTCTCCACCAG |
| 1364 | p105/p50-69 | CCAAGAGTCATCCAGG |
| 1365 | p105/p50-70 | CCCAAGAGTCATCC |
| 1366 | p105/p50-71 | CCTGCATTTTCCCAAG |
| 1367 | p105/p50-72 | TCCTGCATTTTCCC |
| 1368 | p105/p50-73 | GCCATATCTAGAGGC |
| 1369 | p105/p50-74 | TCACATCTTCAGCC |
| 1370 | p105/p50-75 | GCTTCACATCTTCAGC |
| 1371 | p105/p50-76 | CAGCTTCACATCTTC |
| 1372 | p105/p50-77 | GTAACTTATACAGCTGC |
| 1373 | p105/p50-78 | CCAGTTTTTGTCTGG |
| 1374 | p105/p50-79 | CCATTTGTCTCAGG |
| 1375 | p105/p50-80 | GTGTAGCCCATTTG |
| 1376 | p105/p50-81 | GCTTCGGTGTAGCC |
| 1377 | p105/p50-82 | GATCACTTCAATTGCTTC |
| 1378 | p105/p50-83 | CTTGTGGAGGCAGG |
| 1379 | p105/p50-84 | GCTGCCTTGTGGAG |
| 1380 | p105/p50-85 | CTATTTGCTGCCTTGTGG |
| 1381 | p105/p50-86 | GGATGTCTCCACGC |
| 1382 | p105/p50-87 | GGAAGGATGTCTCC |
| 1383 | p105/p50-88 | TGCGGAAGGATGTC |
| 1384 | p105/p50-89 | GTTTGCGGAAGGATGTC |
| 1385 | p105/p50-90 | GCTGAGTTTGCGGA |
| 1386 | p105/p50-91 | GGTAAAGCTGAGTTTG |
| 1387 | p105/p50-92 | TCGGTAAAGCTGAG |
| 1388 | p105/p50-93 | GACTCGGTAAAGCTG |
| 1389 | p105/p50-94 | AGAGACTCGGTAAAGC |
| 1390 | p105/p50-95 | GAAATTGTCAGCAGGC |
| 1391 | p105/p50-96 | GAAATTGTCAGCAGG |
| 1392 | p105/p50-97 | GGAAATTGTCAGCAGG |
| 1393 | p105/p50-98 | GGAAATTGTCAGCAG |
| 1394 | p105/p50-99 | GGGAAATTGTCAGC |
| 1395 | p105/p50-100 | GTGTGGGAAATTGTC |

FIG. 5-4

| | | |
|---|---|---|
| 1396 | p105/p50-101 | GGTTTACACGGTGTG |
| 1397 | p105/p50-102 | GCTTTGGTTTACACG |
| 1398 | p105/p50-103 | GCACCTTTGGGATGC |
| 1399 | NFKB2-1 | CCAGGTTCTGCTTCC |
| 1400 | NFKB2-2 | GCTCTGTCTAGTGGC |
| 1401 | NFKB2-3 | ACTCTCCATGTCTC |
| 1402 | NFKB2-4 | CAACTCTCCATGTCTC |
| 1403 | NFKB2-5 | CAACTCTCCATGTC |
| 1404 | NFKB2-6 | AGCAACTCTCCATG |
| 1405 | NFKB2-7 | GTAGCAACTCTCCATG |
| 1406 | NFKB2-8 | GTAGCAACTCTCCA |
| 1407 | NFKB2-9 | GGTTGTAGCAACTCTCC |
| 1408 | NFKB2-10 | CGGGCAGTCCTCCA |
| 1409 | NFKB2-11 | GCACCGGGCAGTC |
| 1410 | NFKB2-12 | AGGCACCGGGCAG |
| 1411 | NFKB2-13 | GTGTGTTACCAGGTC |
| 1412 | NFKB2-14 | TGTGTGTTACCAGGT |
| 1413 | NFKB2-15 | TGGGTCACTGTGTG |
| 1414 | NFKB2-16 | CAGACTGTGGGCATG |
| 1415 | NFKB2-17 | CCCACCAGACTGTGGG |
| 1416 | NFKB2-18 | CCACCAGACTGTGG |
| 1417 | NFKB2-19 | TGCCCACCAGACTG |
| 1418 | NFKB2-20 | CGGCTTCCTCCCC |
| 1419 | NFKB2-21 | CCTTGTCTTCCACC |
| 1420 | NFKB2-22 | ACCGAGGCTGCCAC |
| 1421 | NFKB2-23 | GGAAGAAACCGAGG |
| 1422 | NFKB2-24 | GGGAAGAAACCGAG |
| 1423 | NFKB2-25 | GGCCATCTGCGCC |
| 1424 | NFKB2-26 | GCGGCCATCTGCG |
| 1425 | NFKB2-27 | GTGGCGGCCATCTG |
| 1426 | NFKB2-28 | ACCGTGGCGGCCAT |
| 1427 | NFKB2-29 | GCCGCTCAATCTTCATC |
| 1428 | NFKB2-30 | CTTCATCTTGTGATAGG |
| 1429 | NFKB2-31 | GCTCAATCTTCATCTTG |
| 1430 | NFKB2-32 | CAGAAACACTGTTACAG |
| 1431 | NFKB2-33 | CAGTTGCAGAAACACTG |
| 1432 | NFKB2-34 | GTTTCAGTTGCAGAAAC |
| 1433 | NFKB2-35 | CTTCCACCAGAGGG |
| 1434 | NFKB2-36 | GTCTTCCACCAGAG |
| 1435 | NFKB2-37 | CTTGTCTTCCACCAGAG |
| 1436 | NFKB2-38 | TCCTTGTCTTCCAC |

FIG. 5-5

| | | |
|---|---|---|
| 1437 | NFKB2-39 | CTTCCTTGTCTTCCAC |
| 1438 | NFKB2-40 | CATCTTGTGATAGGG |
| 1439 | NFKB2-41 | GCTAGGTGCAGTGGT |
| 1440 | NFKB2-42 | GATGGCTAGGTGCA |
| 1441 | NFKB2-43 | GTGGATGATGGCTAG |
| 1442 | NFKB2-44 | CCCGTGGATGATGG |
| 1443 | NFKB2-45 | CTGCCCGTGGATGA |
| 1444 | NFKB2-46 | AGAGCCTCCACCCA |
| 1445 | NFKB2-47 | GTTGTACTCTCGAGC |
| 1446 | NFKB2-48 | CGTTGTACTCTCG |
| 1447 | NFKB2-49 | CGCGTTGTACTCTC |
| 1448 | NFKB2-50 | GAGTCTCCATGCCG |
| 1449 | NFKB2-51 | CTGAGTCTCCATGC |
| 1450 | NFKB2-52 | CATGGCTGAGTCTC |
| 1451 | NFKB2-53 | TGCATGGCTGAGTC |
| 1452 | NFKB2-54 | GCGTTCACGTTGGC |
| 1453 | NFKB2-55 | GTGCGAGCGTTCAC |
| 1454 | NFKB2-56 | AGGTGCGAGCGTTC |
| 1455 | NFKB2-57 | GCAAAGGTGCGAGC |
| 1456 | NFKB2-58 | CCTGGTGGCTCAGG |
| 1457 | NFKB2-59 | GTCAGTCACCTGAG |
| 1458 | NFKB2-60 | CAGGTCAGTCACCTG |
| 1459 | NFKB2-61 | CAGCAGGTCAGTCAC |
| 1460 | NFKB2-62 | GCAGCAGGTCAGTC |
| 1461 | NFKB2-63 | CATTTAGCAGCAAGGTC |
| 1462 | NFKB2-64 | GCAGCATTTAGCAGC |
| 1463 | NFKB2-65 | CTGAGCAGCATTTAG |
| 1464 | NFKB2-66 | CCCATGAGAATCCT |
| 1465 | NFKB2-67 | CCTTCCCATGAGAATCC |
| 1466 | NFKB2-68 | TCCTCCCCTTCCCA |
| 1467 | NFKB2-69 | GCCTCCAGTAGACC |
| 1468 | NFKB2-70 | GTCAGACAGGGCCT |
| 1469 | NFKB2-71 | CCATGTCAGACAGG |
| 1470 | NFKB2-72 | GGCCCATGTCAGAC |
| 1471 | TANK-1 | GCTATTCCTGAAAATCAC |
| 1472 | TANK-2 | CCTCTTGTCTTCTTACC |
| 1473 | TANK-3 | GGAGAAGAAACCTCTTG |
| 1474 | TANK-4 | CCTTGCTGAAGTTTCTT |
| 1475 | TANK-5 | CCAAGACTCCTTGC |
| 1476 | TANK-6 | CCCTTTCATGGAGC |
| 1477 | TANK-7 | CCTCTTGGTGTGAC |

FIG. 5-6

| | | |
|---|---|---|
| 1478 | TANK-8 | GACTAAGGATGCCG |
| 1479 | TANK-9 | GTGGCAGGACTAAGG |
| 1480 | TANK-10 | AGACGTGGCAGGAC |
| 1481 | I-kappa-Bepsilon-1 | CTTCCAGCAGGCAG |
| 1482 | I-kappa-Bepsilon-2 | GTTCCTCTGCCTGG |
| 1483 | I-kappa-Bepsilon-3 | GATGTTCCTCTGCTG |
| 1484 | I-kappa-Bepsilon-4 | GAGATGTTCCTCTGCC |
| 1485 | I-kappa-Bepsilon-5 | GTGAGATGTTCCTCTG |
| 1486 | I-kappa-Bepsilon-6 | CAGAGAGTGAGATGTTCC |
| 1487 | I-kappa-Bepsilon-7 | CCAGAGAGTGAGATGTTC |
| 1488 | I-kappa-Bepsilon-8 | GGTCCAGAGAGTGAG |
| 1489 | I-kappa-Bepsilon-9 | GAGGTCCAGAGAGTG |
| 1490 | I-kappa-Bepsilon-10 | GGTCCTGTAGTGCC |
| 1491 | TRAF-6-1 | GATTTTATGATGCAGGC |
| 1492 | TRAF-6-2 | GACCTGCATCCCTTATTG |
| 1493 | TRAF-6-3 | TAGTTGATTTTCCAGCAG |
| 1494 | TRAF-6-4 | GAATCTCACGTTTTGC |
| 1495 | TRAF-6-5 | CAGAGAAAGAATCTCACG |
| 1496 | TRAF-6-6 | TTTCACCATCAGAGAAAAG |
| 1497 | TRAF-6-7 | CATTTGGACATTTCACC |
| 1498 | TRAF-6-8 | CCTTCATTTGGACATTTC |
| 1499 | TRAF-6-9 | CAATGTGCTTGATGATCC |
| 1500 | Rank-1 | CGCATCGGATTTCTC |
| 1501 | Rank-2 | CAAACCGCATCGGATTTC |
| 1502 | Rank-3 | GAACTGCAAACCGC |
| 1503 | Rank-4 | GCAGAGAAGAACTGC |
| 1504 | Rank-5 | GCAAGTAAACATGGG |
| 1505 | Rank-6 | GGTCCACGTTTTGG |
| 1506 | Rank-7 | GCAAGGGTCCACGTTT |
| 1507 | Rank-8 | TGGCTTCTTCTTCAGGG |
| 1508 | Rank-9 | TCCTGCTGGCTTCTTC |
| 1509 | Rank-10 | GTCCTGCTGGCTTC |
| 1510 | IL-5-1 | GGTAGTCTAGGAATTGG |
| 1511 | IL-5-2 | CTTGCAGGTAGTCTAGG |
| 1512 | IL-5-3 | GAAACTCTTGCAGGTAG |
| 1513 | IL-5-4 | CACCAAGAAACTCTTGC |
| 1514 | IL-5-5 | CATTACACCAAGAAACTC |
| 1515 | IL-5-6 | CTCGGTGTTCATTACACC |
| 1516 | IL-5-7 | CTTTCTATTATCCACTCG |
| 1517 | IL-5-8 | CCAGTTTAGTCTCAACTT |
| 1518 | IL-5-9 | AACCAGTTTAGTCTCAAC |

FIG. 5-7

| | | |
|---|---|---|
| 1519 | IL-5-10 | ACAAACCAGTTTAGTCTC |
| 1520 | IL-13-1 | CTCGCGAAAAAGTTTCTT |
| 1521 | IL-13-2 | CCCTCGCGAAAAAGTTTC |
| 1522 | IL-13-3 | GTCCCTCGCGAAAAAG |
| 1523 | IL-13-4 | CAGTTGAACCGTCCC |
| 1524 | IL-13-5 | GCTTTCGAAGTTTCAGTT |
| 1525 | IL-13-6 | GATGCTTTCGAAGTTTC |
| 1526 | IL-13-7 | CTGTCTCTGCAAATAATG |
| 1527 | IL-15-1 | CACTTATTACATTCACCC |
| 1528 | IL-15-2 | TTTTCCTCCAGTTCCTC |
| 1529 | IL-15-3 | GGACAATATGTACAAACTC |
| 1530 | IL-15-5 | GTTGATGAACATTTGGAC |
| 1531 | IL-15-5 | GTGTTGATGAACATTTGG |
| 1532 | I-kappaB(newmember)-1 | CAAAATTTGGCCAGGG |
| 1533 | I-kappaB(newmember)-2 | GCCCAAAATTTGGCC |
| 1534 | I-kappaB(newmember)-3 | CCCAGCCCAAAATTTGG |
| 1535 | I-kappaB(newmember)-4 | GTCCCCAGCCCAAAATT |
| 1536 | I-kappaB(newmember)-5 | AAATCGCCAGAGGCTG |
| 1537 | I-kappaB(newmember)-6 | ACCAAATCGCCAGAGG |
| 1538 | I-kappaB(newmember)-7 | CATCACCAAATCGCCAG |
| 1539 | Prostaglan.Rec.EP3-1 | TAGGAGTGGTTGAGGC |
| 1540 | Prostaglan.Rec.EP3-2 | GTGTAGGAGTGGTTGAG |
| 1541 | Prostaglan.Rec.EP3-3 | CTGTGTAGGAGTGG |
| 1542 | Prostaglan.Rec.EP3-4 | CCCACATGCCTGTG |
| 1543 | Prostaglan.Rec.EP3-5 | CGATGAACAACGAG |
| 1544 | Prostaglan.Rec.EP3-6 | CTGGCGATGAACAACG |
| 1545 | Prostaglan.Rec.EP3-7 | CGCTGGCGATGAAC |
| 1546 | Prostaglan.Rec.EP3-8 | GAGCTAGTCCCGTTG |
| 1547 | Prostaglan.Rec.EP3-9 | GCGAAGAGCTAGTCC |
| 1548 | Prostaglan.Rec.EP3-10 | CCAGTTATGCGAAGAGC |
| 1549 | Prostaglan.Rec.EP3-11 | CCCCAGTTATGCGAAG |
| 1550 | PresenilinI-1 | CACATGCTTGGCGC |
| 1551 | PresenilinI-2 | CATCACATGCTTGGCG |
| 1552 | PresenilinI-3 | GACAAAGAGCATGATCAC |
| 1553 | PresenilinI-4 | GAGTCACAGGGACAAAG |
| 1554 | PresenilinI-5 | GAGAGTCACAGGGAC |
| 1555 | PresenilinI-6 | GCAGAGAGTCACAGG |
| 1556 | PresenilinI-7 | CCATGCAGAGAGTC |
| 1557 | PresenilinI-8 | CCACCATGCAGAGAG |
| 1558 | PresenilinI-9 | TAGCCACGACCACC |
| 1559 | PresenilinI-10 | GATTAGCTGCCCATCCTT |

FIG. 5-8

| | | |
|---|---|---|
| 1560 | Presenilinl-11 | GGTATAGATTAGCTGCC |
| 1561 | Presenilinl-12 | GTATCTTCTGTGAATGGG |
| 1562 | Presenilinl-13 | CTGGCCCACAGTCT |
| 1563 | Presenilinl-14 | CTCTGGCCCACAGT |
| 1564 | Presenilinl-15 | TGCAGGGCTCTCTG |
| 1565 | Presenilinl-16 | AGTGCAGGGCTCTC |
| 1566 | Presenilinl-17 | CACTGATCATGATGGC |
| 1567 | Presenilinl-18 | GACACTGATCATGATGGC |
| 1568 | Presenilinl-19 | ACAATGACACTGATCATG |
| 1569 | Presenilinl-20 | GAACCACCAGGAGGAT |
| 1570 | Presenilinl-21 | GACACAAAACAGCCACT |
| 1571 | Presenilinl-22 | GTGGACCTTTCGGAC |
| 1572 | Presenilinl-23 | CAACCAGCATACGAAGT |
| 1573 | Presenilinl-24 | TCCCTCTGGGCTTC |
| 1574 | Presenilinl-25 | ACTGTCCCTCTGGG |
| 1575 | Presenilinl-26 | GACTGTCCCTCTGG |
| 1576 | Presenilinl-27 | CCTAGATGACTGTCCC |
| 1577 | Presenilinl-28 | CAGCGAGGATACTGC |
| 1578 | Presenilinl-29 | CTTCACCAGCGAGGAT |
| 1579 | Presenilinl-30 | TTTCCTCTGGGTCTTCAC |
| 1580 | Presenilinl-31 | CTTTCCTCTGGGTCTTC |
| 1581 | Presenilinl-32 | CTCCCAATCCAAGTTTT |
| 1582 | TRADD-1 | TTCATCCCCGGAGCC |
| 1583 | TRADD-2 | TTCTTCATCCCGGAGC |
| 1584 | TRADD-3 | GCTCAGCCAGTTCTTC |
| 1585 | TRADD-4 | GACAGAGAGGGCAC |
| 1586 | TRADD-5 | CTTCACCTCCGACAG |
| 1587 | TRADD-6 | GAAAAGTCTGGGCAGG |
| 1588 | TRADD-7 | GACCCTGGAACAGAAAAG |
| 1589 | TRADD-8 | CTGACCCTGGAACAG |
| 1590 | TRADD-9 | ACTACAGGCTGACCCT |
| 1591 | TRADD-10 | ATTCACTACAGGCTGACC |
| 1592 | TRADD-11 | CGATTCACTACAGG |
| 1593 | TRADD-12 | GGCCGATTCACTAC |
| 1594 | TRADD-13 | CGAACGTCTGTTGGTC |
| 1595 | TRADD-14 | CGCGAACGTCTGTTG |
| 1596 | PKA-1 | CTTCTGTTTGTCGAGGAT |
| 1597 | PKA-2 | TTCACCACCTTCTGTTTG |
| 1598 | PKA-3 | AGGATGCGCTTTTCATTC |
| 1599 | PKA-4 | AGCTTGCAGGATGCG |
| 1600 | PKA-5 | GTTGACAGCTTGCAGGAT |

FIG. 5-9

| | | |
|---|---|---|
| 1601 | PKA-6 | GGAACGGAAAGTTGACAG |
| 1602 | PKA-7 | AACTCGAGTTTGACGAGG |
| 1603 | PKA-8 | TGTCCTTGAAGGAGAAC |
| 1604 | PKA-9 | CGTACTCCATGACCATGT |
| 1605 | PKA-10 | GCACGTACTCCATGAC |
| 1606 | PKA-11 | GATTCTCCGGCTTCAG |
| 1607 | PKA-12 | TCAATGAGCAGATTCTCC |
| 1608 | PKA-13 | GGTCAATGAGCAGATTC |
| 1609 | PKA-14 | CCCTGCTGGTCAATG |
| 1610 | PKA-15 | TAGCCCTGCTGGTC |
| 1611 | PKA-16 | CGCTTGGCGAAACC |
| 1612 | PKA-17 | CCTTCACGCGCTTG |
| 1613 | PKA-18 | AAGGTCCAAGTGCG |
| 1614 | PKA-19 | TGCCGCACAAGGTC |
| 1615 | IL-12alpha-1 | GGTGAGGACCACCATTT |
| 1616 | IL-12alpha-2 | GGGTGTCACAGGT |
| 1617 | IL-12alpha-3 | ATACCATCTTCTTCAGGG |
| 1618 | IL-12alpha-4 | GGTGATACCATCTTCTTC |
| 1619 | IL-12alpha-5 | CCAGGTGATACCATCTTC |
| 1620 | IL-12alpha-6 | CCTCACTGCTCTGGT |
| 1621 | IL-12alpha-7 | TAAGACCTCACTGC |
| 1622 | IL-12alpha-8 | CAGAGCCTAAGACCTC |
| 1623 | IL-12alpha-9 | CCAGAGCCTAAGACC |
| 1624 | IL-12alpha-10 | TCTTCCTTTTTGTGAAGC |
| 1625 | IL-12alpha-11 | GACCAAATTCCATCTTCC |
| 1626 | IL-12alpha-12 | ATCAGTGGACCAAATTCC |
| 1627 | IL-12alpha-13 | GGTTCTTTCTGGTCCTTT |
| 1628 | IL-12alpha-14 | TTTTTGGGTTCTTTCTGG |
| 1629 | IL-12alpha-15 | GGTCTTATTTTTGGGTTC |
| 1630 | IL-12alpha-16 | AATGGGCAGACTCTCCT |
| 1631 | IL-12alpha-17 | TCCACCATGACCTCAATG |
| 1632 | IL-12alpha-18 | AACGGCATCCACCATG |
| 1633 | IL-12alpha-19 | GTGAACGGCATCCAC |
| 1634 | IL-12alpha-20 | ACTTGAGCTTGTGAACGG |
| 1635 | IL-12alpha-21 | TTCATACTTGAGCTTGTG |
| 1636 | IL-12alpha-22 | CTGGTGTAGTTTTCATAC |
| 1637 | IL-12alpha-23 | AGCTGCTGGTGTAGTTTT |
| 1638 | IL-12beta-1 | AGGAGGACCAGGGT |
| 1639 | IL-12beta-2 | AGGTGGTCCAGGAG |
| 1640 | IL-12beta-3 | TTTCTGGCCAAACTGAGG |
| 1641 | IL-12beta-4 | GGAGGTTTCTGGCC |

FIG. 5-10

| | | |
|---|---|---|
| 1642 | IL-12beta-5 | TCTGGAGTGGCCAC |
| 1643 | IL-12beta-6 | CTTCTGGAGCATGTTGCT |
| 1644 | IL-12beta-7 | GCCTTCTGGAGCATG |
| 1645 | IL-12beta-8 | GTTTGTCTGGCCTTCTG |
| 1646 | IL-12beta-9 | GAGTTTGTCTGGCCTTCT |
| 1647 | IL-12beta-10 | CTAGAGTTTGTCTGGCCT |
| 1648 | IL-12beta-11 | GCAAGGGTAAAATTCTAG |
| 1649 | IL-12beta-12 | AGTGCAAGGGTAAAATTC |
| 1650 | IL-12beta-13 | AAACAGGCCTCCACT |
| 1651 | IL-12beta-14 | CTTGGTTAATTCCAATGG |
| 1652 | IL-12beta-15 | AGGCAACTCCCATTAGTT |
| 1653 | IL-12beta-16 | TACTACTAAGGCACAGGG |
| 1654 | IL-12beta-17 | AATACTACTAAGGCACAG |
| 1655 | IL-12beta-18 | GTACATCTTCAAGTCTTC |
| 1656 | Pg-R | GGAGTGGACATGAT |
| 1657 | thr | AAGAAGATGAAGCCTTTG |
| 1658 | ref-fosjun | CCGTCTTACTCTTCTTGG |
| 1659 | PIV | CCGATACAATTCCAAGG |
| 1660 | PIV | CCTTTTCCTTCTGAG |
| 1661 | PIV | CTGTTGCAAGTACG |
| 1662 | bak | CAGAAGCAGAGGGC |
| 1663 | bak | CCTCAGAAGCAGAGG |
| 1664 | bak | CTCCTCAGAAGCAG |
| 1665 | bak | ACAGGCTGGTGGCA |
| 1666 | bak | CCACTCTCAAACAGGC |
| 1667 | bak | ACGGTAGCCGAAGC |
| 1668 | bak | GACGGTAGCCGAAGC |
| 1669 | bak | GGCCAGACGGTAGC |
| 1670 | bak | GTGTAGGGCCAGACGGTA |
| 1671 | bak | CCGAAGCCATTTTTCAGG |
| 1672 | bak | CCCCGAAGCCATTTTTC |
| 1673 | bak | GGTTGATGTCGTCC |
| 1674 | bak | GCTTGAGACACTCGC |
| 1675 | bak | CCGGACCCGTCCAT |
| 1676 | bclx | GCTTGCTTTACTGC |
| 1677 | bclx | GGTTGCTCTGAGAC |
| 1678 | bclx | GCCACAGTCATGCC |
| 1679 | bmp | CGGGCATGCTGGCG |
| 1680 | bmp | GTGAAGTTCAGGATGATC |
| 1681 | bmp | CCAGTGCCTCATGG |
| 1682 | ICE | CAGTGTTCTCCATGG |

FIG. 5-11

| | | |
|---|---|---|
| 1683 | ICE | CTGTACCAGACCGAG |
| 1684 | ICE | GCATACTGTTTCAGC |
| 1685 | ich | GCCATCAGCTCCTTG |
| 1686 | ich | CCACACCATAGATGG |
| 1687 | ich | GCTGGAGCAGTTTCC |
| 1688 | bcl1 | CTCGCTTCTGCTGC |
| 1689 | bcl2 | ACCGTGGCAAAGCG |
| 1690 | mucrep | AGGTGACACCGTGG |
| 1691 | AHR | GACTTGATTCCTTCAG |
| 1692 | AHR | GGATTTGACTTGATTCC |
| 1693 | AHR | GCTGCTGTTCATGG |
| 1694 | CD2 | CCGTTTCTTTCAGTAGG |
| 1695 | MEK2 | CTTGAAGTAGGAGC |
| 1696 | tnf | CGCTCCTACATGGC |
| 1697 | tnf | GATGAGGTACAGGCC |
| 1698 | tnf | GTAGATGAGGTACAG |
| 1699 | tnf | GAGTAGATGAGGTAC |
| 1700 | tnf | CCTGGGAGTAGATG |
| 1701 | tnf | GGACCTGGGAGTAG |
| 1702 | tnf | ACATGGGTGGAGGG |
| 1703 | tnf | GTGCTCATGGTGTC |
| 1704 | tnf | CTTTCAGTGCTCATG |
| 1705 | tnf | TGCTTTCAGTGCTCA |
| 1706 | tnf | GATGATCTGACTGCC |
| 1707 | tnf | GTTCGAGAAGATGATC |
| 1708 | tnf | GGGTTCGAGAAGATG |
| 1709 | tnf | GGTTTGCTACAACATG |
| 1710 | tnf | CAGCTTGAGGGTTTG |
| 1711 | tnf | TGCCCCTCAGCTTG |
| 1712 | TNFR | GACACACACTATCTC |
| 1713 | IL-18 | GCAGCCATCTTTATTC |
| 1714 | IL-18 | GTTCAGCAGCCATC |
| 1715 | IL-18 | TGGTTCAGCAGCCA |
| 1716 | IL-18 | CTACTGGTTCAGCAGC |
| 1717 | IL-18 | TCTACTGGTTCAGC |
| 1718 | IL-18 | GCCACAAAGTTGATGC |
| 1719 | IL-18 | CATTGCCACAAAGTTG |
| 1720 | IL-18 | GAGAACTTGGTCATTC |
| 1721 | IL-18 | GGTCAATGAAGAGAAC |
| 1722 | IL-18 | CGATTTCCTTGGTC |
| 1723 | IL-18 | CCGATTTCCTTGGTC |

FIG. 5-12

| | | |
|---|---|---|
| 1724 | IL-18 | CAAATAGAGGCCGATTTC |
| 1725 | IL-18 | CAAATAGAGGCCGA |
| 1726 | IL-18 | CCTCTAGGCTGGCT |
| 1727 | IL-18 | CATACCTCTAGGCTG |
| 1728 | IL-18 | AGCCATACCTCTAG |
| 1729 | IL-18 | CAGCCATACCTCTAG |
| 1730 | IL-18 | CACAGAGATAGTTACAG |
| 1731 | IL-18 | GTCTTCGTTTTGAACAG |
| 1732 | IL-18 | CTAGTCTTCGTTTTGAAC |
| 1733 | IL-18 | TAGCTAGTCTTCGTTTTG |
| 1734 | IL-18 | GAGCCACTGCGCC |
| 1735 | IL-18 | CGTGAGCCACTGCG |
| 1736 | IL-12-Rec | CGTAACGATCACTGG |
| 1737 | IL-12-Rec | GCACTCGTAACGATC |
| 1738 | IL-12-Rec | GGAGCACTCGTAAC |
| 1739 | IL-12-Rec | CATCATCCTGAGGT |
| 1740 | IL-12-Rec | CAGTATCATCATCCTG |
| 1741 | IL-12-Rec | CTCAGTATCATCATCC |
| 1742 | IL-12-Rec beta2 | CTAAAAGTATGTGCCATC |
| 1743 | IL-12-Rec beta2 | CACATCGCCTCTCT |
| 1744 | IL-12-Rec beta2 | GCTTCACAGTCACATCGC |
| 1745 | IL-12-Rec beta2 | GGAAGGCTTCACAGTC |
| 1746 | IL-12-Rec beta2 | CCTGTGACTTGAGAATTG |
| 1747 | IL-12-Rec beta2 | GGAAGACCTGTGAC |
| 1748 | IL-12-Rec beta2 | CTCTGCTCCACATATTTG |
| 1749 | IL-12-Rec beta2 | CAACGAAGATCTCTG |
| 1750 | IL-12-Rec beta2 | CAACACCAACGAAG |
| 1751 | PKC-beta | GGTCTTCTGTTTGC |
| 1752 | CB-1-Rec | CGATGAAGTGGTAGGAAG |
| 1753 | TGF-alpha | GGTTGCATGGAAGC |
| 1754 | Fascin | GGTCACAAACTTGCC |
| 1755 | p300 | CTGATTTGGTCCACTAG |
| 1756 | CBP | CATGTTAGCACTGTTC |
| 1757 | rac-alpha | GGTCTTGATGTACTCC |
| 1758 | EBV | CCACCTAAAGAGAGATC |
| 1759 | HSPQ | CTTGTACTGCACCATC |
| 1760 | CC-CKR1 | GCCAGTTAAGAAGATG |
| 1761 | CC-CKR4 | GAGATCATGATCCATGG |
| 1762 | c-CRK | GTAGTGTCCCAATAGTG |
| 1763 | c-CRK | CTTCCTCATCATTCCC |
| 1764 | CRKL | CACAAGCTTTTCGAC |

ANTISENSE OLIGONUCLEOTIDE PREPARATION METHOD

This is a divisional of application Ser. No. 09/341,700, filed Sep. 24, 1999 now U.S. Pat. No. 6,972,171, which is a 371 of PCT/EP 09/00497, filed Jan. 30, 1998, the disclosure of each of the foregoing being incorporated by reference herein.

The present invention is related to a method for the preparation of antisense oligonucleotides and to an oligonucleotide or functional or structural analogs or effective derivatives thereof, forming hydrogen bonds with deoxyribonucleic acids (DNA) and/or ribonucleic acids (RNA) or derivatives thereof including, but not limited to the formation of hydrogen bonds with the bases adenine (A), cytosine (C), guanine (G), uracil (U) or thymidine (T) contained in such molecules or forming hydrogen bonds with residues of a particular protein, such a molecule being capable of altering the expression structure or function, of a gene, an RNA molecule or a protein or altering the level of activity of a gene, an RNA molecule or a protein. Furthermore, the present invention is related to such nucleic acid or functional or structural analogs or effective derivatives thereof, coupled or mixed with folic acid, hormones, steroid hormones such as oestrogen, progesterone, corticosteroids, mineralocorticoids, androgens, peptides, proteoglycans, phospholipids, glycolipids and derivatives therefrom.

Furthermore, the invention is related to the use of said nucleic acids or functional or structural analogs or effective derivatives thereof, for analyzing the functional properties of a particular gene, RNA, or protein by altering its activity, structure, function or altering its expression levels.

Furthermore, the invention is related to antisense nucleic acids, capable of modulating the expression or functional activity of proteins which regulate cell growth leading to augmentation, inhibition or modulation of cell-growth or cell proliferation and/or the expansion of primary cells or stem cells, e.g. in culture or in the living organism.

Furthermore, the invention is related to a pharmaceutical composition comprising said nucleic acids or functional or structural analogs or effective derivatives thereof, hybridizing with an area of the messenger RNA (mRNA) or the DNA of a target gene or binding to a particular protein as well as the use of said nucleic acids, structural analogs and derivatives thereof for the manufacturing of a pharmaceutical composition for the treatment of diseases where the alteration of the structure function, activity or expression of a particular target gene, a particular target RNA or a particular target proteins activity leads to a therapeutic benefit related to the effect of the nucleic acid or derivative thereof.

Modulation of the expression of genes, RNA molecules or proteins or of their activity levels with nucleic acids or functional or structural analogs or effective derivatives thereof is a powerful means to study the function of the respectivemolecules. For example modulation, e.g. knockdown or increase of the expression of a particular protein can lead to the identification of its physiological as well as its pathophysiological roles in cultured cells as well as in living organisms in vivo.

Furthermore, the aberrant expression or overexpression of genes, RNA molecules or proteins, the expression of foreign DNA, RNA or proteins e.g. derived from infectious organisms or the expression of mutated DNA, RNA and proteins is found in a variety of diseases. Downregulation of the expression or the activity of such DNA, RNA and/or proteins can lead to an inhibition of or to the reversal of pathological processes in which the expression of a particular DNA, RNA and/or protein plays a role. However, nucleic acids or derivatives thereof used for downregulation of DNA, RNA and/or protein expression are often ineffective and/or toxic to the cells or the organisms treated with such molecules.

An object of the present invention is to provide a method for designing and preparation of oligonucleotides or derivatives thereof which avoid the drawbacks of prior art, and give a reliable method for preparation of oligonucleotides having increased effectivity and/or reduced toxicity and/or reduced non-selective effects.

The object is attained by a method having the features of claims 1. Preferred embodiments of the method of the invention are those according to claims 2 to 7.

BRIEF DESCRIPTION OF THE DRAWINGS

FIG. 3 shows TGF-β1 antisense sequences according to the invention as well as sequences from Hatzfeld et al. (H) and N1-N39.

FIG. 4 shows oligonucleotides of prior art.

FIG. 5 shows antisense oligonucleotides (sequences 1273-1764) according to the invention.

Figure 1:
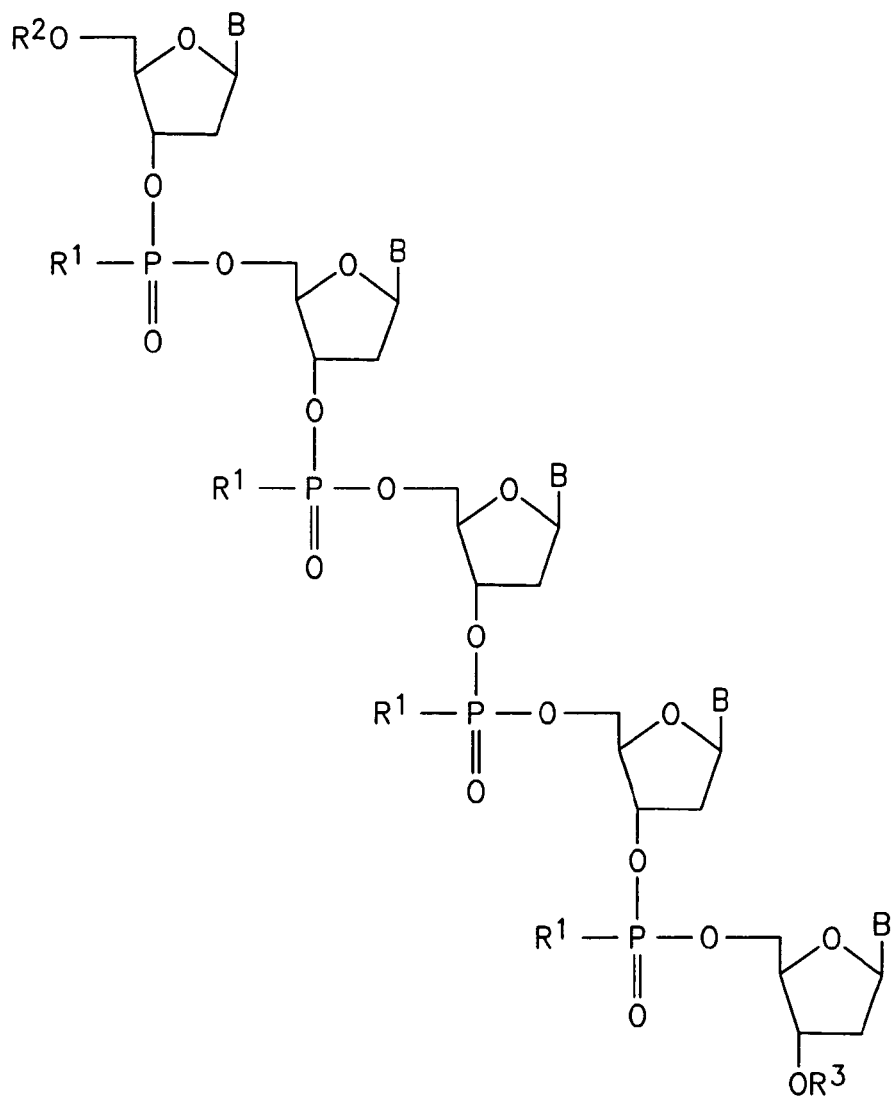
FIG. 1 shows the chemical structures of antisense oligodeoxy-ribonucleotides.
Figure 1:
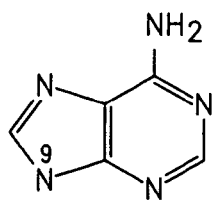
Figure 1:
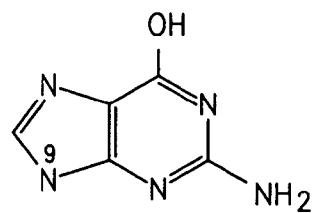
Figure 1:
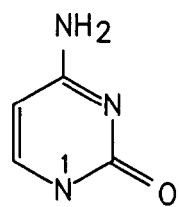
Figure 1:
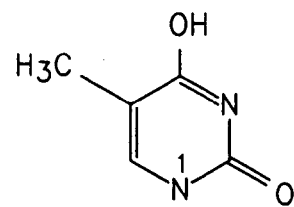

The method of the invention comprises the steps
of selecting a target nucleic acid, if necessary elucidating its sequence
generating the antisense oligonucleotide with the proviso that
the oligonucleotide comprises at least 8 residues,
the oligonucleotide comprises at maximum twelve elements, which are capable of forming three hydrogen bonds each to cytosine bases,
the oligonucleotide does not contain four or more consecutive elements, capable of forming three hydrogen bonds each with four consecutive cytosine bases (CCCC) within the target molecule or alternatively four or more consecutive elements of GGGG,
the oligonucleotide does also not contain 2 or more series of three consecutive elements, capable of forming three hydrogen bonds each with three consecutive cytosine bases (CCC) within the target molecule, or alternatively 2 or more series of three consecutive elements of GGG, and
the ratio between residues forming two hydrogen bonds per residue (2H-bond-R) with the target molecule and those residues forming three hydrogen bonds per residue (3H-bond-R) with the target molecule, is ruled by the following specifications:

$$\frac{\text{3H-bond-R}}{\text{3H-bond-R} + \text{2H-bond-R}} \geq 0.29$$

and synthesizing the oligonucleotide thus generated in a per se known manner.

The generated antisense oligonucleotide comprises at least 8 residues in order to have sufficient interaction with the target molecule and has preferably up to 30, more preferably up to 24 or most preferred up to 18 residues. Shorter chain length are preferred over longer ones to increase specificity and/or reduce non-specific effects.

The oligonucleotide comprises at maximum 12 elements which are capable of forming 3 hydrogen bonds each to cytosine bases. In case of generating an oligonucleotide an element is represented by a residue, thus a nucleotide of the oligonucleotide. In cases of generating a derivative an element is considered as a part of the molecule capable of forming hydrogen bonds. It is preferred that the oligonucleotide comprises at maximum 10 and more preferred at maximum 8 elements which are capable of forming 3 hydrogen bonds each to cytosine bases.

The generated antisense oligonucleotide preferably does not contain 4 or more consecutive guanine bases and does also not contain 2 or more series of 3 consecutive guanine bases.

Preferably, the ratio between residues forming 2 hydrogen bonds per residue (2H-bond-R) with their target molecule and those residues forming 3 hydrogen bonds per residue (3H-bond-R):

$$\frac{\text{3H-bond-R}}{\text{3H-bond-R} + \text{2H-bond-R}}$$

is in the range of greater than 0.33 and smaller than 0.86, more preferably smaller than 0.79 and still more preferred smaller than 0.72.

In one embodiment the oligonucleotides generated by the method of the invention are modified for higher nuclease resistance than naturally occurring nucleotides. Methods for synthesizing oligonucleotides and derivatives thereof are known in the art, see for example "Oligonucleotides and Analogues", F. Eckstein (Ed.), 1991, IRL Press Oxford or "Protocols for Oligonucleotides and Analogs, Synthesis and Properties", Sudhir Agrawal (Ed.), 1993, Humana Press, Totowa, N.J.

Oligonucleotides of the invention may also contain RNA and DNA residues within their chains.

The modifications can be made to the bases, the sugars or the linkages of the oligonucleotides. Preferably, the modifications are phosphorothioate (S-ODN) internucleotide linkages, and/or methylphosphonate internucleotide linkages, N'3→P5' phosphoramidate linkages, peptide linkages or 2'-methoxyethoxy modifications of the sugar moiety or modifications of the bases. In a preferred embodiment the oligonucleotide has at least two different types of modifications and more preferably at least two different types of internucleotide linkages. In another preferred embodiment the oligonucleotides are linked to or mixed with folic acid, hormones such as steroid hormones or corticosteroids, peptides, proteoglycans, glycolipids, phospholipids or derivatives thereof.

Surprisingly the molecules, obtainable according to the method of the invention could strongly reduce or avoid toxicity and/or non-specific effects of such molecules and/or had significantly higher activity than sequences selected otherwise. Preferably, the molecules according to the invention have the following features: They do not contain four or more consecutive guanosine ($N_aGGGGN_b$) or inosine ($N_aIIIIN_b$) residues and the oligonucleotide does not contain two or more series of three or more consecutive guanosine residues ($N_aGGGN_cGGGN_b$) and does not contain two ore more series of three or more consecutive inosine residues ($N_aIIIN_cIIIN_b$), wherein $N_a$, $N_b$, $N_c$ represent independently oligonucleotides of any sequence having 0 to 20 residues.

In a preferred embodiment the molecule contains a minimum of 10 residues capable of forming either two or three hydrogen bonds per residue. Furthermore, the molecule contains a maximum of 24 consecutive residues linked by phosphorothioate linkages capable of forming either two or three hydrogen bonds per residue. In molecules according to the invention which contain more than 18 residues the additional linkages preferably consist of methylphosphonate linkages or phosphodiester linkages.

The chemical structures of antisense oligodeoxy-ribo-nucleotides are given in FIG. 1.

Figure 2:
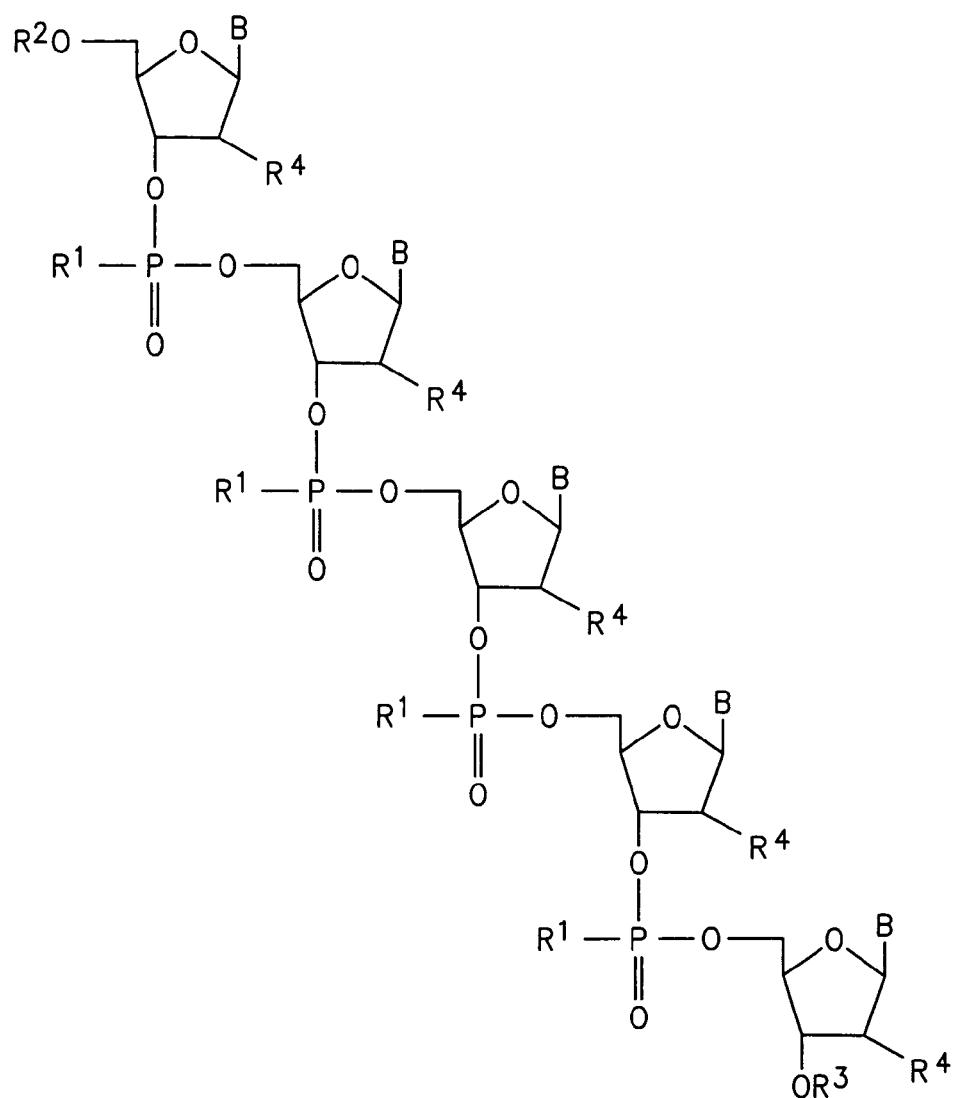
FIG. 2 shows the chemical structures of antisense oligoribonucleotides.
Figure 2:
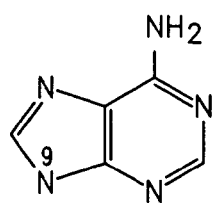
Figure 2:
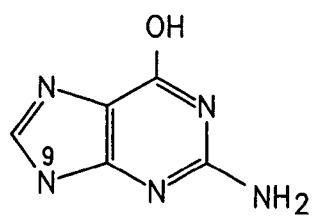
Figure 2:
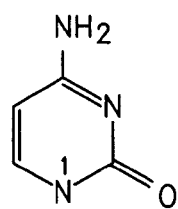
Figure 2:
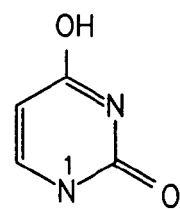

The chemical structures of antisense oligo-ribonucleotides are given in FIG. 2. The oligonucleotide is to be understood as a detail out of a longer nucleotide chain.

Of course, the oligonucleotides may be composed of elements of either figures.

In FIGS. 1 and 2, lit. B means an organic base such as adenine (A), guanine (G), cytosine (C), inosine (I), uracil (U) and thymine (T) which are coupled to the deoxyribose. The linkages between the nucleotides are either phosphodiester bonds as in naturally occurring DNA or linkages spacing the nucleotides in such a way to allow hybridization with its target nucleic acid or binding to a protein in order to regulate its activity, such as e.g. phosphorothioate linkages, methylphosphonate linkages, phosphoramidate linkages or peptide linkages.

$R_2$ and $R_3$ represent further residues of the oligonucleotide or derivative.

$R_4$ represents OH or a modification such as a 2'-methoxy ethoxy derivative.

The modifications of the phosphodiester linkage, shown in FIGS. 1 and 2 can be selected from, but are not limited to.

1. Oligodeoxy-ribonucleotides or oligoribonucleotides substituted by 1.1 R1=O 1.2 R1=S 1.3 R1=F 1.4 R1=$CH_3$ 1.4 R1=OEt 2. Oligodeoxy-ribonucleotides where R1 is varied at the internucleotide phosphates within one oligonucleotide

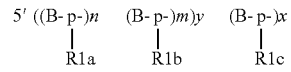

where lit. p stands for the phosphodiester or the phosphoramidate linkage, modified by coupling to R1a, R1b or R1c or for a peptide linkage, or for linkages spacing the nucleotides in such a way to allow hybridization with its target nucleic acid or binding to a protein in order to regulate its activity, structure, function or expression level.

where lit. B=any deoxy-ribonucleotide or ribonucleotide, depending on gene sequence according to the invention.

n, m, x, y=integers 0-20

Preferred maximal length of the total number of bases is 30.

| 2.1 | $R_{1a}$ = S | $R_{1b}$ = $CH_3$ | $R_{1c}$ = S |
| --- | --- | --- | --- |
| 2.2 | $R_{1a}$ = S | $R_{1b}$ = $CH_3$ | $R_{1c}$ = O |
| 2.2 | $R_{1a}$ = S | $R_{1b}$ = O | $R_{1c}$ = S |
| 2.2 | $R_{1a}$ = S | $R_{1b}$ = O | $R_{1c}$ = $CH_3$ |
| 2.3 | $R_{1a}$ = $CH_3$ | $R_{1b}$ = S | $R_{1c}$ = $CH_3$ |
| 2.4 | $R_{1a}$ = $CH_3$ | $R_{1b}$ = S | $R_{1c}$ = O |
| 2.5 | $R_{1a}$ = $CH_3$ | $R_{1b}$ = O | $R_{1c}$ = $CH_3$ |

-continued

| | | | |
|---|---|---|---|
| 2.6 | $R_{1a} = CH_3$ | $R_{1b} = O$ | $R_{1c} = S$ |
| 2.7 | $R_{1a} = O$ | $R_{1b} = S$ | $R_{1c} = O$ |
| 2.8 | $R_{1a} = O$ | $R_{1b} = S$ | $R_{1c} = CH_3$ |
| 2.9 | $R_{1a} = O$ | $R_{1b} = CH_3$ | $R_{1c} = O$ |
| 2.10 | $R_{1a} = O$ | $R_{1b} = CH_3$ | $R_{1c} = S$ |

Preferably, the oligonucleotide comprises a minimum of 10 elements and a maximum of 24 elements capable of forming either 2 or 3 hydrogen bonds per element. The oligonucleotides of the invention can have modifications to the base, the sugar or the phosphate moiety. Preferred modifications are phosphorothioate (S-ODN) internucleotide linkages, and/or methylphosphonate internucleotide linkages, N'3→P5' phosphoramidate linkages, peptide linkages or 2'-methoxyethoxy modifications of the sugar or modifications of the bases. In a very preferred embodiment the antisense oligonucleotides comprise the sequences 41 to 73, 74 to 106, 154 to 172, 173 to 203, 298 to 380, 476 to 506, 519 to 556 and 597 to 641 of FIG. 3 and 1273-1764 of FIG. 5. A further aspect of the invention is the use of the oligonucleotides of the invention for the inhibition of the genes p53, rb, junD, junB, TGF-β1, TGF-β2 to influence cell proliferation, in particular of primary cell cultures such as liver cells, kidney cells, osteoclasts, osteoblasts and/or keratinocytes and/or cells of the blood lineage, such as bone marrow stem cells, and/or progenitor cells of red and white blood cells and/or organ stem cells.

The Sequences 41-73 and/or 74-106 and/or 154-203 and/or 519-556 and/or 597-641 and/or 1273-1277 and/or 1481-1490 and/or 1532-1549 and/or 1656 are useful for the treatment and/or prevention of immunosuppressive disorders including, but not limited to immunosuppression in neoplastic diseases—including gliomas and other brain tumors, sarcomas, carcinomas and lymphomas—and/or immunosuppression as side effect from drugs, including, but not limited to side effects from cytotoxic agents and/or immunosuppression in AIDS patients.

In a further embodiment of the invention these sequences are also useful for the treatment and/or prevention of hyoproliferation of normal cells, including, but not limited to immune cells, bone marrow stem cells, endothelial cells, organ stem cells and proliferating cells of the intestine.

The Sequences 41-73 and/or 74-106 and/or 298-380 and/or 476-506 and/or 519-556 and/or 1273-1480 and/or 1596-1614 and/or 1657-1658 and/or 1690 and/or 1696-1712 and/or 1751 and/or 1753-1754 and/or 1757 are useful for the treatment and/or prevention of hyperproliferative disorders, including but not limited to brain tumors, sarcomas, carcinomas and lymphomas, restenosis, hyperplasia, pulmonary fibrosis, angiogenesis and psoriasis.

The Sequences 1278-1480 and/or 1491-1531 and/or 1582-1595 and/or 1615-1655 and/or 1691-1694 and/or 1697-1750 and/or 1759-1764 are useful for the treatment and/or prevention of diseases characterised by hyperfunction of the immune system and/or of inflammatory disorders and/or autoimmune disorders, including, but not limited to asthma (molecules according to the invention being applied by inhalation and/or by parenteral routes and/or orally), multiple sclerosis, inflammatory disorders of the intestine, including jejunitis, ileitis and/or colitis, as well as inflammatory disorders characterised by hyperproliferation and/or hyperfunction of cells of the eosinophilic lineage and/or glomerulonephritis and/or rejection of transplants.

The Sequences 476-506 and/or 1550-1581 and/or 1582-1595 and/or 1658-1689 and/or 1691-1694 and/or 1713-1752 are useful for the treatment and/or prevention of diseases associated with cell degeneration, including, but not limited to neurodegeneration, e.g. Alzheimer's diseases, Parkinson's, ischemic disorders, including myocardial ischemia and/or ischemia of the nervous system, including stroke.

A further aspect of the present invention is a medicament comprising an oligonucleotide according to the invention together with additives. The oligonucleotides of the invention can be used for the preparation of a medicament for the prevention or the treatment of neoplasm, hypoproliferation, hyperproliferation, degenerative diseases, neurodegenerative diseases, ischaemia, disorders of the immune system and/or infectious diseases and can be used for the analysis of gene function or drug target validation.

Molecules according to the invention can be used to study the function of target molecules and their encoded transcription and/or translation products, including RNA molecules and proteins. Downregulations of a protein or nucleic acid molecule using molecules according to the invention can be used to study the function of the molecule. It is also a feature of the invention that molecules according to the invention can be used to study whether modulation of the product has a desired effect, including therapeutic effects and to use this information to develop a different molecule, in order to modulate the function of the protein.

This includes, for example, drug target validation with a molecule according to the invention, in order to answer the question whether development of an agent capable of modulating the structure, function or expression of a potential target molecule, e.g. an agonist or antagonist of the target molecule has desired effect and may e.g. be of therapeutic or diagnostic use.

It is thus also a feature of the invention that molecules according to the invention can be used for drug target validation, including but not limited to studying whether modulation of a protein or nucleic acid molecule has a desired effect, including therapeutic effects and using this information to develop a compound, e.g. a therapeutic compound capable of modulating the structure, function or expression of the molecule the function of which was previously studied with molecules according to the invention.

EXAMPLE 1

Treatment of Peripheral blood mononuclear cells with TGF-β1 antisense phosphorothioate oligodeoxynucleotides:

Human peripheral blood mononuclear cells (PBMCs) produce transforming growth factor β1 (TGF-β1). The TGF-β1 produced by these cells negatively regulates immune cell proliferation in an autologous manner. This autologous negativeregulation of immune cell proliferation could be reversed by antisense TGF-β1 molecules according to the invention, leading to stimulation of immune cell proliferation. In contrast to the molecules according to the invention, antisense molecules chosen conventionally, including that published by Hatzfeld et al. (1991) did not stimulate immune cell proliferation. Even more surprising, several sequences, chosen conventionally, even reduced immune cell proliferation.

Peripheral blood mononuclear cells (PBMCs) were isolated from venous blood of healthy donors by mixing with an equal volume of RPMI 1640 medium (Gibco) supplemented with 10% fetal calf serum and 1 mM L-glutamine, followed by layering onto Ficoll-Hypaque (Pharmacia) gradients and centrifugation at 400 g for 30 min. PBMCs were removed from the plasma-Ficoll interface and washed in the above medium. Cells ($2 \times 10^4$ in 100 μl of medium) were plated into 96 well flat-bottom microtiter plates (Nunc) in serum supplemented complete medium. Cells were activated with 3 μg/ml phytohemagglutinin and incubated with either no oligodeoxynucleotide (untreated control cells) or with 8 μM of different antisense phosphorothioate oligodeoxynucleotides, complementary to different regions of the human TGF-β1 mRNA for 4 days. Cells were then stained with trypan blue to determine cell viability and counted in a Neubauer counting chamber.

Oligonucleotide sequences were either 33 sequences according to the invention, named sequences TGF-β1-1-TGF-β1-33 (SEQ ID NOS: 41-73) or the TGF-β1 antisense sequence from Hatzfeld et al. (1991), J. Exp. Med., 174, pp. 925-929 or 39 other conventionally chosen antisense sequences complementary to human TGF-1 mRNA, named N1-N39 (see FIG. 3) (SEQ ID NOS: 2-40).

Surprisingly the molecules according to the invention were much more effective than antisense TGF-β1 molecules that were chosen conventionally.

Sequences TGF-β1-1-TGF-β1-33 (SEQ ID NOS: 41-73) (see FIG. 3) enhanced lymphocyte proliferation to between 135 and 213% of untreated controls. In contrast, treatment with the antisense sequence from document Hatzfeld et al. reduced proliferation to 62.8%.

Cells treated with the conventionally chosen TGF-β1 antisense sequences N1-N39 (SEQ ID NOS: 2-40) surprisingly not only failed to increase lymphocyte proliferation, but several of these sequences even revealed a marked inhibition of cell proliferation to between 51.4% and 77% of controls (sequences N1-N14 (SEQ ID NOS: 2-15), N20 (SEQ ID NO: 21), N26 (SEQ ID NO: 27) and N30-N39 (SEQ ID NOS: 31-40). The antisense TGF-β1 sequences N15-N19 (SEQ ID NOS: 16-20), N21 N25 (SEQ ID NOS: 22-26), N28 (SEQ ID NO: 29) and N29 (SEQ ID NO: 30) showed neither significant enhancement nor significant inhibition of cell proliferation with values between 94% and 103%. Sequence N27 (SEQ ID NO: 28) showed slight toxicity with a reduction in cell proliferation to 88%.

Inhibition of cell proliferation by some of the TGF-1 sequences suggests that they may not be merely ineffective, but also toxic. Analysis of the 26 sequences N-N14 (SEQ ID NOS: 2-15), N20 (SEQ ID NO: 21), N26 (SEQ ID NO: 27) and N30-N39 (SEQ ID NOS: 31-40) revealed that 23 of them contained either 2 or more sequence motifs with three consecutive Gs (hereafter called CCC motif) or at least one motif with 4, 5, or 6Gs (motifs GGGG, GGGGG, or GGGGGG). Analysis of the sequence from Hatzfeld et al., which also inhibited PBMC proliferation, surprisingly showed that it too contains a GGGGG plus a CCC motif. The 3 toxic sequences that contained neither 2CCC motifs nor a motif of 4 or more consecutive Gs, i.e. sequences N8 (SEQ ID NO: 9), N26 (SEQ ID NO: 27) and N35 (SEQ ID NO: 36) were found have a base content with 11-13 G-bases per sequence.

In contrast to the sequences from Hatzfeld et al., N1-N14 (SEQ ID NOS: 2-15), N20 (SEQ ID NO: 21), N26 (SEQ ID NO: 27) and N30-N39 (SEQ ID NOS: 31-40) the sequences TGF-β1-1-TGF-β1-33-showed a G-content of maximally 6 G-bases, no combination of two CCC motifs within a single sequence and no GGGG, GGGGG or GGGGGG motif. Since the TGF-β1-mRNA contains more than 85 target regions for a CCC antisense motif and more than 34 target regions for a GGGG antisense motif, this finding in the sequences according to the invention was highly unlikely on a statistical basis.

The non-effective sequences N15-N19 (SEQ ID NOS: 16-20), N21-N25 (SEQ ID NOS: 22-26), N28 (SEQ ID NO: 29) and N29 (SEQ ID NO: 30) were found to contain a different base content from both the toxic and the effective sequences: They content of the bases A and T taken together (A/T-content) ranged from 14.3% to 28.5%. These sequences neither enhanced nor did they inhibit PBMC proliferation. Thus, they appeared to be neither effective nor toxic. In contrast to these non-effective sequences with an ALT content of 14.3 k-28.5%, the effective sequences TGF-β1-1-TGF-β1-33 (SEQ ID NOS: 41-73) were found to have an A/T content of between 33%-71.4%.

A further difference between the sequences of the invention and two thirds of the other sequences was found with respect to non-specific protein binding: Sequences from document Hatzfeld et al. and N1-N14 (SEQ ID NOS: 2-15), N20 (SEQ ID NO: 21), N26 (SEQ ID NO: 27) and N30-N39 (SEQ ID NOS: 31-40) were found to show markedly enhanced non-specific protein binding compared to the sequences of the invention.

Sequences from Hatzfeld et al. (H) and N1-N39 (SEQ ID NOS: 2-40) are shown in FIG. 3 as well as TGF-β1 antisense sequences according to the invention.

The finding that, while the sequences TGF-β1-1-TGF-β1-33 (SEQ ID NOS: 41-73) stimulated proliferation of PBMC immune cells, the sequence from Hatzfeld et al. and sequences N1-N39 (SEQ ID NOS: 2-40) where either non-effective with little alteration in PBMC proliferation or had toxic effects and inhibited PBMC proliferation was extended to further antisense sequences both of TGF-β2 and other genes as detailed in the following examples 2-7.

The sequences of the oligonucleotides related with TGF-β1 are listed in FIG. 3 for the sake of ease of readability.

For certain applications, including, but not limited to application in dividing cells, including tumor cells, nucleic acid or functional or structural analogs or effective derivatives thereof according to the invention were coupled to folic acid, either at one of the carboxy-groups or at one of the nitrogen atoms of the folic acid.

Furthermore, for certain applications, nucleic acid or functional or structural analogs or effective derivatives thereof according to the invention are mixed with and/or coupled to hormones, steroid hormones such as oestrogen, progesterone, corticosteroids, mineralocorticoids, androgens, phospholipids, peptides, proteoglycans, glycolipids and derivatives therefrom. Preferably, a coupling occurs at $R^2$ and/or $R^3$ of FIGS. 1 and 2.

EXAMPLE 2 p53 antisense nucleic acids (FIG. 3 shows the respective oligonucleotides)

p53 is a tumor suppressor gene that negatively regulates cell proliferation. Certain mutations in the gene can alter the function of p53 in such a way that it becomes an oncogene. The effects of p53 antisense oligodeoxynucleotides on cells containing wild type p53 was analyzed and subsequently also the effect of these sequences on cells with mutated p53.

In cells with wild type p53 effective antisense nucleic acids will lead to downregulation of the wild type p53 protein and thus to enhanced proliferation of the treated cells. Molecules according to the invention are named p53-1-p53-33. Noneffective p53 antisense sequences were named p53-N-1-p53-N-18. Toxic sequences, which inhibited proliferation instead of enhancing it as do effective p53 antisense sequences were named p53-T-1-p53-T-29.

Normal human fibroblasts were grown in RPMI medium supplemented with 5% fetal calf serum (FCS) and 2500 cell/well were plated into 96-well microtiter plates. Antisense phosphorothioate oligodeoxynucleotides were added at 2 μM concentration after 2 h.

Two assays to determine cell proliferation were performed:
To determine 3H-thymidine incorporation, cells were incubated before harvesting with 0.15 µCi 3H-thymidine/well for 6 h. Cells were lysed by freezing, spotted onto glass filters and the amount of incorporated tritium was determined by liquid scintillation counting.
To determine cell number, cells were stained with trypan blue and counted in a Neubauer counting chamber.

Surprisingly, only treatment of cells with antisense sequences according to the invention (p53-1-p53-33) (SEQ ID NOS: 74-105) resulted in an increase in thymidine incorporation to between 3- and 9 fold.

In contrast, treatment with noneffective sequences (p53-N-1 p53-N-18) (SEQ ID NOS: 107-124) did not result in significant alterations in thymidine incorporation.

Furthermore, treatment with toxic antisense p53 sequences (p53-T-1-p53-T-29) resulted (SEQ ID NOS: 125-153) in a decrease in proliferation instead of an increase.

In summary, the 33 antisense sequences according to the invention resulted in effective downregulation of negative growth control by p53 and increased cell proliferation, while the 47 other antisense sequences had either no significant effect on cell proliferation or even suppressed cell proliferation.

EXAMPLE 3 junB antisense nucleic acids (FIG. 3 shows the respective oligonucleotides)

junB and junD, two genes encoding transcription factors of the jun gene family are negative regulators of cell growth, like p53. The effects of different junB and junD antisense oligodeoxynucleotides was analyzed.

Effective junB and JunD antisense nucleic acids will lead to down regulation of the JunB an JunD proteins respectively and thus to enhanced proliferation of the treated cells. Antisense molecules according to the invention are named JunB-1-JunB-19 (SEQ ID NOS: 154-172) and JunD-1-JunD-31 (SEQ ID NOS: 173-203). Noneffective junB antisense sequences were named JunB-N-1-JunB-N-57 (SEQ ID NOS: 204-206). Toxic sequences, which inhibited proliferation instead of enhancing it were named JunB-T-1-JunB-T-20 (SEQ ID NOS: 261-280) and JunD-T-1-JunD-T-17 (SEQ ID NOS: 281-297).

Normal human fibroblasts were grown in RPMI medium supplemented with 5% fetal calf serum (FCS) and 2500 cell/well were plated into 96-well microtiter plates. Antisense phosphorothioate oligonucleotides were added at 2 µM concentration after 2 h.

Two assays to determine cell proliferation were performed:
To determine 3H-thymidine incorporation, cells were incubated before harvesting with 0.15 µCi 3H-thymidine/well for 6 h. Cells were lysed by freezing, spotted onto glass filters and the amount of incorporated tritium was determined by liquid scintillation counting.
To determine cell number, cells were stained with trypan blue and counted in a Neubauer counting chamber.

Surprisingly, again only treatment of cells with anti sense sequences according to the invention (JunB-1-JunB-19 (SEQ ID NOS: 154-172) and JunE1-JunD31 (SEQ ID NOS: 173-203) resulted in an increase in thymidine incorporation to between 2- and 7-fold.

In contrast, treatment with noneffective sequences (JunB-N-1-JunB-N-57) (SEQ ID NOS: 204-260) did not result in significant alterations in thymidine incorporation.

Furthermore, treatment with toxic antisense junB or JunD sequences (JunB-T-1-JunB-T-20 (SEQ ID NOS: 261-280) and JunD-T-1-JunD-T-17 (SEQ ID NOS: 281-297) resulted in a decrease in proliferation instead of an increase.

In summary, the 50 antisense sequences according to the invention resulted in effective downregulation of negative growth control by JunB and JunD, while the 94 other antisense sequences had either no-significant effect on cell proliferation or were even toxic.

EXAMPLE 4

FIG. 3 Shows the Respective Oligonucleotides erbB-2, is a transmembrane molecule with an intracellular tyrosine kinase activity that is amplified and/or overexpressed by carcinoma cells in a variety of neoplasms including breast cancer, lung cancer, oesophageal and gastric cancer, bile duct carcinoma, bladder cancer, pancreatic cancer and ovarian cancer.

In several of these tumors, an amplification and overexpression of the c-erbB-2 gene in the tumor tissue has been shown to correlate with a poor clinical prognosis. Overexpression of p185erbB-2 in non-small-cell lung carcinoma has been shown to impart resistance to a number of chemotherapeutic agents.

Effective erbB-2 antisense nucleic acids will lead to down regulation of the erbB-2 protein and in over-expressing tumor cell lines will lead to reduced cell proliferation of the treated cells. Antisense molecules according to the invention are named erbB-2-1-erbB-2-83 (SEQ ID NOS: 298-380). Noneffective erbB-2 antisense sequences were named erbB-2-N-1-erbB-2-95 (SEQ ID NOS: 381-475). supplemented with 5% fetal calf serum (FCS) and 2500 cell/well were plated into 96-well microtiter plates. Antisense phosphorothioate oligonucleotides were added at 2yM concentration after 2 h.

erbB-2 overexpressing SK-Br-3 human mammary carcinoma cells were grown in RPMI medium supplemented with 5% fetal calf serum (FCS) and 2500 cell/well were plated into 96-well microtiter plates. Antisense phosphorothioate oligonucleotides were added at 2 µM concentration after 2 h.

To determine erbB-2 protein expression cells were harvested with a cell scraper and subjected to ELISA protein determination.

Only treatment of cells with antisense sequences according to the invention (erbB-2-1-erbB-2-83) (SEQ ID NOS: 298-380) resulted in a significant reduction in erbB-2 protein expression by 40-95%.

In contrast, treatment with noneffective sequences (erbB-2-N1-erbB-2-N-95) (SEQ ID NOS: 381-475) did not result in significant alterations in erbB-2 protein expression.

To determine cell number, cells were stained with trypan blue and counted in a Neubauer counting chamber.

Only treatment of cells with antisense sequences according to the invention (erbB-2-1-erbB-2-83) (SEQ ID NOS: 298-380) resulted in a reduction in cell number by 35-70%.

In contrast, treatment with noneffective sequences (erbB-2-N1-erbB-2-N-95) (SEQ ID NOS: 381-475) did not result in significant alterations in cell proliferation.

erbB-2 antisense sequences were shown in FIG. 3-8 to 3-11

EXAMPLE 5

FIG. 3 Shows the Respective Oligonucleotides

The c-fos gene encodes an immediate early gene type transcription factor. Effective c-fos antisense nucleic acids will lead to downregulation of the c-Fos protein.

Antisense molecules according to the invention are named cfos-1-c-fos-31 (SEQ ID NOS: 476-506). Noneffective c-fos antisense sequences were named c-fos-N-1-c-fos-N-12 (SEQ ID NOS: 507-518).

Normal human fibroblasts were grown in RPMI medium supplemented with 5% fetal calf serum (FCS) and 2500 cell/well were plated into 96-well microtiter plates. Antisense phosphorothioate oligonucleotides were added at 2 µM concentration after 2 h.

Expression of the c-Fos protein was determined by ELISA in cell lysates.

Only treatment of cells with antisense sequences according to the invention (c-fos-1-c-fos-31) (SEQ ID NOS: 476-506) resulted in a significant reduction in c-fos protein expression by 45-95%.

In contrast, treatment with noneffective sequences (c-fos-N-1-c-fos-N-12) (SEQ ID NOS: 507-518) did not result in significant alterations in c-Fos protein expression.

EXAMPLE 6

FIG. 3 Shows the Respective Oligonucleotides

TGF-β2, like TGF-β1 is a member of the transforming growth factor-β family of cytokines.

Overexpression of TGF-β1 and TGF-β2 is linked to malignant progression, immunosuppression and escape of the tumors from surveillance by the immune system.

Effective TGF-β2 antisense nucleic acids will lead to downregulation of the TGF-β2 growth-factor.

Antisense molecules according to the invention are named TGF-β2-1-TGF-β2-38 (SEQ ID NOS: 519-556). Noneffective TGF-β2 antisense sequences were named TGF-β2-N-1-TGF-2-N-40 (SEQ ID NOS: 557-596)

TGF-β2 overexpressing tumor cells were grown in RPMI medium supplemented with 5 fetal calf serum (FCS) and 2500 cell/well were plated into 96-well microtiter plates. Antisense phosphorothioate oligonucleotides were added at 2 µM concentration after 2 h.

TGF-β2 protein expression was determined by ELISA, both in the supernatant and in cell lysates.

Only treatment of cells with antisense sequences according to the invention TGF-β2-1-TGF-β2-38 (SEQ ID NOS: 519-556) resulted in a significant reduction in TGF-β2 protein expression by 35-80%.

In contrast, treatment with noneffective sequences TGF-β2-N-1-TGF-β2-N-40 (SEQ ID NOS: 557-596) did not result in significant alterations in TGF-β2 protein expression.

EXAMPLE 7

FIG. 3 Shows the Respective Oligonucleotides rb antisense nucleic acids rb is a tumor suppressor gene that negatively regulates cell proliferation. The effects of rb antisense oligodeoxynucleotides on cells containing wild type rb was analyzed.

In cells with wild type rb effective antisense nucleic acids will lead to downregulation of the wild type rb protein and thus to enhanced proliferation of the treated cells.

Molecules according to the invention are named rb-1-rb-45 (SEQ ID NOS: 597-641).

Noneffective rb antisense sequences were named -1-rb-N168 (SEQ ID NOS: 642-809). Toxic sequences, which inhibited proliferation instead of enhancing it as do effective rb antisense sequences were named rb-T-1-rb-T-16 (SEQ ID NOS: 810-825).

Normal human fibroblasts were grown in RPMI medium supplemented with 5% fetal calf serum (FCS) and 2500 cell/well were plated into 96-well microtiter plates. Antisense phosphorothioate oligonucleotides were added at 2 µM concentration after 2 h.

Two assays to determine cell proliferation were performed:
To determine 3H-thymidine incorporation, cells were incubated before harvesting with 0.15 µCi 3H-thymidine/well for 6 h. Cells were lysed by freezing spotted onto glass filters and the amount of incorporated tritium was determined by liquid scintillation counting.
To determine cell number, cells were stained with trypan blue and counted in a Neubauer counting chamber.

Surprisingly, only treatment of cells with antisense sequences according to the invention (rb-1-rb-45) (SEQ ID NOS: 597-641) resulted in an increase in thymidine incorporation to between 2- and 6-fold.

In contrast, treatment with noneffective sequences (rb-N-1 rb-N-168) (SEQ ID NOS: 642-809) did not result in significant alterations in thymidine incorporation.

Furthermore, treatment with toxic antisense rb sequences (rb-T-1-rb-T-16) (SEQ ID NOS: 810-825) resulted in a decrease in proliferation instead of an increase.

In summary, the 45 antisense sequences according to the invention resulted in effective downregulation of negative growth control by rb and increased cell proliferation, while the 184 other antisense sequences had either no significant effect on cell proliferation or even suppressed cell proliferation.

EXAMPLE 8

Oligonucleotide sequences according to the invention were synthesized with various different backbone modifications: Exemplary results are given below.

For the sequence

```
erbB-2-42: CATCTGGAAACTTCCAGATG    (SEQ ID NO: 339)
```

(SEQ ID NO: 339) the following chemical modifications were tested in erbB-2 overexpressing carcinoma cells:

1. S-ODN erbB-2-42 (i.e. all backbone linkages were thioate modifications).

```
C-pS-A-pS-T-pS-C-pS-T-pS-G-pS-G-pS-A-pS-A-pS-A-pS-
C-pS-T-pS-T-pS-C-pS-C-pS-A-pS-G-pS-A-pS-T-pS-G
```

2. Me-ODN/S-ODN/Me-ODN erbB-2-42 (i.e. Linkages at the 5' and 3' end were methylphosphonate linkages while linkages in the middle were thioate modifications as follows):

```
C-pMe-A-pMe-T-pS-C-pS-T-pS-G-pS-G-pS-A-pS-A-pS-A-
pS-C-pS-T-pS-T-pS-C-pS-C-pS-A-pS-G-pS-A-pMe-T-pMe-
G
```
or
```
C-pMe-A-pMe-T-pMe-C-pS-T-pS-G-pS-G-pS-A-pS-A-pS-A-
pS-C-pS-T-pS-T-pS-C-pS-C-pS-A-pS-G-pMe-A-pMe-T-
pMe-G
```
or

-continued

C-pMe-A-pMe-T-pMe-C-pMe-T-pS-G-pS-G-pS-A-pS-A-pS-

A-pS-C-pS-T-pS-T-pS-C-pS-C-pS-A-pMe-G-pMe-A-pMe-

T-pMe-G or

C-pMe-A-pMe-T-pMe-C-pMe-T-pMe-G-pMe-G-pS-A-pS-A- pS-A-pS-C-pS-T-pS-T-pS-C-pMe-C-pMe-A-pMe-G-pMe-A- pMe-T-pMe-G

3. Me-ODN/S-ODN erbB-2-42 (i.e. Linkages at the 5' end were methylphosphonate linkages while linkages at the 3' were thioate modifications as follows):

C-pMe-A-pMe-T-pMe-C-pMe-T-pMe-G-pMe-G-pMe-A-pMe-A- pMe-A-pS-C-pS-T-pS-T-pS-C-pS-C-pS-A-pS-G-pS-A-pS-

T-pS-G

4. S-ODN/Me-ODN erbB-2-42 (i.e. Linkages at the 5' end were methylphosphonate linkages while linkages at the 3' were thioate modifications as follows):

C-pS-A-pS-T-pS-C-pS-T-pS-G-pS-G-pS-A-pS-A-pS-A- pMe-C-pMe-T-pMe-T-pMe-C-pMe-C-pMe-A-pMe-G-pMe-A- pMe-T-pMe-G

5. Me-ODN erbB-2-42 (i.e. linkages methylphosphonate linkages):

C-pMe-A-pMe-T-pMe-C-pMe-T-pMe-G-pMe-G-pMe-A-pMe-A- pMe-A-C-pMe-T-pMe-T-pMe-C-pMe-C-pMe-A-pMe-G-pMe-A- pMe-T-pMe-G 6. pN/S-ODN/pN erbB-2-42 (i.e. Linkages at the 5' and 3' end were phosphoramidate linkages while linkages in the middle were thioate modifications as follows):

C-pN-A-pN-T-pS-C-pS-T-pS-G-pS-G-pS-A-pS-A-pS-A-pS-

C-pS-T-pS-T-pS-C-pS-C-pS-A-pS-G-pS-A-pN-T-pN-G or

C-pN-A-pN-T-pN-C-pS-T-pS-G-pS-G-pS-A-pS-A-pS-A-pS-

C-pS-T-pS-T-pS-C-pS-C-pS-A-pS-G-pN-A-pN-T-pN-G or

C-pN-A-pN-T-pN-C-pN-T-pS-G-pS-G-pS-A-pS-A-pS-A-pS-

C-pS-T-pS-T-pS-C-pS-C-pS-A-pN-G-pN-A-pN-T-pN-G or

C-pN-A-pN-T-pN-C-pN-T-pN-G-pN-G-pS-A-pS-A-pS-A-pS-

C-pS-T-pS-T-pS-C-pN-C-pN-A-pN-G-pN-A-pN-T-pN-G where pS stands for substitution of one of the non-bridging oxygen atoms of the backbone linkage with a sulfur atom, while pMe stands for substitution of one of the non-bridging oxygen atoms of the backbone linkage with a-methyl group. pN stands for a N3'→P5' phosphoramidate linkage.

Also a combination of linkages (N-pS-N-pO-N-pO-N)$_n$-[pS-N]$_m$ wherein n=1-10 and m=0-6 where N stand for any nucleotide or structural or functional analog or derivative thereof.

While the Me-ODN backbone modification strongly reduced the erbB-2 activity of the erbB-2-42 (SEQ ID NO: 339) sequence to less than 20%, backbone modifications 1.-4. had strong erbB-2 inhibitory capacity with an inhibition of erbB-2 protein expression by between 78% and 89% at 2 µM concentration at 48 h after the beginning of treatment of overexpressing carcinoma cells. While the pure S-ODN had the highest suppression capacity with 89%, the Me-ODN/S-ODN/Me-ODN as well as the Me-ODN/S-ODN and S-ODN/Me-ODN and pN/S-ODN/pN, displayed reduced protein binding and when tested for complement activation, showed reduced complement activation. These characteristics are advantageous for certain applications e.g. intravenous systemic application in vivo.

EXAMPLE 9

Similar effects were obtained when testing other sequences according to the invention with the above backbone modifications.

Inhibition of TGF-beta-1 gene-expression with the effective sequences for TGF-beta-1 according to the invention was highest with S-ODN and the Me-ODN/S-ODN/Me-ODN backbone modifications and lowest with the Me-ODN modification, while protein binding and complement activation were reduced in sequences containing Me-ODN linkages.

EXAMPLE 10

Surprisingly, effectivity of sequences according to the invention was significantly improved in various cell types by coupling nucleic acids according to the invention to folic acid:

erbB-2 inhibitory capacity which was relatively low after 24 h compared to 48 h with an inhibition of erbB-2 protein synthesis by 24-376 was markedly increased by coupling sequences according to the invention to folic acid to 48-62% at 2 µM concentration 24 h after the beginning of treatment of overexpressing carcinoma cells.

Similar effects were achieved by coupling sequences according to the invention to folic acid derivatives including aminopterin and amethopterin.

EXAMPLE 11

Surprisingly, effectivity of sequences according to the invention was strongly improved by coupling oligonucleotides according to the invention to cortisol:

Cellular uptake and inhibitory capacity of sequences according to the invention including sequences for TGF-beta-1, TGF-beta-2, c-fos, p53, erbB-2, rb, c-fos, junB, junD, c-jun, MIP-1 alpha, JAK-2, bcl-2 and were markedly increased by coupling cortisol either to the 3' or 5' hydroxyl groups of oligonucleotide sequences according to the invention.

EXAMPLE 12

Effectivity of sequences according to the invention was also strongly improved in various cell types by coupling nucleic acids according to the invention to or mixing them with other steroid hormones and their derivatives, including oestrogens, anti-oestrogens, prednisone, prednisolone, androgens, antiandrogens, gestagenes like progesterone as well as peptides, proteoglycans, glycolipids, phospholipids and derivatives therefrom.

Androgens, particularly androstendion and testosterone, as well as anti-androgens, including cyproteronacetate, flutamide, anandrone, linked to the nucleic acids increased effectiveness of the molecules in various cell types including prostatic carcinoma cells.

Oestrogens, anti-oestrogens and their derivatives, including fosfestrol, toremifen, ethinyloestradiole, diethylstilboestole and the oestradiole derivatives oestradiol-benzoate, oestradiol-valerinate and oestradiol-undecylate, as well as progesterone and its derivatives, including medroxyprogestroneacetate and megestrolacetate linked to the oligonucleotides strongly enhanced activity of the molecules according to the invention in various cell types including mammary carcinoma cells.

The invention claimed is:

1. A nucleic acid fragment consisting of an antisense oligonucleotide against gene TGF-β2 selected from the group consisting of SEQ ID NO: 532 and modified variants thereof.

2. A medicament useful for treating ischaemia comprising a medicinally effective amount of the nucleic acid fragment of claim 1 in combination with a medicinally acceptable carrier or diluent.

3. A method for increasing proliferation of cells in primary cell culture, comprising adding the nucleic acid fragment of claim 1 to primary cell culture.

4. The method of claim 3, wherein the cells in the primary cell culture are liver cells, kidney cells, osteoclasts, osteoblasts, keratinocytes, bone marrow stem cells, progenitor cells of red blood cells, or progenitor cells of white blood cells or a combination thereof.

5. The method of claim 3, wherein the nucleic acid fragment is added in an amount effective to inhibit gene TGF-β2.

* * * * *

SEQUENCE LISTING

```
<160> NUMBER OF SEQ ID NOS: 1764

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1
cccggagggc ggcatggggg a                                            21

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 2
cctcagggag aagggcgc                                                18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 3
gtaggagggc ctcgaggg                                                18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 4
ctgcaggggc tgggggtc                                                18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide
```

-continued

```
<400> SEQUENCE: 5
agggctggtg tggtgggg                                                   18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 6
ggcatggggg aggcggcg                                                   18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 7
ccggagggcg gcatgggg                                                   18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 8 gggggggctgg cgagccgc                                                  18

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 9
ggacaggatc tggccgcgga tgg                                             23

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 10 cccccctggct cgggggggc                                                 18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 11
```
gggccgggcg gcacctcc                                              18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 12
gggcagcggg ccgggcgg                                              18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 13
acggcctcgg gcagcggg                                              18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 14
gggtgctgtt gtacaggg                                              18

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 15
gggtttccac cattagcacg cggg                                       24

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 16
tcatagattt cgtt                                                  14

<210> SEQ ID NO 17
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 17
ttgtcataga ttt                                                        13

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 18
aagaacatat atatg                                                      15

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 19
aagaacatat atat                                                       14

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 20
ttgaagaaca tatata                                                     16

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 21
ccgggagagc aacacggg                                                   18

<210> SEQ ID NO 22
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 22
acttttaact tga                                                        13

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 23
attgttgctg tattt                                                      15

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 24
attgttgctg tatt                                                    14

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 25
aattgttgct gtatt                                                   15

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 26
aattgttgct gtat                                                    14

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 27
ggcgagtcgc tgggtgccag cagccgg                                      27

<210> SEQ ID NO 28
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 28
ggcgagtcgc tggg                                                    14

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 29
acatcaaaag ataa                                                    14

```
<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 30
tgacatcaaa agat                                                      14

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 31
gggccctctc cagcgggg                                                  18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 32
gggctcggcg gtgccggg                                                  18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 33
ggggcagggc ccgaggca                                                  18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 34
ggctccaaat gtaggggc                                                  18

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 35
cgggttatgc tggttgtaca gggc                                           24
```

```
<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 36
cggcgccgcc gaggcgcccg gg                                              22

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 37
ggggcggggc gggacc                                                     16

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 38
gggcggggcg gggcgggg                                                   18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 39
gggcggggtg gggccggg                                                   18

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 40
gggcaaggca gcggggcgg gg                                               22

<210> SEQ ID NO 41
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 41
cggtagcagc agcg                                                       14

<210> SEQ ID NO 42
```

```
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 42
ccagtagcca cagc                                                       14

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 43
gcaggtggat agtcc                                                      15

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 44
cttgcaggtg gatag                                                      15

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 45
cgatagtctt gcagg                                                      15

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 46
ccatgtcgat agtcttgc                                                   18

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 47
ctcgatgcgc ttccg                                                      15

<210> SEQ ID NO 48
<211> LENGTH: 15
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 48
cctcgatgcg cttcc                                                    15

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 49
ggatggcctc gatgc                                                    15

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 50
ggacaggatc tggcc                                                    15

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 51
cgcagcttgg acagg                                                    15

<210> SEQ ID NO 52
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 52
gagccgcagc ttgg                                                     14

<210> SEQ ID NO 53
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 53
cgagccgcag cttg                                                     14

<210> SEQ ID NO 54
<211> LENGTH: 14
<212> TYPE: DNA
```

-continued

```
<213> ORGANISM: Artificial Sequence
<220> FEATURE:
<223> OTHER INFORMATION: Description of Artificial Sequence:
      antisense oligonucleotide

<400> SEQUENCE: 54 acctcccct ggct                                                         14

<210> SEQ ID NO 55
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 55
ccaccattag cacg                                                        14

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 56
gaacttgtca tagatttc                                                    18

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 57
gctgtgtgta ctctgc                                                      16

<210> SEQ ID NO 58
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 58
gctccacgtg ctgc                                                        14

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 59
gaattgttgc tgtatttc                                                    18

<210> SEQ ID NO 60
<211> LENGTH: 15
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 60
gccaggaatt gttgc                                                    15

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 61
gtgacatcaa aagataac                                                 18

<210> SEQ ID NO 62
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 62
ggctcaacca ctgcc                                                    15

<210> SEQ ID NO 63
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 63
gctgtcacag gagc                                                     14

<210> SEQ ID NO 64
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 64
cctgctgtca cagg                                                     14

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 65
gcagtgtgtt atccctgc                                                 18

<210> SEQ ID NO 66
<211> LENGTH: 15
<212> TYPE: DNA
<213> ORGANISM: Artificial Sequence
<220> FEATURE:
```

<223> OTHER INFORMATION: Description of Artificial Sequence:
       antisense oligonucleotide

<400> SEQUENCE: 66
gcagtgtgtt atccc                                                    15

<210> SEQ ID NO 67
<211> LENGTH: 14
<212> TYPE: DNA
<213> ORGANISM: Artificial Sequence
<220> FEATURE:
<223> OTHER INFORMATION: Description of Artificial Sequence:
       antisense oligonucleotide

<400> SEQUENCE: 67
ccaggtcacc tcgg                                                     14

<210> SEQ ID NO 68
<211> LENGTH: 15
<212> TYPE: DNA
<213> ORGANISM: Artificial Sequence
<220> FEATURE:
<223> OTHER INFORMATION: Description of Artificial Sequence:
       antisense oligonucleotide

<400> SEQUENCE: 68
gccatgaatg gtggc                                                    15

<210> SEQ ID NO 69
<211> LENGTH: 14
<212> TYPE: DNA
<213> ORGANISM: Artificial Sequence
<220> FEATURE:
<223> OTHER INFORMATION: Description of Artificial Sequence:
       antisense oligonucleotide

<400> SEQUENCE: 69
gccatgaatg gtgg                                                     14

<210> SEQ ID NO 70
<211> LENGTH: 14
<212> TYPE: DNA
<213> ORGANISM: Artificial Sequence
<220> FEATURE:
<223> OTHER INFORMATION: Description of Artificial Sequence:
       antisense oligonucleotide

<400> SEQUENCE: 70
ccatgagaag cagg                                                     14

<210> SEQ ID NO 71
<211> LENGTH: 17
<212> TYPE: DNA
<213> ORGANISM: Artificial Sequence
<220> FEATURE:
<223> OTHER INFORMATION: Description of Artificial Sequence:
       antisense oligonucleotide

<400> SEQUENCE: 71
ggaagtcaat gtacagc                                                  17

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence:

-continued antisense oligonucleotide

<400> SEQUENCE: 72
ccacgtagta cacgatgg                                                  18

<210> SEQ ID NO 73
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 73
gcacttgcag gagc                                                      14

<210> SEQ ID NO 74
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 74
ccatggcagt gacc                                                      14

<210> SEQ ID NO 75
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 75
ggctcctcca tggc                                                      14

<210> SEQ ID NO 76
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 76
gctaggatct gactgc                                                    16

<210> SEQ ID NO 77
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 77
cctgactcag aggg                                                      14

<210> SEQ ID NO 78
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 78
ggtctgaaaa tgtttcc                                              17

<210> SEQ ID NO 79
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 79
ccattgcttg ggacgg                                               16

<210> SEQ ID NO 80
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 80
gcatcaaatc atcc                                                 14

<210> SEQ ID NO 81
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 81
ccattgttca atatcg                                               16

<210> SEQ ID NO 82
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 82
ggtcttcagt gaacc                                                15

<210> SEQ ID NO 83
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 83
ggagcttcat ctggacc                                              17

<210> SEQ ID NO 84
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

```
<400> SEQUENCE: 84
cctctggcat tctgg                                                    15

<210> SEQ ID NO 85
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 85
agggacagaa gatg                                                     14

<210> SEQ ID NO 86
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 86
gttttctggg aagg                                                     14

<210> SEQ ID NO 87
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 87
ggttttctgg gaag                                                     14

<210> SEQ ID NO 88
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 88
aggttttctg ggaag                                                    15

<210> SEQ ID NO 89
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 89
gtaggttttc tggg                                                     14

<210> SEQ ID NO 90
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 90
```

```
ggtaggtttt ctgg                                                    14
```

<210> SEQ ID NO 91
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 91

```
ccagaatgca agaagcc                                                 17
```

<210> SEQ ID NO 92
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 92

```
gctgtcccag aatgc                                                   15
```

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 93

```
gcaagtcaca gacttggc                                                18
```

<210> SEQ ID NO 94
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 94

```
ccacagctgc acagg                                                   15
```

<210> SEQ ID NO 95
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 95

```
ggtgtggaat caacc                                                   15
```

<210> SEQ ID NO 96
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 96

-continued gtcatgtgct gtga 14

<210> SEQ ID NO 97
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 97
cgctatctga gcagcg 16

<210> SEQ ID NO 98
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 98
ccagtgtgat gatgg 15

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 99
ccagtagatt accactgg 18

<210> SEQ ID NO 100
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 100
ggcacaaaca cgcacc 16

<210> SEQ ID NO 101
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 101
ccacggatct gaagg 15

<210> SEQ ID NO 102
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 102
cggaacatct cgaagcg 17

```
<210> SEQ ID NO 103
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 103
cctcattcag ctctcgg                                                       17

<210> SEQ ID NO 104
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 104
ccttgagttc caagg                                                         15

<210> SEQ ID NO 105
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 105 ccttttttgga cttcagg                                                      17

<210> SEQ ID NO 106
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 106
ggaggtagac tgaccc                                                        16

<210> SEQ ID NO 107
<211> LENGTH: 12
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 107
aaaatgtttc ct                                                            12

<210> SEQ ID NO 108
<211> LENGTH: 12
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 108
tgaaaatgtt tc                                                            12
```

```
<210> SEQ ID NO 109
<211> LENGTH: 12
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 109
ctgaaaatgt tt                                                        12

<210> SEQ ID NO 110
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 110
tctgaaaatg ttt                                                       13

<210> SEQ ID NO 111
<211> LENGTH: 12
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 111
tctgaaaatg tt                                                        12

<210> SEQ ID NO 112
<211> LENGTH: 12
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 112
aaatcatcca tt                                                        12

<210> SEQ ID NO 113
<211> LENGTH: 12
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 113
ttgttcaata tc                                                        12

<210> SEQ ID NO 114
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 114
attgttcaat atc                                                       13
```

<210> SEQ ID NO 115
<211> LENGTH: 12
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 115
attgttcaat at                                                              12

<210> SEQ ID NO 116
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 116
cattgttcaa tat                                                             13

<210> SEQ ID NO 117
<211> LENGTH: 12
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 117
cattgttcaa ta                                                              12

<210> SEQ ID NO 118
<211> LENGTH: 12
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 118
aaaagtgttt ct                                                              12

<210> SEQ ID NO 119
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 119
acatgagttt tttat                                                           15

<210> SEQ ID NO 120
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 120
aacatgagtt ttttat                                                          16

<210> SEQ ID NO 121

```
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 121
acatgagttt ttta                                                       14

<210> SEQ ID NO 122
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 122
aacatgagtt tttta                                                      15

<210> SEQ ID NO 123
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 123
aacatgagtt tttt                                                       14

<210> SEQ ID NO 124
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 124
aaaacatctt gtt                                                        13

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 125 cagaggggg ctcgacgc                                                    18

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 126
ctgactcaga gggggctc                                                   18

<210> SEQ ID NO 127
<211> LENGTH: 14
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 127 aggggacag aacg                                                          14

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 128
ttgggacggc aaggggaca gaa                                                23

<210> SEQ ID NO 129
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 129
tgggacggca aggggga                                                      17

<210> SEQ ID NO 130
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 130
gccacggggg gagca                                                        15

<210> SEQ ID NO 131
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 131
gcaggggcca cggggggag                                                    19

<210> SEQ ID NO 132
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 132
aggggccacg gggg                                                         14

<210> SEQ ID NO 133
<211> LENGTH: 14
<212> TYPE: DNA
```

-continued

```
<213> ORGANISM: Artificial Sequence
<220> FEATURE:
<223> OTHER INFORMATION: Description of Artificial Sequence:
      antisense oligonucleotide

<400> SEQUENCE: 133 cagggggccac gggg                                                        14

<210> SEQ ID NO 134
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 134
ggtgcagggg ccacg                                                        15

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 135
tggtgcaggg gccgccgg                                                     18

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 136
ggggctggtg caggggcc                                                     18

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 137 aggggggctgg tgcagggg                                                    18

<210> SEQ ID NO 138
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 138
gggctggtgc aggg                                                         14

<210> SEQ ID NO 139
<211> LENGTH: 16
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 139 gaggggctg gtgcag                                                         16

<210> SEQ ID NO 140
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 140 aggaggggc tggtg                                                          15

<210> SEQ ID NO 141
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 141
gggccaggag ggggctgg                                                      18

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 142
aggggccagg aggggggct                                                     18

<210> SEQ ID NO 143
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 143
ggggccagga gggg                                                          14

<210> SEQ ID NO 144
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 144
caggggccag gaggg                                                         15

<210> SEQ ID NO 145
<211> LENGTH: 16
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 145
tctgggaagg gacaga                                                    16

<210> SEQ ID NO 146
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 146
tgagggcagg ggagta                                                    16

<210> SEQ ID NO 147
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 147
ttgagggcag gggag                                                     15

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 148
cgggtgccgg gcggggtg                                                  19

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 149
cggacgcggg tgccgggcgg gggt                                           24

<210> SEQ ID NO 150
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 150
cgggtgccgg gcggg                                                     15

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence:
``` antisense oligonucleotide

<400> SEQUENCE: 151
ggacgcgggt gccgggcg                                                       18

<210> SEQ ID NO 152
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 152
tgggggcagc gcctcaca                                                       18

<210> SEQ ID NO 153
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 153
ggtgggggca gcgcct                                                         16

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 154
ccattttagt gcacatccgg                                                     20

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 155
ccattttagt gcacatcc                                                       18

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 156
gctgttccat tttagtgc                                                       18

<210> SEQ ID NO 157
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 157
gtagtcgtgt agag                                                 14

<210> SEQ ID NO 158
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 158
gtttgtagtc gtgtag                                               16

<210> SEQ ID NO 159
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 159
gtttcaggag tttgtag                                              17

<210> SEQ ID NO 160
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 160
ccagctccga agagg                                                15

<210> SEQ ID NO 161
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 161
cgtcgtcgtg atcacg                                               16

<210> SEQ ID NO 162
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 162
ggtaaaagta ctgtcc                                               16

<210> SEQ ID NO 163
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

```
<400> SEQUENCE: 163
ggctttgaca aagcc                                              15

<210> SEQ ID NO 164
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 164
cttgtgcaga tcgtccag                                           18

<210> SEQ ID NO 165
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 165
cgtggttcat cttgtgc                                            17

<210> SEQ ID NO 166
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 166
cacgtggttc atcttgtg                                           18

<210> SEQ ID NO 167
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 167
cctccttgaa ggtgg                                              15

<210> SEQ ID NO 168
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 168
cgctccactt tgatgcg                                            17

<210> SEQ ID NO 169
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 169
```

```
ccttgtcctc cagg                                                         14
```

<210> SEQ ID NO 170
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 170

```
ggtactcgac agcc                                                         14
```

<210> SEQ ID NO 171
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 171

```
ctgacgtggg tcatg                                                        15
```

<210> SEQ ID NO 172
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 172

```
ccgttgctga cgtgg                                                        15
```

<210> SEQ ID NO 173
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 173

```
catcctccgc ctcc                                                         14
```

<210> SEQ ID NO 174
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 174

```
gtttccatcc tccg                                                         14
```

<210> SEQ ID NO 175
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 175
ggtgtttcca tcctcc                                                         16

<210> SEQ ID NO 176
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 176
ggtgtttcca tcctc                                                          15

<210> SEQ ID NO 177
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 177
gctcagcgcc tcatc                                                          15

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 178
ccttcttcat catgctgc                                                       18

<210> SEQ ID NO 179
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 179
ccttcttcat catgctg                                                        17

<210> SEQ ID NO 180
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 180
ccttcttcat catgc                                                          15

<210> SEQ ID NO 181
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 181
gcgtccttct tcatcatgc                                                      19

```
<210> SEQ ID NO 182
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 182
cctgctcact cagg                                                          14

<210> SEQ ID NO 183
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 183
cgcaggcttg agcg                                                          14

<210> SEQ ID NO 184
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 184
gccagcttca gcagc                                                         15

<210> SEQ ID NO 185
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 185
ggtggtgacc agcc                                                          14

<210> SEQ ID NO 186
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 186
cctcggcgaa ctcc                                                          14

<210> SEQ ID NO 187
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 187
gcttgtgtaa atcc                                                          14
```

```
<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 188
ggttctgctt gtgtaaatcc                                              20

<210> SEQ ID NO 189
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 189
gctgctcagg ttcgc                                                   15

<210> SEQ ID NO 190
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 190
gaaggcgacc gtcg                                                    14

<210> SEQ ID NO 191
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 191
cgaaggcgac cgtc                                                    14

<210> SEQ ID NO 192
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 192
gcaccgtctg tggc                                                    14

<210> SEQ ID NO 193
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 193
cgtgtccatg tcgatgg                                                 17
```

```
<210> SEQ ID NO 194
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 194
cgtgtccatg tcgatg                                                        16

<210> SEQ ID NO 195
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 195
gcgtgtccat gtcg                                                          14

<210> SEQ ID NO 196
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 196
ccagcttgcg cttgc                                                         15

<210> SEQ ID NO 197
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 197
cgctccagct tgcg                                                          14

<210> SEQ ID NO 198
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 198
cgtgttctga ctcttgag                                                      18

<210> SEQ ID NO 199
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 199
cgtgttctga ctcttg                                                        16

<210> SEQ ID NO 200
```

```
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 200
gctgttgacg tggc                                                       14

<210> SEQ ID NO 201
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 201
cgactcagta cgcc                                                       14

<210> SEQ ID NO 202
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 202
gccatgcccg actc                                                       14

<210> SEQ ID NO 203
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 203
cccttggagg tggc                                                       14

<210> SEQ ID NO 204
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 204
ttttagtgca cat                                                        13

<210> SEQ ID NO 205
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 205
tgttccattt tagt                                                       14

<210> SEQ ID NO 206
<211> LENGTH: 14
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 206
aaaaaaagtg gaag                                                        14

<210> SEQ ID NO 207
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 207
tacaaaaaaa agtg                                                        14

<210> SEQ ID NO 208
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 208
atacaaaaaa aagt                                                        14

<210> SEQ ID NO 209
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 209
catacaaaaa aaagt                                                       15

<210> SEQ ID NO 210
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 210
catacaaaaa aaag                                                        14

<210> SEQ ID NO 211
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 211 gaaaaaaac atac                                                         14

<210> SEQ ID NO 212
<211> LENGTH: 16
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 212
cagaaaaaaa acatac                                                       16

<210> SEQ ID NO 213
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 213
cagaaaaaaa acat                                                         14

<210> SEQ ID NO 214
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 214
ttcaatatga atcg                                                         14

<210> SEQ ID NO 215
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 215
tattcaatat gaatcg                                                       16

<210> SEQ ID NO 216
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 216
tattcaatat gaatc                                                        15

<210> SEQ ID NO 217
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 217
tattcaatat gaat                                                         14

<210> SEQ ID NO 218
<211> LENGTH: 15
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 218
tatattcaat atgaa                                                    15

<210> SEQ ID NO 219
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 219
ttatattcaa tatga                                                    15

<210> SEQ ID NO 220
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 220
tattatattc aatatga                                                  17

<210> SEQ ID NO 221
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 221
ttatattcaa tatg                                                     14

<210> SEQ ID NO 222
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 222
tattatattc aatatg                                                   16

<210> SEQ ID NO 223
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 223
attatattca atat                                                     14

<210> SEQ ID NO 224
<211> LENGTH: 15
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 224
tattatattc aatat                                                        15

<210> SEQ ID NO 225
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 225
atatattata ttcaatat                                                     18

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 226
aaatatatta tattcaatat                                                   20

<210> SEQ ID NO 227
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 227
tattatattc aata                                                         14

<210> SEQ ID NO 228
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 228
atatattata ttcaata                                                      17

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 229
caaatatatt atattcaata                                                   20

<210> SEQ ID NO 230
<211> LENGTH: 15
<212> TYPE: DNA
<213> ORGANISM: Artificial Sequence
<220> FEATURE:
<223> OTHER INFORMATION: Description of Artificial Sequence:
```

-continued antisense oligonucleotide

<400> SEQUENCE: 230
tatattatat tcaat                                                    15

<210> SEQ ID NO 231
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 231
aatatattat attcaat                                                  17

<210> SEQ ID NO 232
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 232
tatattatat tcaa                                                     14

<210> SEQ ID NO 233
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 233
caaatatatt atattcaa                                                 18

<210> SEQ ID NO 234
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 234
caaatatatt atattca                                                  17

<210> SEQ ID NO 235
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 235
caaatatatt atattc                                                   16

<210> SEQ ID NO 236
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

```
<400> SEQUENCE: 236
cacaaatata ttatattc                                              18

<210> SEQ ID NO 237
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 237
aaatatatta tatt                                                  14

<210> SEQ ID NO 238
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 238
caaatatatt atatt                                                 15

<210> SEQ ID NO 239
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 239
caaatatatt atat                                                  14

<210> SEQ ID NO 240
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 240
cacaaatata ttatat                                                16

<210> SEQ ID NO 241
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 241
cacaaatata ttat                                                  14

<210> SEQ ID NO 242
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide
```

<400> SEQUENCE: 242
tacacaaata tattat                                            16

<210> SEQ ID NO 243
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 243
tacacaaata tatta                                             15

<210> SEQ ID NO 244
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 244
taaatacaca aatatatt                                          18

<210> SEQ ID NO 245
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 245
aatacacaaa tata                                              14

<210> SEQ ID NO 246
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 246
gttaaataca caaata                                            16

<210> SEQ ID NO 247
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 247
tgttaaatac acaa                                              14

<210> SEQ ID NO 248
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 248

```
tttagagact aagt                                                    14

<210> SEQ ID NO 249
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 249
ataaactctt taga                                                    14

<210> SEQ ID NO 250
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 250
taaaataaac tctttag                                                 17

<210> SEQ ID NO 251
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 251
taaaataaac tcttta                                                  16

<210> SEQ ID NO 252
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 252
ttaaaataaa ctcttt                                                  16

<210> SEQ ID NO 253
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 253
cttaaaataa actc                                                    14

<210> SEQ ID NO 254
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 254
```

```
taaaaagaac aaaca                                                     15

<210> SEQ ID NO 255
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 255
taaaaagaac aaac                                                      14

<210> SEQ ID NO 256
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 256
caataaaaag aacaa                                                     15

<210> SEQ ID NO 257
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 257
tcaataaaaa gaacaa                                                    16

<210> SEQ ID NO 258
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 258
tcaataaaaa gaac                                                      14

<210> SEQ ID NO 259
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 259
ttcaataaaa agaa                                                      14

<210> SEQ ID NO 260
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 260
tagattcaat aaaaaga                                                   17
```

<210> SEQ ID NO 261
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 261
tggcgcgggc gggtagc                                                17

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 262
gggctggcgc gggcgggtag                                             20

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 263
tcgggggctg gcgcgggcgg g                                           21

<210> SEQ ID NO 264
<211> LENGTH: 26
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 264
tgggtgcctg gtcgcgcgtt ctcggg                                      26

<210> SEQ ID NO 265
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 265
agggtccctg cggggccg                                               18

<210> SEQ ID NO 266
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 266
gggagggtcc ctgcgggg                                               18

```
<210> SEQ ID NO 267
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 267
gggagggtcc ctgcgg                                                      16

<210> SEQ ID NO 268
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 268
tgggccgggt ccgc                                                        14

<210> SEQ ID NO 269
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 269
tcccgggggt gtag                                                        14

<210> SEQ ID NO 270
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 270
agtactgtcc cggggtgt                                                    19

<210> SEQ ID NO 271
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 271
gggacacgtt gggggtg                                                     18

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 272
gccgggggcc ccccggtagc                                                  20
```

```
<210> SEQ ID NO 273
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 273
cgggcccagc cggggc                                                    17

<210> SEQ ID NO 274
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 274
cgggcccagc cggg                                                      14

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 275
gggaggtggc tccgggccgg                                                20

<210> SEQ ID NO 276
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 276
agggcggcgc gtgtggga                                                  18

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 277
gggtggccac cggcgaaggg                                                20

<210> SEQ ID NO 278
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 278
aggggcaggg gacgt                                                     15

<210> SEQ ID NO 279
```

```
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 279
taaaggggca ggggacgt                                                 18

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 280 aggggggtgtc cgtaaagggg                                              20

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 281
ggggacgcga acgtgccgcc g                                             21

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 282
cggggaacaa gcggcccggg g                                             21

<210> SEQ ID NO 283
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 283
ggccgtcggg ggcg                                                     14

<210> SEQ ID NO 284
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 284
gcggccgtcg gggc                                                     15

<210> SEQ ID NO 285
<211> LENGTH: 18
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 285 agggggggtag gaggcggg                                                    18

<210> SEQ ID NO 286
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 286
gcgctggggg cgcc                                                         14

<210> SEQ ID NO 287
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 287
ggccgtcggg gggt                                                         14

<210> SEQ ID NO 288
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 288
ggggaggcca gcttc                                                        15

<210> SEQ ID NO 289
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 289
ggccgccacc ttgggg                                                       16

<210> SEQ ID NO 290
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 290
gcggccgccg ccgggg                                                       16

<210> SEQ ID NO 291
<211> LENGTH: 20
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 291
gggcgcggcc gccgccgggg                                               20

<210> SEQ ID NO 292
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 292
ggggtggcgg cggcgg                                                   16

<210> SEQ ID NO 293
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 293
gggggtggcg gcggc                                                    15

<210> SEQ ID NO 294
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 294
tggggcagca gctggcag                                                 18

<210> SEQ ID NO 295
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 295
cggggcgccc acgacacc                                                 18

<210> SEQ ID NO 296
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 296
cggggcgccc acgacac                                                  17

<210> SEQ ID NO 297
<211> LENGTH: 26
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 297
gggccgcacc ctctccaagt ccgggg                                              26

<210> SEQ ID NO 298
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 298
gcagcagtca gtgg                                                           14

<210> SEQ ID NO 299
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 299
ccattgtcta gcacgg                                                         16

<210> SEQ ID NO 300
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 300
ggtctccatt gtctagc                                                        17

<210> SEQ ID NO 301
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 301
ggtggtattg ttcagc                                                         16

<210> SEQ ID NO 302
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 302
gctggatcaa gaccc                                                          15

<210> SEQ ID NO 303
<211> LENGTH: 16
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 303
ccacaaaatc gtgtcc                                                       16

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 304
ccttccacaa aatcgtgtcc                                                   20

<210> SEQ ID NO 305
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 305
ggttgttctt gtgg                                                         14

<210> SEQ ID NO 306
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 306
cctcttggtt gtgc                                                         14

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 307
ccagagtctc aaacacttgg                                                   20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 308
ggtaacctgt gatctcttcc                                                   20

<210> SEQ ID NO 309
<211> LENGTH: 14
<212> TYPE: DNA
<213> ORGANISM: Artificial Sequence
<220> FEATURE:
<223> OTHER INFORMATION: Description of Artificial Sequence:
``` antisense oligonucleotide

<400> SEQUENCE: 309
cctgcagtac tcgg                                                        14

<210> SEQ ID NO 310
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 310
ggcattcaca tactcc                                                      16

<210> SEQ ID NO 311
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 311
ggcattcaca tactcc                                                      16

<210> SEQ ID NO 312
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 312
cgcatcgtgt acttccg                                                     17

<210> SEQ ID NO 313
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 313
gcacgttccg agcg                                                        14

<210> SEQ ID NO 314
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 314
ggtaccagat actcc                                                       15

<210> SEQ ID NO 315
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 315
ccagtggaga cctgg                                                    15

<210> SEQ ID NO 316
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 316
cctgaggaca catcagg                                                  17

<210> SEQ ID NO 317
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 317
cctcacttgg ttgtgagc                                                 18

<210> SEQ ID NO 318
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 318
ggaagatgtc cttcc                                                    15

<210> SEQ ID NO 319
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 319
gcacactgct catggc                                                   16

<210> SEQ ID NO 320
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 320
gctgtcacct cttgg                                                    15

<210> SEQ ID NO 321
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

```
<400> SEQUENCE: 321
cctctgctgt cacc                                                     14

<210> SEQ ID NO 322
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 322
ccacacatca ctctgg                                                   16

<210> SEQ ID NO 323
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 323
cctcctcttc agagg                                                    15

<210> SEQ ID NO 324
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 324
ccttctggtt cacactgg                                                 18

<210> SEQ ID NO 325
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 325
catggtgctc actgcg                                                   16

<210> SEQ ID NO 326
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 326
cttggttgtg agcg                                                     14

<210> SEQ ID NO 327
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 327
```
ggacaggcag tcac                                            14

<210> SEQ ID NO 328
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 328
gtcacctctt ggttgtgc                                        18

<210> SEQ ID NO 329
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 329
ccagagtctc aaacac                                          16

<210> SEQ ID NO 330
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 330
cacatactcc ctgg                                            14

<210> SEQ ID NO 331
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 331
gaccagcacg ttccg                                           15

<210> SEQ ID NO 332
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 332
gttggtgtct atcagtg                                         17

<210> SEQ ID NO 333
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 333

```
ccctggtaga ggtg                                                    14

<210> SEQ ID NO 334
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 334
ctcaaacact tggagc                                                  16

<210> SEQ ID NO 335
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 335
cacacatcac tctggtgg                                                18

<210> SEQ ID NO 336
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 336
gcacagacag tgcgc                                                   15

<210> SEQ ID NO 337
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 337
catggcagca gtcag                                                   15

<210> SEQ ID NO 338
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 338
ctgctcatgg cagcag                                                  16

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 339
catctggaaa cttccagatg                                              20
```

```
<210> SEQ ID NO 340
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 340
ctggaaactt ccag                                                        14

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 341
cataactcca cacatcactc                                                  20

<210> SEQ ID NO 342
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 342
caccataact ccacacatc                                                   19

<210> SEQ ID NO 343
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 343
ctggtgggtg aacc                                                        14

<210> SEQ ID NO 344
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 344
cggattactt gcagg                                                       15

<210> SEQ ID NO 345
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 345
cgctaggtgt cagcg                                                       15
```

```
<210> SEQ ID NO 346
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 346
gccatcacgt atgc                                                           14

<210> SEQ ID NO 347
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 347
gcatacacca gttcagc                                                        17

<210> SEQ ID NO 348
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 348
ccatcaaata catcgg                                                         16

<210> SEQ ID NO 349
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 349
ccagcagaag tcagg                                                          15

<210> SEQ ID NO 350
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 350
gcttcatgtc tgtgc                                                          15

<210> SEQ ID NO 351
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 351
ggtgagttcc aggtttcc                                                       18
```

```
<210> SEQ ID NO 352
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 352
ccacaaaatc gtgtcctgg                                              19

<210> SEQ ID NO 353
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 353
cccttacaca tcgg                                                   14

<210> SEQ ID NO 354
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 354
gcagctcaca gatgc                                                  15

<210> SEQ ID NO 355
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 355
gcactggtaa ctgc                                                   14

<210> SEQ ID NO 356
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 356
cctggatatt ggcactgg                                               18

<210> SEQ ID NO 357
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 357
ccagcaaact cctgg                                                  15

<210> SEQ ID NO 358
```

```
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 358
gcagaaatgc caggc                                                      15

<210> SEQ ID NO 359
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 359
ccattgtgca gaattcg                                                    17

<210> SEQ ID NO 360
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 360
ccctgcagta ctcgg                                                      15

<210> SEQ ID NO 361
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 361
ggcattcaca tactccc                                                    17

<210> SEQ ID NO 362
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 362
ggtcaggttt cacacc                                                     16

<210> SEQ ID NO 363
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 363
ccaggtccac acagg                                                      15

<210> SEQ ID NO 364
<211> LENGTH: 14
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 364
ccttgtcatc cagg                                                          14

<210> SEQ ID NO 365
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 365
ggatcccaaa gacc                                                          14

<210> SEQ ID NO 366
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 366
cctcaacact ttgatgg                                                       17

<210> SEQ ID NO 367
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 367
gctgtgtcac cagc                                                          14

<210> SEQ ID NO 368
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 368
ggtctaagag gcagcc                                                        16

<210> SEQ ID NO 369
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 369
ggcaatctgc atacacc                                                       17

<210> SEQ ID NO 370
<211> LENGTH: 14
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 370
cctgtgtacg agcc                                                      14

<210> SEQ ID NO 371
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 371
ccatccactt gatgg                                                     15

<210> SEQ ID NO 372
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 372
cccacacagt cacacc                                                    16

<210> SEQ ID NO 373
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 373
ccatcgtaag gtttgg                                                    16

<210> SEQ ID NO 374
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 374 cctttccag cagg                                                       14

<210> SEQ ID NO 375
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 375
ggagaattca gacacc                                                    16

<210> SEQ ID NO 376
<211> LENGTH: 17
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 376
ccaagtcctc attctgg                                                      17

<210> SEQ ID NO 377
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 377
ccatcagtct cagagg                                                       16

<210> SEQ ID NO 378
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 378
cctttgaagg tgctgg                                                       16

<210> SEQ ID NO 379
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 379
ggcatggcag gttcc                                                        15

<210> SEQ ID NO 380
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 380
cctggcatgg cagg                                                         14

<210> SEQ ID NO 381
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 381
agatgtatag gtaa                                                         14

<210> SEQ ID NO 382
<211> LENGTH: 14
<212> TYPE: DNA
<213> ORGANISM: Artificial Sequence
<220> FEATURE:
```

<223> OTHER INFORMATION: Description of Artificial Sequence:
      antisense oligonucleotide

<400> SEQUENCE: 382
attttcacat tctc                                                    14

<210> SEQ ID NO 383
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 383
aattttcaca ttctc                                                   15

<210> SEQ ID NO 384
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 384
aattttcaca ttct                                                    14

<210> SEQ ID NO 385
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 385
gaattttcac attc                                                    14

<210> SEQ ID NO 386
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 386
ggaattttca catt                                                    14

<210> SEQ ID NO 387
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 387
agatttcttt gttg                                                    14

<210> SEQ ID NO 388
<211> LENGTH: 15
<212> TYPE: DNA
<213> ORGANISM: Artificial Sequence
<220> FEATURE:
<223> OTHER INFORMATION: Description of Artificial Sequence:

antisense oligonucleotide

<400> SEQUENCE: 388
aagatttctt tgttg                                            15

<210> SEQ ID NO 389
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 389
aagatttctt tgtt                                             14

<210> SEQ ID NO 390
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 390
taagatttct ttgtt                                            15

<210> SEQ ID NO 391
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 391
ctaagatttc tttgtt                                           16

<210> SEQ ID NO 392
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 392
taagatttct ttgt                                             14

<210> SEQ ID NO 393
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 393
ctaagatttc tttgt                                            15

<210> SEQ ID NO 394
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide -continued

```
<400> SEQUENCE: 394
ctaagatttc tttg                                                  14

<210> SEQ ID NO 395
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 395
tctaagattt cttt                                                  14

<210> SEQ ID NO 396
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 396
gtctaagatt tcttt                                                 15

<210> SEQ ID NO 397
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 397
gtctaagatt tctt                                                  14

<210> SEQ ID NO 398
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 398
ttcgtctaag attt                                                  14

<210> SEQ ID NO 399
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 399
attttgacat ggtt                                                  14

<210> SEQ ID NO 400
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide
```

-continued

```
<400> SEQUENCE: 400
aattttgaca tggtt                                                     15

<210> SEQ ID NO 401
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 401
aattttgaca tggt                                                      14

<210> SEQ ID NO 402
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 402
taattttgac atggt                                                     15

<210> SEQ ID NO 403
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 403
taattttgac atgg                                                      14

<210> SEQ ID NO 404
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 404
gtaattttga catg                                                      14

<210> SEQ ID NO 405
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 405
tgtaattttg acatg                                                     15

<210> SEQ ID NO 406
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 406
```
tgtaattttg acat                                                    14

<210> SEQ ID NO 407
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 407
tctgtaattt tgacat                                                  16

<210> SEQ ID NO 408
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 408
ctgtaatttt gaca                                                    14

<210> SEQ ID NO 409
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 409
tctgtaattt tgaca                                                   15

<210> SEQ ID NO 410
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 410
tctgtaattt tgac                                                    14

<210> SEQ ID NO 411
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 411
gtctgtaatt ttga                                                    14

<210> SEQ ID NO 412
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 412

```
aagtctgtaa ttttga                                                       16
```

<210> SEQ ID NO 413
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 413

```
agtctgtaat tttg                                                         14
```

<210> SEQ ID NO 414
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 414

```
aagtctgtaa ttttg                                                        15
```

<210> SEQ ID NO 415
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 415

```
aagtctgtaa tttt                                                         14
```

<210> SEQ ID NO 416
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 416

```
gaagtctgta atttt                                                        15
```

<210> SEQ ID NO 417
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 417

```
gaagtctgta attt                                                         14
```

<210> SEQ ID NO 418
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 418

```
atgtagacat caat                                                         14
```

```
<210> SEQ ID NO 419
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 419
atcatccaac attt                                                        14

<210> SEQ ID NO 420
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 420
aatcatccaa cattt                                                       15

<210> SEQ ID NO 421
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 421
aatcatccaa catt                                                        14

<210> SEQ ID NO 422
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 422
accatcaaat acat                                                        14

<210> SEQ ID NO 423
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 423
aaaaacgtct ttga                                                        14

<210> SEQ ID NO 424
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 424
ttttgttctt agaca                                                       15
```

```
<210> SEQ ID NO 425
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 425
ttttgttctt agac                                                      14

<210> SEQ ID NO 426
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 426
taaacagaaa agca                                                      14

<210> SEQ ID NO 427
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 427
actaaacaga aaag                                                      14

<210> SEQ ID NO 428
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 428
aaactaaaca gaaaag                                                    16

<210> SEQ ID NO 429
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 429
aactaaacag aaaa                                                      14

<210> SEQ ID NO 430
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 430
aaactaaaca gaaaa                                                     15
```

```
<210> SEQ ID NO 431
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 431
aaactaaaca gaaa                                                        14

<210> SEQ ID NO 432
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 432
taaaaactaa acagaaa                                                     17

<210> SEQ ID NO 433
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 433
aaaactaaac agaa                                                        14

<210> SEQ ID NO 434
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 434
gtaaaaacta aacagaa                                                     17

<210> SEQ ID NO 435
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 435
aaaaactaaa caga                                                        14

<210> SEQ ID NO 436
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 436
taaaaactaa acaga                                                       15

<210> SEQ ID NO 437
```

```
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 437
taaaaactaa acag                                                         14

<210> SEQ ID NO 438
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 438
gtaaaaacta aaca                                                         14

<210> SEQ ID NO 439
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 439
aaaaagtaaa aactaaaca                                                    19

<210> SEQ ID NO 440
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 440
agtaaaaact aaac                                                         14

<210> SEQ ID NO 441
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 441
aaaaaaagta aaactaaac                                                    20

<210> SEQ ID NO 442
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 442
aagtaaaaac taaa                                                         14

<210> SEQ ID NO 443
<211> LENGTH: 19
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 443
aaaaaaagta aaactaaa                                                    19

<210> SEQ ID NO 444
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 444
aaagtaaaaa ctaa                                                        14

<210> SEQ ID NO 445
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 445
aaaagtaaaa acta                                                        14

<210> SEQ ID NO 446
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 446
aaaaaaagta aaacta                                                      17

<210> SEQ ID NO 447
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 447
aaaaagtaaa aact                                                        14

<210> SEQ ID NO 448
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 448
aaaaaaagta aaact                                                       16

<210> SEQ ID NO 449
<211> LENGTH: 15
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 449
aaaaaaagta aaaac                                                      15

<210> SEQ ID NO 450
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 450
caaaaaaagt aaaaac                                                     16

<210> SEQ ID NO 451
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 451
aaaaaaagta aaaa                                                       14

<210> SEQ ID NO 452
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 452 caaaaaagt aaaa                                                        14

<210> SEQ ID NO 453
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 453
aacaaaacaa aaaagtaaa                                                  20

<210> SEQ ID NO 454
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 454
aaacaaaaaa agta                                                       14

<210> SEQ ID NO 455
<211> LENGTH: 16
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 455
caaaacaaaa aaagta                                                     16

<210> SEQ ID NO 456
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 456
caaaacaaaa aaagt                                                      15

<210> SEQ ID NO 457
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 457
caaaacaaaa aaag                                                       14

<210> SEQ ID NO 458
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 458
ctttaaaaaa acaaaac                                                    17

<210> SEQ ID NO 459
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 459
tctttaaaaa aacaaa                                                     16

<210> SEQ ID NO 460
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 460
gtctttaaaa aaacaaa                                                    17

<210> SEQ ID NO 461
<211> LENGTH: 15
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 461
gtctttaaaa aaaca                                                        15

<210> SEQ ID NO 462
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 462
gtctttaaaa aaac                                                         14

<210> SEQ ID NO 463
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 463
tttatttcgt cttt                                                         14

<210> SEQ ID NO 464
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 464
tctttatttc gtct                                                         14

<210> SEQ ID NO 465
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 465
tatttgcaaa tgga                                                         14

<210> SEQ ID NO 466
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 466
tatatttgca aatgg                                                        15

<210> SEQ ID NO 467
<211> LENGTH: 14
<212> TYPE: DNA
<213> ORGANISM: Artificial Sequence
<220> FEATURE:
<223> OTHER INFORMATION: Description of Artificial Sequence:
``` antisense oligonucleotide

<400> SEQUENCE: 467
tatatttgca aatg 14

<210> SEQ ID NO 468
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 468
caaaatatat ttgcaaatg 19

<210> SEQ ID NO 469
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 469
caaaatatat ttgcaaat 18

<210> SEQ ID NO 470
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 470
caaaatatat ttgca 15

<210> SEQ ID NO 471
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 471
caaaatatat ttgc 14

<210> SEQ ID NO 472
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 472
ttccaaaata tatttg 16

<210> SEQ ID NO 473
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

```
<400> SEQUENCE: 473 tttccaaaa tatattt                                              17

<210> SEQ ID NO 474
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 474
gttttccaaa atatatt                                             17

<210> SEQ ID NO 475
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 475
gttttccaaa atat                                                14

<210> SEQ ID NO 476
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 476
ggttaggcaa agcc                                                14

<210> SEQ ID NO 477
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 477
ccgagaacat catcgtgg                                            18

<210> SEQ ID NO 478
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 478
ccgagaacat catcgtg                                             17

<210> SEQ ID NO 479
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide
```

```
<400> SEQUENCE: 479
ccgagaacat catcg                                                    15

<210> SEQ ID NO 480
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 480
cgtagtctgc gttgaagc                                                 18

<210> SEQ ID NO 481
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 481
ccatgctgga gaagg                                                    15

<210> SEQ ID NO 482
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 482
ccgtgcagaa gtcc                                                     14

<210> SEQ ID NO 483
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 483
ggaatgaagt tggc                                                     14

<210> SEQ ID NO 484
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 484
tgaccgtggg aatg                                                     14

<210> SEQ ID NO 485
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 485
```

```
tggcagtgac cgtg                                                      14

<210> SEQ ID NO 486
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 486
agatggcagt gacc                                                      14

<210> SEQ ID NO 487
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 487
cgagatggca gtgacc                                                    16

<210> SEQ ID NO 488
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 488
ccagccactg cagg                                                      14

<210> SEQ ID NO 489
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 489
gcaccagcca ctgc                                                      14

<210> SEQ ID NO 490
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 490
ccctggagta agcc                                                      14

<210> SEQ ID NO 491
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 491
```
ggagataact gttccacc                                                         18

<210> SEQ ID NO 492
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 492
ggagataact gttcc                                                            15

<210> SEQ ID NO 493
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 493
cttctagttg gtctg                                                            15

<210> SEQ ID NO 494
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 494
catcttctag ttgg                                                             14

<210> SEQ ID NO 495
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 495
tctcatcttc tagttgg                                                          17

<210> SEQ ID NO 496
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 496
ctgcaaagca gacttctc                                                         18

<210> SEQ ID NO 497
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 497
ccttcagcag gttgg                                                            15

<210> SEQ ID NO 498
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 498
cccaggtcat cagg                                                           14

<210> SEQ ID NO 499
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 499
ccagtcagat caagg                                                          15

<210> SEQ ID NO 500
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 500
ggtgaaggcc tcctc                                                          15

<210> SEQ ID NO 501
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 501
cagggtgaag gcctc                                                          15

<210> SEQ ID NO 502
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 502
cctggatgat gctgg                                                          15

<210> SEQ ID NO 503
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 503
ccactgtgca gagg                                                           14

```
<210> SEQ ID NO 504
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 504
ggagtacagg tgacc                                              15

<210> SEQ ID NO 505
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 505
gctcattgct gctgc                                              15

<210> SEQ ID NO 506
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 506
ggaaggctca ttgctgc                                            17

<210> SEQ ID NO 507
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 507
ttttctcttc ttct                                               14

<210> SEQ ID NO 508
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 508
atcttattcc tttc                                               14

<210> SEQ ID NO 509
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 509
catcttattc cttt                                               14
```

```
<210> SEQ ID NO 510
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 510 tagttttttcc ttct                                                        14

<210> SEQ ID NO 511
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 511
tctagttttt cctt                                                         14

<210> SEQ ID NO 512
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 512
aactctagtt tttc                                                         14

<210> SEQ ID NO 513
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 513
gaactctagt tttt                                                         14

<210> SEQ ID NO 514
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 514
tgaactctag ttttt                                                        15

<210> SEQ ID NO 515
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 515
atgaactcta gttttt                                                       16

<210> SEQ ID NO 516
```

```
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 516
tgaactctag tttt                                                      14

<210> SEQ ID NO 517
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 517
atgaactcta gtttt                                                     15

<210> SEQ ID NO 518
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 518
atgaactcta gttt                                                      14

<210> SEQ ID NO 519
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 519
gcacacagta gtgc                                                      14

<210> SEQ ID NO 520
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 520
gcaggatcag aaaagc                                                    16

<210> SEQ ID NO 521
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 521
gcaggtagac aggc                                                      14

<210> SEQ ID NO 522
<211> LENGTH: 17
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 522
gcttgctcag gatctgc                                                      17

<210> SEQ ID NO 523
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 523
gcaagtccct ggtgc                                                        15

<210> SEQ ID NO 524
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 524
cctggagcaa gtcc                                                         14

<210> SEQ ID NO 525
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 525
cgtagtactc ttcgtcg                                                      17

<210> SEQ ID NO 526
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 526
cgtagtactc ttcg                                                         14

<210> SEQ ID NO 527
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 527
gtaaacctcc ttgg                                                         14

<210> SEQ ID NO 528
<211> LENGTH: 19
<212> TYPE: DNA
```

-continued

<213> ORGANISM: Artificial Sequence
<220> FEATURE:
<223> OTHER INFORMATION: Description of Artificial Sequence:
      antisense oligonucleotide

<400> SEQUENCE: 528
gtctattttg taaacctcc                                                    19

<210> SEQ ID NO 529
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 529
gcatgtctat tttgtaaacc                                                   20

<210> SEQ ID NO 530
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 530
ggcatcaagg taccc                                                        15

<210> SEQ ID NO 531
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 531
ggcatcaagg tacc                                                         14

<210> SEQ ID NO 532
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 532
gctttcacca aattggaagc                                                   20

<210> SEQ ID NO 533
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 533
gagaatctga tatagctc                                                     18

<210> SEQ ID NO 534
<211> LENGTH: 19
<212> TYPE: DNA
<213> ORGANISM: Artificial Sequence

```
<220> FEATURE:
<223> OTHER INFORMATION: Description of Artificial Sequence:
      antisense oligonucleotide

<400> SEQUENCE: 534
ggagatgtta aatctttgg                                              19

<210> SEQ ID NO 535
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 535
gctgtcgatg tagc                                                   14

<210> SEQ ID NO 536
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 536
ccaggttcct gtctttatgg                                             20

<210> SEQ ID NO 537
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 537
cagcagggac agtg                                                   14

<210> SEQ ID NO 538
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 538
cttgcttcta gttcttcac                                              19

<210> SEQ ID NO 539
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 539
gccatcaata cctgc                                                  15

<210> SEQ ID NO 540
<211> LENGTH: 15
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 540
ggtgccatca atacc                                                      15

<210> SEQ ID NO 541
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 541
ccactggtat atgtgg                                                     16

<210> SEQ ID NO 542
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 542
ggactttata gttttctg                                                   18

<210> SEQ ID NO 543
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 543
ctcaagtctg taggag                                                     16

<210> SEQ ID NO 544
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 544
ggtctgttgt gactc                                                      15

<210> SEQ ID NO 545
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 545
caattatcct gcacatttc                                                  19

<210> SEQ ID NO 546
<211> LENGTH: 16
<212> TYPE: DNA
<213> ORGANISM: Artificial Sequence
<220> FEATURE:
<223> OTHER INFORMATION: Description of Artificial Sequence:
``` antisense oligonucleotide

<400> SEQUENCE: 546
gcagcaatta tcctgc 16

<210> SEQ ID NO 547
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 547
ggcagcaatt atcc 14

<210> SEQ ID NO 548
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 548
ggttcgtgta tccatttcc 19

<210> SEQ ID NO 549
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 549
gcacagaagt tggc 14

<210> SEQ ID NO 550
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 550
ccagcacaga agttgg 16

<210> SEQ ID NO 551
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 551
gtgctgagtg tctg 14

<210> SEQ ID NO 552
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

```
<400> SEQUENCE: 552
cctgctgtgc tgagtg                                              16

<210> SEQ ID NO 553
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 553
gctcaggacc ctgc                                                14

<210> SEQ ID NO 554
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 554
gcagcaagga gaagc                                               15

<210> SEQ ID NO 555
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 555
ccaatgtagt agagaatgg                                           19

<210> SEQ ID NO 556
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 556
gctgcatttg caag                                                14

<210> SEQ ID NO 557
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 557
aaaaaagaaa tcaa                                                14

<210> SEQ ID NO 558
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide
```

```
<400> SEQUENCE: 558
aaaaaaagaa atcaa                                                       15

<210> SEQ ID NO 559
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 559
aaaaaaaaga aatcaa                                                      16

<210> SEQ ID NO 560
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 560
taaaaaaaag aaatcaa                                                     17

<210> SEQ ID NO 561
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 561
ataaaaaaaa gaaatcaa                                                    18

<210> SEQ ID NO 562
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 562
aataaaaaaa agaaatcaa                                                   19

<210> SEQ ID NO 563
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 563
gaataaaaaa aagaaat                                                     17

<210> SEQ ID NO 564
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 564
```
agaataaaaa aaagaaat                                                    18

<210> SEQ ID NO 565
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 565
cagaataaaa aaaa                                                        14

<210> SEQ ID NO 566
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 566
tcagaataaa aaaa                                                        14

<210> SEQ ID NO 567
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 567
ttgtttttaa aagt                                                        14

<210> SEQ ID NO 568
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 568
agttgttttt aaaa                                                        14

<210> SEQ ID NO 569
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 569
aagttgtttt taaaa                                                       15

<210> SEQ ID NO 570
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 570
aaagttgttt ttaaaa 16

<210> SEQ ID NO 571
<211> LENGTH: 17
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 571
aaaagttgtt tttaaaa 17

<210> SEQ ID NO 572
<211> LENGTH: 18
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 572
aaaaagttgt ttttaaaa 18

<210> SEQ ID NO 573
<211> LENGTH: 19
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 573
aaaaaagttg tttttaaaa 19

<210> SEQ ID NO 574
<211> LENGTH: 20
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 574
aaaaaaagtt gttttttaaaa 20

<210> SEQ ID NO 575
<211> LENGTH: 20
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 575
aaaaaaaagt tgtttttaaa 20

<210> SEQ ID NO 576
<211> LENGTH: 14
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 576
tttttaaaaa agtg 14

<210> SEQ ID NO 577
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 577 tttttttaaaa aagtg                                              15

<210> SEQ ID NO 578
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 578 atttttttaaa aaagtg                                             16

<210> SEQ ID NO 579
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 579
cattttttaa aaaagt                                              16

<210> SEQ ID NO 580
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 580
gcatttttta aaaaa                                               15

<210> SEQ ID NO 581
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 581
tgcatttttt aaaaaa                                              16

<210> SEQ ID NO 582
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 582
agcttatttt aaat                                                14

```
<210> SEQ ID NO 583
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 583
aagcttattt taaat                                                     15

<210> SEQ ID NO 584
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 584
taagcttatt ttaaat                                                    16

<210> SEQ ID NO 585
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 585
tgtaattatt agat                                                      14

<210> SEQ ID NO 586
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 586
atgtaattat tagat                                                     15

<210> SEQ ID NO 587
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 587
tgatgtaatt atta                                                      14

<210> SEQ ID NO 588
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 588
atgatgtaat tatta                                                     15
```

```
<210> SEQ ID NO 589
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 589
atggtattat ataa                                                        14

<210> SEQ ID NO 590
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 590
tatggtatta taaa                                                        15

<210> SEQ ID NO 591
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 591
ttatggtatt atataa                                                      16

<210> SEQ ID NO 592
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 592
tttatggtat tatataa                                                     17

<210> SEQ ID NO 593
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 593
atttatggta ttatataa                                                    18

<210> SEQ ID NO 594
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 594
aatcatatta gaaa                                                        14

<210> SEQ ID NO 595
```

```
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 595
ttacaatcat atta                                                        14

<210> SEQ ID NO 596
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 596
tttacaatca tatta                                                       15

<210> SEQ ID NO 597
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 597
ggcatgacgc ctttcc                                                      16

<210> SEQ ID NO 598
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 598
gcatgacgcc tttc                                                        14

<210> SEQ ID NO 599
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 599
gcctgacgag aggc                                                        14

<210> SEQ ID NO 600
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 600
ctcaagcctg acgag                                                       15

<210> SEQ ID NO 601
<211> LENGTH: 16
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 601
ccacagttcc tttttc                                                    16

<210> SEQ ID NO 602
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 602
gctgcaataa agatacag                                                  18

<210> SEQ ID NO 603
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 603
gctgcaataa agatac                                                    16

<210> SEQ ID NO 604
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 604
ggacactgat ttctatg                                                   17

<210> SEQ ID NO 605
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 605
gcattatcaa ctttgg                                                    16

<210> SEQ ID NO 606
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 606
acttttagca ccaatg                                                    16

<210> SEQ ID NO 607
<211> LENGTH: 19
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 607
ccaagaaact tttagcacc                                              19

<210> SEQ ID NO 608
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 608
ccagatcatc ttcc                                                   14

<210> SEQ ID NO 609
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 609
agtcaaggac acatag                                                 16

<210> SEQ ID NO 610
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 610
tctttgagca acatgg                                                 16

<210> SEQ ID NO 611
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 611
gggtataaca gctg                                                   14

<210> SEQ ID NO 612
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 612
gaggtgaacc attaatgg                                               18

<210> SEQ ID NO 613
<211> LENGTH: 16
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 613
tcttcgtatc gtttag                                                    16

<210> SEQ ID NO 614
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 614
tgttggatag tgttc                                                     15

<210> SEQ ID NO 615
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 615
gttgatcact tgctg                                                     15

<210> SEQ ID NO 616
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 616
ggattccatt actcg                                                     15

<210> SEQ ID NO 617
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 617
gacatatgaa aaatgttgtc                                                20

<210> SEQ ID NO 618
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 618
gccaataaag acatatg                                                   17

<210> SEQ ID NO 619
<211> LENGTH: 17
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 619
ccagaatcaa gattctg                                                      17

<210> SEQ ID NO 620
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 620
ctgttccaga atcaag                                                       16

<210> SEQ ID NO 621
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 621
gacaaatctg ttccagaatc                                                   20

<210> SEQ ID NO 622
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 622
ggaaagacaa atctgttcc                                                    19

<210> SEQ ID NO 623
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 623
gattaagagg acaagc                                                       16

<210> SEQ ID NO 624
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 624
ggaagattaa gagg                                                         14

<210> SEQ ID NO 625
<211> LENGTH: 18
<212> TYPE: DNA
<213> ORGANISM: Artificial Sequence
<220> FEATURE:
<223> OTHER INFORMATION: Description of Artificial Sequence:
``` antisense oligonucleotide

<400> SEQUENCE: 625
gcagtgtgat tattctgg                                              18

<210> SEQ ID NO 626
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 626
ggagaaagat acatatctg                                             19

<210> SEQ ID NO 627
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 627
ggagatctta cagg                                                  14

<210> SEQ ID NO 628
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 628
gcatttgcag tagaatttac                                            20

<210> SEQ ID NO 629
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 629
cagtgaaaga gagg                                                  14

<210> SEQ ID NO 630
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 630
gctagccgat acac                                                  14

<210> SEQ ID NO 631
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 631
ggaagatcct tgtatgc                                           17

<210> SEQ ID NO 632
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 632
gcatgaggaa gatcc                                             15

<210> SEQ ID NO 633
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 633
ggagtcattt ttgttg                                            16

<210> SEQ ID NO 634
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 634
ccaattgata ctaagattc                                         19

<210> SEQ ID NO 635
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 635
tcttttgagc acacg                                             15

<210> SEQ ID NO 636
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 636
ccttcagcac ttcttttg                                          18

<210> SEQ ID NO 637
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

```
<400> SEQUENCE: 637
ggttgcttcc ttcagc                                                    16

<210> SEQ ID NO 638
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 638
cagtggttta ggag                                                      14

<210> SEQ ID NO 639
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 639
cctgagatcc tcatttc                                                   17

<210> SEQ ID NO 640
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 640
ccaaggtcct gagatcc                                                   17

<210> SEQ ID NO 641
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 641
ggtgtacaca gtgtcc                                                    16

<210> SEQ ID NO 642
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 642
tatctttaat ttct                                                      14

<210> SEQ ID NO 643
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 643
```

```
tcttttgaat ataa                                               14

<210> SEQ ID NO 644
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 644
ttcttttgaa tataa                                              15

<210> SEQ ID NO 645
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 645
tttcttttga atataa                                             16

<210> SEQ ID NO 646
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 646
ttttcttttg aatataa                                            17

<210> SEQ ID NO 647
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 647
tttttctttt gaatataa                                           18

<210> SEQ ID NO 648
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 648
atttctatgt tttt                                               14

<210> SEQ ID NO 649
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 649
```

```
ttaaagaatt tatg                                                         14

<210> SEQ ID NO 650
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 650
gttaaagaat ttat                                                         14

<210> SEQ ID NO 651
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 651
agttaaagaa tttat                                                        15

<210> SEQ ID NO 652
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 652
aagttaaaga atttat                                                       16

<210> SEQ ID NO 653
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 653
taagttaaag aatttat                                                      17

<210> SEQ ID NO 654
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 654
tttagtaagt taaa                                                         14

<210> SEQ ID NO 655
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 655
ttttagtaag ttaaa                                                        15
```

<210> SEQ ID NO 656
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 656 atttcttttta gtaa                                                14

<210> SEQ ID NO 657
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 657
aatttctttt agtaa                                                15

<210> SEQ ID NO 658
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 658
atcaatttct ttta                                                 14

<210> SEQ ID NO 659
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 659
tatcaatttc tttta                                                15

<210> SEQ ID NO 660
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 660
aatatataag ttca                                                 14

<210> SEQ ID NO 661
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 661
aaatatataa gttca                                                15

```
<210> SEQ ID NO 662
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 662
caaatatata agtt                                                         14

<210> SEQ ID NO 663
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 663
tcaaatatat aagtt                                                        15

<210> SEQ ID NO 664
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 664
tgtcaaatat ataa                                                         14

<210> SEQ ID NO 665
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 665
aatttatttc agta                                                         14

<210> SEQ ID NO 666
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 666
aataaaaatg tgat                                                         14

<210> SEQ ID NO 667
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 667
taataaaaat gtgat                                                        15
```

```
<210> SEQ ID NO 668
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 668
tagctaataa aaat                                                      14

<210> SEQ ID NO 669
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 669
ttagctaata aaaat                                                     15

<210> SEQ ID NO 670
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 670
tttagctaat aaaaat                                                    16

<210> SEQ ID NO 671
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 671
aataaaatag tcaa                                                      14

<210> SEQ ID NO 672
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 672
taataaaata gtcaa                                                     15

<210> SEQ ID NO 673
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 673
ttaataaaat agtcaa                                                    16

<210> SEQ ID NO 674
```

```
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 674
tttaataaaa tagtcaa                                                17

<210> SEQ ID NO 675
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 675
gtttaataaa atagt                                                  15

<210> SEQ ID NO 676
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 676
agtttaataa aatagt                                                 16

<210> SEQ ID NO 677
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 677
gagtttaata aaata                                                  15

<210> SEQ ID NO 678
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 678
agagtttaat aaaata                                                 16

<210> SEQ ID NO 679
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 679
aataattctt gtat                                                   14

<210> SEQ ID NO 680
<211> LENGTH: 14
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 680
tatattacat tcat                                                          14

<210> SEQ ID NO 681
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 681
atctatatta catt                                                          14

<210> SEQ ID NO 682
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 682
ataaacattt ttca                                                          14

<210> SEQ ID NO 683
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 683
aataaacatt tttca                                                         15

<210> SEQ ID NO 684
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 684
aaataaacat ttttca                                                        16

<210> SEQ ID NO 685
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 685
gaaataaaca ttttt                                                         15

<210> SEQ ID NO 686
<211> LENGTH: 16
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 686
tgaaataaac attttt                                                      16

<210> SEQ ID NO 687
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 687
ttgaaataaa cattttt                                                     17

<210> SEQ ID NO 688
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 688
tttgaaataa acattttt                                                    18

<210> SEQ ID NO 689
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 689
ttttgaaata aacattttt                                                   19

<210> SEQ ID NO 690
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 690
tttttgaaat aaacattttt                                                  20

<210> SEQ ID NO 691
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 691 attttttgaaa taaacattttt                                                20

<210> SEQ ID NO 692
<211> LENGTH: 19
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 692
aatttttgaa ataaacatt                                                19

<210> SEQ ID NO 693
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 693 aaattttga ataaacatt                                                 20

<210> SEQ ID NO 694
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 694 aaaattttg aataaacat                                                 20

<210> SEQ ID NO 695
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 695
taaaattttt gaaataaaca                                               20

<210> SEQ ID NO 696
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 696
ataaaatttt tgaaataaac                                               20

<210> SEQ ID NO 697
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 697
tataaaattt ttgaaataaa                                               20

<210> SEQ ID NO 698
<211> LENGTH: 18
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 698
gtataaaatt tttgaaat                                                    18

<210> SEQ ID NO 699
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 699
ggtataaaat tttt                                                        14

<210> SEQ ID NO 700
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 700
aggtataaaa ttttt                                                       15

<210> SEQ ID NO 701
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 701
aaggtataaa attttt                                                      16

<210> SEQ ID NO 702
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 702
aaaggtataa aatttt                                                      17

<210> SEQ ID NO 703
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 703
aaaaggtata aaattttt                                                    18

<210> SEQ ID NO 704
<211> LENGTH: 19
<212> TYPE: DNA
<213> ORGANISM: Artificial Sequence
<220> FEATURE:
<223> OTHER INFORMATION: Description of Artificial Sequence:
```

-continued antisense oligonucleotide

<400> SEQUENCE: 704
taaaaggtat aaaattttt                                          19

<210> SEQ ID NO 705
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 705
ataaaaggta taaaattttt                                         20

<210> SEQ ID NO 706
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 706
tttagaaaga tttt                                               14

<210> SEQ ID NO 707
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 707
aagataaatt tctt                                               14

<210> SEQ ID NO 708
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 708
taagataaat ttctt                                              15

<210> SEQ ID NO 709
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 709
ttaagataaa tttctt                                             16

<210> SEQ ID NO 710
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

```
<400> SEQUENCE: 710
tttaagataa atttctt                                              17

<210> SEQ ID NO 711
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 711
ttttaagata aatttctt                                             18

<210> SEQ ID NO 712
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 712
tttttaagat aaatttctt                                            19

<210> SEQ ID NO 713
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 713
atttttaaga taaatttctt                                           20

<210> SEQ ID NO 714
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 714
tatttttaag ataaatttct                                           20

<210> SEQ ID NO 715
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 715
ttatttttaa gataaatt                                             18

<210> SEQ ID NO 716
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide
```

-continued

<400> SEQUENCE: 716 tttatttta agataaatt                                                19

<210> SEQ ID NO 717
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 717
ctttattttt aagataaat                                               19

<210> SEQ ID NO 718
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 718
tctttatttt taagataaat                                              20

<210> SEQ ID NO 719
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 719
atctttattt ttaagataaa                                              20

<210> SEQ ID NO 720
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 720
atctttattt ttaa                                                    14

<210> SEQ ID NO 721
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 721
gatctttatt tttaa                                                   15

<210> SEQ ID NO 722
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 722

```
agatctttat tttaa                                                    16

<210> SEQ ID NO 723
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 723
tagatcttta tttttaa                                                  17

<210> SEQ ID NO 724
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 724
aatcatcatt aatt                                                     14

<210> SEQ ID NO 725
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 725
aaatcatcat taatt                                                    15

<210> SEQ ID NO 726
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 726
aaaatcatca ttaatt                                                   16

<210> SEQ ID NO 727
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 727
taaaatcatc attaatt                                                  17

<210> SEQ ID NO 728
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 728
```
ttaaaatcat cattaatt                                              18

<210> SEQ ID NO 729
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 729
tttaaaatca tcattaatt                                             19

<210> SEQ ID NO 730
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 730
atttaaaatc atcattaatt                                            20

<210> SEQ ID NO 731
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 731
aatttaaaat catcattaa                                             19

<210> SEQ ID NO 732
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 732
gaatttaaaa tcat                                                  14

<210> SEQ ID NO 733
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 733
tgaatttaaa atcat                                                 15

<210> SEQ ID NO 734
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 734
ttaaaatagg aaat                                                  14

```
<210> SEQ ID NO 735
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 735
aatttctctt taaa                                                      14

<210> SEQ ID NO 736
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 736
aaatttctct ttaaa                                                     15

<210> SEQ ID NO 737
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 737
taaaattttg aatg                                                      14

<210> SEQ ID NO 738
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 738
ctaaaatttt gaat                                                      14

<210> SEQ ID NO 739
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 739
tttgctaaaa tttt                                                      14

<210> SEQ ID NO 740
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 740
atatgaaaaa tgtt                                                      14
```

```
<210> SEQ ID NO 741
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 741
ttttaaatta agca                                                      14

<210> SEQ ID NO 742
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 742
ttgtaaaaat caaa                                                      14

<210> SEQ ID NO 743
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 743
tttgtaaaaa tcaaa                                                     15

<210> SEQ ID NO 744
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 744
tttgataaaa cttt                                                      14

<210> SEQ ID NO 745
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 745
atgttttatc attt                                                      14

<210> SEQ ID NO 746
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 746
aatgttttat cattt                                                     15
```

```
<210> SEQ ID NO 747
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 747
aaatgtttta tcattt                                                          16

<210> SEQ ID NO 748
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 748
taaatgtttt atcattt                                                         17

<210> SEQ ID NO 749
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 749
tctaaatgtt ttat                                                            14

<210> SEQ ID NO 750
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 750
ttctaaatgt tttat                                                           15

<210> SEQ ID NO 751
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 751
taagatcaaa taaa                                                            14

<210> SEQ ID NO 752
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 752
ataagatcaa ataaa                                                           15

<210> SEQ ID NO 753
```

```
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 753
aataagatca aataaa                                                       16

<210> SEQ ID NO 754
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 754
taataagatc aaataaa                                                      17

<210> SEQ ID NO 755
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 755
ttaataagat caaataaa                                                     18

<210> SEQ ID NO 756
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 756
tttaataaga tcaaataaa                                                    19

<210> SEQ ID NO 757
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 757
ttgtttaata agat                                                         14

<210> SEQ ID NO 758
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 758
attgtttaat aagat                                                        15

<210> SEQ ID NO 759
<211> LENGTH: 14
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 759
tgattgttta ataa                                                      14

<210> SEQ ID NO 760
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 760
ttgattgttt aataa                                                     15

<210> SEQ ID NO 761
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 761
tttgattgtt taataa                                                    16

<210> SEQ ID NO 762
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 762
ttttataaaa cagt                                                      14

<210> SEQ ID NO 763
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 763
tttttataaa acagt                                                     15

<210> SEQ ID NO 764
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 764
ttttttataa aacagt                                                    16

<210> SEQ ID NO 765
<211> LENGTH: 15
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 765
cttttttata aaaca                                                     15

<210> SEQ ID NO 766
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 766 actttttat aaaaca                                                     16

<210> SEQ ID NO 767
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 767
cactttttta taaaa                                                     15

<210> SEQ ID NO 768
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 768
acactttttt ataaaa                                                    16

<210> SEQ ID NO 769
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 769 tacactttt tataaaa                                                    17

<210> SEQ ID NO 770
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 770
atacactttt ttataaaa                                                  18

<210> SEQ ID NO 771
<211> LENGTH: 14
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 771
attttgaatt taag                                                        14

<210> SEQ ID NO 772
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 772
gattttgaat ttaa                                                        14

<210> SEQ ID NO 773
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 773
tgattttgaa tttaa                                                       15

<210> SEQ ID NO 774
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 774
atgattttga atttaa                                                      16

<210> SEQ ID NO 775
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 775
aatgattttg aatttaa                                                     17

<210> SEQ ID NO 776
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 776
ataatagaat cata                                                        14

<210> SEQ ID NO 777
<211> LENGTH: 15
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 777
tataatagaa tcata                                                      15

<210> SEQ ID NO 778
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 778
tataatagaa tcat                                                       14

<210> SEQ ID NO 779
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 779
tactataata gaat                                                       14

<210> SEQ ID NO 780
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 780
atactataat agaat                                                      15

<210> SEQ ID NO 781
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 781
aatactataa tagaat                                                     16

<210> SEQ ID NO 782
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 782
agaatactat aata                                                       14

<210> SEQ ID NO 783
<211> LENGTH: 15
<212> TYPE: DNA
<213> ORGANISM: Artificial Sequence
<220> FEATURE:
<223> OTHER INFORMATION: Description of Artificial Sequence:
```

-continued antisense oligonucleotide

<400> SEQUENCE: 783
tagaatacta taata                                    15

<210> SEQ ID NO 784
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 784
atagaatact ataata                                   16

<210> SEQ ID NO 785
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 785
tatagaatac tataata                                  17

<210> SEQ ID NO 786
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 786
ttatagaata ctataata                                 18

<210> SEQ ID NO 787
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 787
aatatttgtt ttca                                     14

<210> SEQ ID NO 788
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 788
aaatatttgt tttca                                    15

<210> SEQ ID NO 789
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

```
<400> SEQUENCE: 789
aaaatatttg ttttca                                                     16

<210> SEQ ID NO 790
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 790
caaaatattt gtttt                                                      15

<210> SEQ ID NO 791
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 791
aaattttata tgga                                                       14

<210> SEQ ID NO 792
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 792
tgaaatttta tatg                                                       14

<210> SEQ ID NO 793
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 793
ctgaaatttt atat                                                       14

<210> SEQ ID NO 794
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 794
tctgaaattt tatat                                                      15

<210> SEQ ID NO 795
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide
```

```
<400> SEQUENCE: 795
ttctgaaatt ttatat                                                      16

<210> SEQ ID NO 796
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 796
atctgattta tttt                                                        14

<210> SEQ ID NO 797
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 797
aagatattaa atgt                                                        14

<210> SEQ ID NO 798
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 798
tgaagatatt aaat                                                        14

<210> SEQ ID NO 799
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 799
ataaataaca atga                                                        14

<210> SEQ ID NO 800
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 800
tataaataac aatga                                                       15

<210> SEQ ID NO 801
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 801
```
gtataaataa caat                                                         14

<210> SEQ ID NO 802
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 802
tgtataaata acaat                                                        15

<210> SEQ ID NO 803
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 803
ttgtataaat aacaat                                                       16

<210> SEQ ID NO 804
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 804
tcttgtataa ataa                                                         14

<210> SEQ ID NO 805
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 805
atcttgtata aataa                                                        15

<210> SEQ ID NO 806
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 806
aatcttgtat aaataa                                                       16

<210> SEQ ID NO 807
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 807 acaactttt aaat 14

<210> SEQ ID NO 808
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 808
tacaactttt taaat 15

<210> SEQ ID NO 809
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 809
tacaactttt taaa 14

<210> SEQ ID NO 810
<211> LENGTH: 21
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 810 cgggggttt tgggcggcat g 21

<210> SEQ ID NO 811
<211> LENGTH: 23
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 811
ttttcggggg gttttgggcg gca 23

<210> SEQ ID NO 812
<211> LENGTH: 19
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 812 tcgggggtt ttgggcggc 19

<210> SEQ ID NO 813
<211> LENGTH: 24
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 813
ggtggcggcc gttttcggg gggt 24

```
<210> SEQ ID NO 814
<211> LENGTH: 23
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 814
ccgggggttc cgcggcggca gcg                                         23

<210> SEQ ID NO 815
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 815 cggggttcc gcggcgg                                                 17

<210> SEQ ID NO 816
<211> LENGTH: 23
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 816
ggcggcggtg ccgggggttc cgc                                         23

<210> SEQ ID NO 817
<211> LENGTH: 22
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 817 ggaggggcg gcggcggcgg tg                                           22

<210> SEQ ID NO 818
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 818
gggggcggcg gcggcgg                                                17

<210> SEQ ID NO 819
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 819
ggggcggcgg cggcg                                                  15
```

```
<210> SEQ ID NO 820
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 820 aggggggcctg gtggaag                                                      17

<210> SEQ ID NO 821
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 821 taggggggcct ggtg                                                         14

<210> SEQ ID NO 822
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 822 gtaggggggcc tggt                                                         14

<210> SEQ ID NO 823
<211> LENGTH: 26
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 823
gaggtattgg tgacaaggta gggggc                                             26

<210> SEQ ID NO 824
<211> LENGTH: 26
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 824
tcttcagggg tgaaatatag atgttc                                             26

<210> SEQ ID NO 825
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 825
ggactcttca ggggtg                                                        16
```

```
<210> SEQ ID NO 826
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 826
tcggactata ctgc                                                      14

<210> SEQ ID NO 827
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 827
cagttcggac tatact                                                    16

<210> SEQ ID NO 828
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 828
aagcctaaga cgca                                                      14

<210> SEQ ID NO 829
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 829
gcccaagttc aaca                                                      14

<210> SEQ ID NO 830
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 830
tgaaaagtcg cggt                                                      14

<210> SEQ ID NO 831
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 831
ggttaattaa gatgcctc                                                  18

<210> SEQ ID NO 832
```

```
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 832
tctctaagag cgca                                                          14

<210> SEQ ID NO 833
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 833
acgtgaggtt agtttg                                                        16

<210> SEQ ID NO 834
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 834
cacgtgaggt tagt                                                          14

<210> SEQ ID NO 835
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 835
catagaacag tccg                                                          14

<210> SEQ ID NO 836
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 836
cagtcataga acagtc                                                        16

<210> SEQ ID NO 837
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 837
ctttgcagtc atagaaca                                                      18

<210> SEQ ID NO 838
<211> LENGTH: 14
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 838
tgcagtcata gaac                                                     14

<210> SEQ ID NO 839
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 839
ggtcgtttcc atct                                                     14

<210> SEQ ID NO 840
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 840
catagaaggt cgtttc                                                   16

<210> SEQ ID NO 841
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 841
cgtcatagaa ggtc                                                     14

<210> SEQ ID NO 842
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 842
catcgtcata gaagg                                                    15

<210> SEQ ID NO 843
<211> LENGTH: 24
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 843
ggacgggagg aacgaggcgt tgag                                          24

<210> SEQ ID NO 844
<211> LENGTH: 14
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 844
tagccataag gtcc                                                        14

<210> SEQ ID NO 845
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 845
ggttactgta gcca                                                        14

<210> SEQ ID NO 846
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 846
ggttactgta gcca                                                        14

<210> SEQ ID NO 847
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 847
agttcttggc gcggaggt                                                    18

<210> SEQ ID NO 848
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 848
aggtgaggag gtccgagt                                                    18

<210> SEQ ID NO 849
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 849
tggactggat tatcag                                                      16

<210> SEQ ID NO 850
<211> LENGTH: 18
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 850
gtggtggtga tgtgcccg                                              18

<210> SEQ ID NO 851
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 851
tgtcacgttc ttgg                                                  14

<210> SEQ ID NO 852
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 852
ctcatctgtc acgt                                                  14

<210> SEQ ID NO 853
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 853
cgaagccctc ggcgaacc                                              18

<210> SEQ ID NO 854
<211> LENGTH: 24
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 854
gcgtgttctg gctgtgcagt tcgg                                       24

<210> SEQ ID NO 855
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 855
ctgccccgtt gacc                                                  14

<210> SEQ ID NO 856
<211> LENGTH: 14
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 856
aggtttgcgt agac                                                          14

<210> SEQ ID NO 857
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 857
ggttgaagtt gctg                                                          14

<210> SEQ ID NO 858
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 858
ctgggttgaa gttg                                                          14

<210> SEQ ID NO 859
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 859
tgctgcacgg gcatctgctg                                                    20

<210> SEQ ID NO 860
<211> LENGTH: 27
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 860
ggcactgtct gaggctcctc cttcagg                                            27

<210> SEQ ID NO 861
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 861
actccatgtc gatg                                                          14

<210> SEQ ID NO 862
<211> LENGTH: 16
<212> TYPE: DNA
<213> ORGANISM: Artificial Sequence
<220> FEATURE:
<223> OTHER INFORMATION: Description of Artificial Sequence:
``` antisense oligonucleotide

<400> SEQUENCE: 862
ctctccgcct tgatcc					16

<210> SEQ ID NO 863
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 863
gttcctcatg cgcttc					16

<210> SEQ ID NO 864
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 864
ctgagctttc aagg						14

<210> SEQ ID NO 865
<211> LENGTH: 26
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 865
gcgattctct ccagcttcct ttttcg				26

<210> SEQ ID NO 866
<211> LENGTH: 30
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 866
ctgagctttc aaggttttca cttttcctc				30

<210> SEQ ID NO 867
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 867
tccctgagca tgtt						14

<210> SEQ ID NO 868
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide -continued

```
<400> SEQUENCE: 868
tctgtttaag ctgtgc                                                     16

<210> SEQ ID NO 869
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 869
ctttctgttt aagctgtg                                                   18

<210> SEQ ID NO 870
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 870
ggttcatgac tttctg                                                     16

<210> SEQ ID NO 871
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 871
cgtggttcat gact                                                       14

<210> SEQ ID NO 872
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 872
actgttaacg tggttc                                                     16

<210> SEQ ID NO 873
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 873
ccactgttaa cgtg                                                       14

<210> SEQ ID NO 874
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide
```

```
<400> SEQUENCE: 874
cccactgtta acgt                                                    14

<210> SEQ ID NO 875
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 875
agcatgagtt ggca                                                    14

<210> SEQ ID NO 876
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 876
gcgttagcat gagt                                                    14

<210> SEQ ID NO 877
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 877
gtttgcaact gctg                                                    14

<210> SEQ ID NO 878
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 878
caaaatgttt gcaactgc                                                18

<210> SEQ ID NO 879
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 879
tccattttag tgcacatc                                                18

<210> SEQ ID NO 880
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 880
```

```
ctgttccatt ttagtgca                                                  18

<210> SEQ ID NO 881
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 881
gtgtatgagt cgtc                                                      14

<210> SEQ ID NO 882
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 882
ctgtgtatga gtcg                                                      14

<210> SEQ ID NO 883
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 883
cgtagctgtg tatg                                                      14

<210> SEQ ID NO 884
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 884
tcgtgtagag agag                                                      14

<210> SEQ ID NO 885
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 885
agtttgtagt cgtgtaga                                                  18

<210> SEQ ID NO 886
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 886
```
gtttgtagtc gtgtag 16

<210> SEQ ID NO 887
<211> LENGTH: 14
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 887
agtttgtagt cgtg 14

<210> SEQ ID NO 888
<211> LENGTH: 14
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 888
ggagtttgta gtcg 14

<210> SEQ ID NO 889
<211> LENGTH: 16
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 889
tcaggagttt gtagtc 16

<210> SEQ ID NO 890
<211> LENGTH: 18
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 890
gtttcaggag tttgtagt 18

<210> SEQ ID NO 891
<211> LENGTH: 14
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 891
tcggtttcag gagt 14

<210> SEQ ID NO 892
<211> LENGTH: 14
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 892
ttgagactcc ggta 14

```
<210> SEQ ID NO 893
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 893
accagaaaag tagctg                                                      16

<210> SEQ ID NO 894
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 894
cctgaccaga aaag                                                        14

<210> SEQ ID NO 895
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 895
attcaggcgt tcca                                                        14

<210> SEQ ID NO 896
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 896
ggtaaaagta ctgtcc                                                      16

<210> SEQ ID NO 897
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 897
gggtaaaagt actgtc                                                      16

<210> SEQ ID NO 898
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 898
gcacctccac cgctgcca                                                    18
```

```
<210> SEQ ID NO 899
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 899
ctcctgctcc tcggtgac                                                18

<210> SEQ ID NO 900
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 900
gctttgacaa agcc                                                    14

<210> SEQ ID NO 901
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 901
cttgtgcaga tcgt                                                    14

<210> SEQ ID NO 902
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 902
tcatcttgtg cagatc                                                  16

<210> SEQ ID NO 903
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 903
gttcatcttg tgcaga                                                  16

<210> SEQ ID NO 904
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 904
cgtggttcat cttg                                                    14
```

```
<210> SEQ ID NO 905
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 905
tcacgtggtt catc                                                          14

<210> SEQ ID NO 906
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 906
ggttggtgta aacg                                                          14

<210> SEQ ID NO 907
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 907
tacgagctcc cggtcccgac                                                    20

<210> SEQ ID NO 908
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 908
tagctgatgg tggt                                                          14

<210> SEQ ID NO 909
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 909
tccttgaagg tgga                                                          14

<210> SEQ ID NO 910
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 910
tcttccatgt tgatgg                                                        16

<210> SEQ ID NO 911
```

-continued

```
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 911
ctttgatgcg ctct                                                      14

<210> SEQ ID NO 912
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 912
ctccactttg atgc                                                      14

<210> SEQ ID NO 913
<211> LENGTH: 30
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 913
gctccagctt ccgcttccgg cacttggtgg                                     30

<210> SEQ ID NO 914
<211> LENGTH: 30
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 914
ggccttgagc gtcttcacct tgtcctccag                                     30

<210> SEQ ID NO 915
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 915
tgaccttctg tttgag                                                    16

<210> SEQ ID NO 916
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 916
catgaccttc tgtttg                                                    16

<210> SEQ ID NO 917
<211> LENGTH: 14
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 917
gtcatgacct tctg                                                       14

<210> SEQ ID NO 918
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 918
cgagaacatc atcg                                                       14

<210> SEQ ID NO 919
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 919
gtagtctgcg ttga                                                       14

<210> SEQ ID NO 920
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 920
gctgcagcgg gaggatgacg                                                 20

<210> SEQ ID NO 921
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 921
agtaagagag gctatc                                                     16

<210> SEQ ID NO 922
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 922
gtagtaagag aggc                                                       14

<210> SEQ ID NO 923
<211> LENGTH: 14
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 923
ggtagtaaga gagg                                                14

<210> SEQ ID NO 924
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 924
gtgagtggta gtaaga                                              16

<210> SEQ ID NO 925
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 925
gtccgtgcag aagtcctg                                            18

<210> SEQ ID NO 926
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 926
gaatgaagtt ggcact                                              16

<210> SEQ ID NO 927
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 927
ggaatgaagt tggc                                                14

<210> SEQ ID NO 928
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 928
gggaatgaag ttgg                                                14

<210> SEQ ID NO 929
<211> LENGTH: 30
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 929
gctgcaccag ccactgcagg tccggactgg                                        30

<210> SEQ ID NO 930
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 930
tcatggtctt cacaac                                                       16

<210> SEQ ID NO 931
<211> LENGTH: 30
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 931
caatgctctg cgctcggcct cctgtcatgg                                        30

<210> SEQ ID NO 932
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 932
ctagagttcc tcac                                                         14

<210> SEQ ID NO 933
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 933
gagtacgcta gagt                                                         14

<210> SEQ ID NO 934
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 934
gaagagtacg ctag                                                         14

<210> SEQ ID NO 935
<211> LENGTH: 28
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 935
ctgcttccca cccagccccc acattccc                                          28

<210> SEQ ID NO 936
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 936
ttcatcctct gtactgggct                                                   20

<210> SEQ ID NO 937
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 937
gttacggatg tgca                                                         14

<210> SEQ ID NO 938
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 938
cagttacgga tgtg                                                         14

<210> SEQ ID NO 939
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 939
ccagttacgg atgt                                                         14

<210> SEQ ID NO 940
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 940
agagtctgag ttgg                                                         14

<210> SEQ ID NO 941
<211> LENGTH: 14
<212> TYPE: DNA
<213> ORGANISM: Artificial Sequence
<220> FEATURE:
<223> OTHER INFORMATION: Description of Artificial Sequence:
``` antisense oligonucleotide

<400> SEQUENCE: 941
gtgagactca gagt                                                              14

<210> SEQ ID NO 942
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 942
tcttagggtg agac                                                              14

<210> SEQ ID NO 943
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 943
gagagtactt cttagg                                                            16

<210> SEQ ID NO 944
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 944
ggaagaaact atgagagt                                                          18

<210> SEQ ID NO 945
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 945
cttagggaag aactatg                                                           17

<210> SEQ ID NO 946
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 946
cggtaagaaa cttagg                                                            16

<210> SEQ ID NO 947
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

```
<400> SEQUENCE: 947
agcatgcggt aaga                                                    14

<210> SEQ ID NO 948
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 948
gtctgaaagc atgc                                                    14

<210> SEQ ID NO 949
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 949
agaacaaaga agagcc                                                  16

<210> SEQ ID NO 950
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 950
caagagaaca aagaagag                                                18

<210> SEQ ID NO 951
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 951
cagcaagaga acaaag                                                  16

<210> SEQ ID NO 952
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 952
tcctcagcaa gaga                                                    14

<210> SEQ ID NO 953
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide
```

```
<400> SEQUENCE: 953
aggtgtgact tgca                                                    14

<210> SEQ ID NO 954
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 954
gaataggtgt gacttg                                                  16

<210> SEQ ID NO 955
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 955
cagaataggt gtgact                                                  16

<210> SEQ ID NO 956
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 956
gcagaatagg tgtg                                                    14

<210> SEQ ID NO 957
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 957
cagttgcaga ataggt                                                  16

<210> SEQ ID NO 958
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 958
gaaaccattt ctgacc                                                  16

<210> SEQ ID NO 959
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 959
```

```
tgtgaaacca tttctgac                                              18

<210> SEQ ID NO 960
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 960
cactgtgaaa ccatttct                                              18

<210> SEQ ID NO 961
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 961
ccactgtgaa acca                                                  14

<210> SEQ ID NO 962
<211> LENGTH: 30
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 962
agaactggct cctgcagctt ccctgcttcc                                 30

<210> SEQ ID NO 963
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 963
cacctccatt caccc                                                 15

<210> SEQ ID NO 964
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 964
cagtaaaagt gtctgc                                                16

<210> SEQ ID NO 965
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 965
```

```
cgacattcag taaaagtg                                                   18
```

<210> SEQ ID NO 966
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 966

```
gaccgacatt cagt                                                       14
```

<210> SEQ ID NO 967
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 967

```
cttctggaga taactaga                                                   18
```

<210> SEQ ID NO 968
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 968

```
catcttattc ctttccct                                                   18
```

<210> SEQ ID NO 969
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 969

```
cagccatctt attcct                                                     16
```

<210> SEQ ID NO 970
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 970

```
tgcagccatc ttattc                                                     16
```

<210> SEQ ID NO 971
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 971

```
gagtgtatca gtcag                                                      15
```

<210> SEQ ID NO 972
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 972
ggagtgtatc agtc                                                    14

<210> SEQ ID NO 973
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 973
cttggagtgt atcagt                                                  16

<210> SEQ ID NO 974
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 974
acagagtacc tacc                                                    14

<210> SEQ ID NO 975
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 975
ccaactttcc cttaag                                                  16

<210> SEQ ID NO 976
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 976
ccttatgctc aatctc                                                  16

<210> SEQ ID NO 977
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 977
gtcttactca aggg                                                    14

```
<210> SEQ ID NO 978
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 978
acagtcttac tcaagg                                                     16

<210> SEQ ID NO 979
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 979
cataagacac agtcttac                                                   18

<210> SEQ ID NO 980
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 980
gaaagcataa gacacagt                                                   18

<210> SEQ ID NO 981
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 981
ggaaagcata agacac                                                     16

<210> SEQ ID NO 982
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 982
agggataaag gaaagc                                                     16

<210> SEQ ID NO 983
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 983
cctgtataca gagg                                                       14
```

```
<210> SEQ ID NO 984
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 984
tgtctcctgt atacag                                                    16

<210> SEQ ID NO 985
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 985
catcttctag ttggtc                                                    16

<210> SEQ ID NO 986
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 986
ctcatcttct agttgg                                                    16

<210> SEQ ID NO 987
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 987
cttctcatct tctagttg                                                  18

<210> SEQ ID NO 988
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 988
caaagcagac ttctca                                                    16

<210> SEQ ID NO 989
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 989
ctgcaaagca gact                                                      14

<210> SEQ ID NO 990
```

```
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 990
ctagtttttc cttctcct                                                 18

<210> SEQ ID NO 991
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 991
tctagttttt ccttctcc                                                 18

<210> SEQ ID NO 992
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 992
caggatgaac tctagt                                                   16

<210> SEQ ID NO 993
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 993
tcgtagaagg tcgt                                                     14

<210> SEQ ID NO 994
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 994
agggttactg tagc                                                     14

<210> SEQ ID NO 995
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 995
gtagtggtga tgtg                                                     14

<210> SEQ ID NO 996
<211> LENGTH: 14
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 996
cgtcgtagaa ggtc                                                      14

<210> SEQ ID NO 997
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 997
tttcgtgcac atcc                                                      14

<210> SEQ ID NO 998
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 998
agtttgtagt cgtgaaga                                                  18

<210> SEQ ID NO 999
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 999
cgagaacatc atgg                                                      14

<210> SEQ ID NO 1000
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1000
gtagtaggaa aggc                                                      14

<210> SEQ ID NO 1001
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1001
ggtagtagga aagg                                                      14

<210> SEQ ID NO 1002
<211> LENGTH: 14
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 1002
ggaatggtag tagg                                                      14

<210> SEQ ID NO 1003
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1003
ggtcattgag aagag                                                     15

<210> SEQ ID NO 1004
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1004
gctaatgttc ttgacc                                                    16

<210> SEQ ID NO 1005
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1005
gccaaggtcc tcat                                                      14

<210> SEQ ID NO 1006
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1006
ggagtctatc tcca                                                      14

<210> SEQ ID NO 1007
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1007
ccaaagaatc ctgact                                                    16

<210> SEQ ID NO 1008
<211> LENGTH: 14
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 1008
cacatgctta gtgg                                                         14

<210> SEQ ID NO 1009
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1009
ctcgtaaatg accg                                                         14

<210> SEQ ID NO 1010
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1010
aggaatctcg taaatgac                                                     18

<210> SEQ ID NO 1011
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1011
cagcagcgat tcat                                                         14

<210> SEQ ID NO 1012
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1012
ggagatcatc aaagga                                                       16

<210> SEQ ID NO 1013
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1013
ctcagcaatg gtca                                                         14

<210> SEQ ID NO 1014
<211> LENGTH: 14
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 1014
gatctcgaac acct                                                      14

<210> SEQ ID NO 1015
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1015
cacaatctcg atctttct                                                  18

<210> SEQ ID NO 1016
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1016
ccttcttaaa gattggct                                                  18

<210> SEQ ID NO 1017
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1017
cacataccaa ctgg                                                      14

<210> SEQ ID NO 1018
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1018
agcttgatgt gagg                                                      14

<210> SEQ ID NO 1019
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1019
gaagttgtag cttgatgt                                                  18

<210> SEQ ID NO 1020
<211> LENGTH: 16
<212> TYPE: DNA
<213> ORGANISM: Artificial Sequence
<220> FEATURE:
<223> OTHER INFORMATION: Description of Artificial Sequence:
```

-continued antisense oligonucleotide

<400> SEQUENCE: 1020
gcttgaagtt gtagct                                                        16

<210> SEQ ID NO 1021
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1021
ctgcttgaag ttgtag                                                        16

<210> SEQ ID NO 1022
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1022
gacacaactc ctct                                                            14

<210> SEQ ID NO 1023
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1023
tcctttgata gacacaac                                                   18

<210> SEQ ID NO 1024
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1024
ctcgtttgat agacac                                                     16

<210> SEQ ID NO 1025
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1025
ggttagcaca cact                                                         14

<210> SEQ ID NO 1026
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1026
ggtaacggtt agca                                            14

<210> SEQ ID NO 1027
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1027
cgtaacacat ttagaagc                                        18

<210> SEQ ID NO 1028
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1028
ctcatccgta acac                                            14

<210> SEQ ID NO 1029
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1029
ccggtaagta ttgtagtt                                        18

<210> SEQ ID NO 1030
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1030
ggtgtatttc cttgac                                          16

<210> SEQ ID NO 1031
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1031
acataccaac tggtgt                                          16

<210> SEQ ID NO 1032
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

```
<400> SEQUENCE: 1032
gtccctatac gaac                                              14

<210> SEQ ID NO 1033
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1033
ttcatgtctg tgcc                                              14

<210> SEQ ID NO 1034
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1034
gtaggtgagt tcca                                              14

<210> SEQ ID NO 1035
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1035
gttgtgagcg atga                                              14

<210> SEQ ID NO 1036
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1036
catagttgtc ctcaaaga                                          18

<210> SEQ ID NO 1037
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1037
ggcatagttg tcct                                              14

<210> SEQ ID NO 1038
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1038
```

```
cattgtctag cacg                                                     14
```

<210> SEQ ID NO 1039
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1039

```
ctccattgtc tagc                                                     14
```

<210> SEQ ID NO 1040
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1040

```
gtattgttca gcgg                                                     14
```

<210> SEQ ID NO 1041
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1041

```
tcaagatctc tgtgag                                                   16
```

<210> SEQ ID NO 1042
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1042

```
cacaaaatcg tgtcct                                                   16
```

<210> SEQ ID NO 1043
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1043

```
tccttccaca aaatcg                                                   16
```

<210> SEQ ID NO 1044
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1044
gtggaagatg tcct                                                        14

<210> SEQ ID NO 1045
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1045
tcttgtggaa gatgtc                                                      16

<210> SEQ ID NO 1046
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1046
tctatcagtg tgagag                                                      16

<210> SEQ ID NO 1047
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1047
ggttggtgtc tatc                                                        14

<210> SEQ ID NO 1048
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1048
acatcggaga acag                                                        14

<210> SEQ ID NO 1049
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1049
ccttacacat cgga                                                        14

<210> SEQ ID NO 1050
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1050
acaatcctca gaactc                                                      16

<210> SEQ ID NO 1051
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1051
gctctgacaa tcct                                                         14

<210> SEQ ID NO 1052
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1052
tggttgaagt ggag                                                         14

<210> SEQ ID NO 1053
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1053
ctgtggttga agtg                                                         14

<210> SEQ ID NO 1054
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1054
gttgtaggtg acca                                                         14

<210> SEQ ID NO 1055
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1055
ctgtgttgta ggtg                                                         14

<210> SEQ ID NO 1056
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1056
gactcaaacg tgtc                                                         14

```
<210> SEQ ID NO 1057
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1057
catggactca aacg                                                          14

<210> SEQ ID NO 1058
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1058
cgaatgtata ccgg                                                          14

<210> SEQ ID NO 1059
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1059
ccgaatgtat accg                                                          14

<210> SEQ ID NO 1060
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1060
gccgaatgta tacc                                                          14

<210> SEQ ID NO 1061
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1061
gtagttgtag ggac                                                          14

<210> SEQ ID NO 1062
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1062
tagaaaggta gttgtagg                                                      18
```

```
<210> SEQ ID NO 1063
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1063
gtagaaaggt agttgtag                                                18

<210> SEQ ID NO 1064
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1064
cgtagaaagg tagttg                                                  16

<210> SEQ ID NO 1065
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1065
ccgtagaaag gtag                                                    14

<210> SEQ ID NO 1066
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1066
gaccatagca cact                                                    14

<210> SEQ ID NO 1067
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1067
ggatattggc actg                                                    14

<210> SEQ ID NO 1068
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1068
cctggatatt ggca                                                    14

<210> SEQ ID NO 1069
```

```
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1069
gctcccaaag atct                                                    14

<210> SEQ ID NO 1070
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1070
cccatcaaag ctct                                                    14

<210> SEQ ID NO 1071
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1071
caaacacttg gagc                                                    14

<210> SEQ ID NO 1072
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1072
gtctcaaaca cttgga                                                  16

<210> SEQ ID NO 1073
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1073
gagtctcaaa cacttg                                                  16

<210> SEQ ID NO 1074
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1074
gtaacctgtg atctct                                                  16

<210> SEQ ID NO 1075
<211> LENGTH: 14
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1075
ggtaacctgt gatc                                                          14

<210> SEQ ID NO 1076
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1076
gtataggtaa cctgtg                                                        16

<210> SEQ ID NO 1077
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1077
tgagatgtat aggtaacc                                                      18

<210> SEQ ID NO 1078
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1078
tgctgagatg tatagg                                                        16

<210> SEQ ID NO 1079
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1079
ccatgctgag atgt                                                          14

<210> SEQ ID NO 1080
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1080
ggattacttg cagg                                                          14

<210> SEQ ID NO 1081
<211> LENGTH: 16
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 1081
tgttatggtg gatgag                                                    16

<210> SEQ ID NO 1082
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1082
ggtgttatgg tgga                                                      14

<210> SEQ ID NO 1083
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1083
gcagttgaca cact                                                      14

<210> SEQ ID NO 1084
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1084
agtactcggc attc                                                      14

<210> SEQ ID NO 1085
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1085
cattcacata ctccct                                                    16

<210> SEQ ID NO 1086
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1086
tccaaaacag gtcact                                                    16

<210> SEQ ID NO 1087
<211> LENGTH: 14
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 1087
ggtccttata gtgg                                                     14

<210> SEQ ID NO 1088
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1088
cagaatgcca acca                                                     14

<210> SEQ ID NO 1089
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1089
acgagaatgc caac                                                     14

<210> SEQ ID NO 1090
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1090
gatcccaaag acca                                                     14

<210> SEQ ID NO 1091
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1091
tcgcttgatg agga                                                     14

<210> SEQ ID NO 1092
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1092
catcgtgtac ttcc                                                     14

<210> SEQ ID NO 1093
<211> LENGTH: 14
<212> TYPE: DNA
<213> ORGANISM: Artificial Sequence
<220> FEATURE:
```

-continued

<223> OTHER INFORMATION: Description of Artificial Sequence:
      antisense oligonucleotide

<400> SEQUENCE: 1093
gcatcgtgta cttc                                                        14

<210> SEQ ID NO 1094
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1094
actgtgccaa aagc                                                        14

<210> SEQ ID NO 1095
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1095
cttgtagact gtgc                                                        14

<210> SEQ ID NO 1096
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1096
cccttgtaga ctgt                                                        14

<210> SEQ ID NO 1097
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1097
tcaacacttt gatggc                                                      16

<210> SEQ ID NO 1098
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1098
ccctcaacac tttg                                                        14

<210> SEQ ID NO 1099
<211> LENGTH: 16
<212> TYPE: DNA
<213> ORGANISM: Artificial Sequence
<220> FEATURE:
<223> OTHER INFORMATION: Description of Artificial Sequence:

antisense oligonucleotide

<400> SEQUENCE: 1099
gtgttttccc tcaaca                                                        16

<210> SEQ ID NO 1100
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1100
gtatgcttcg tctaag                                                        16

<210> SEQ ID NO 1101
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1101
cgtatgcttc gtct                                                          14

<210> SEQ ID NO 1102
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1102
ccatcacgta tgct                                                          14

<210> SEQ ID NO 1103
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1103
gcataagctg tgtc                                                          14

<210> SEQ ID NO 1104
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1104
catggtctaa gagg                                                          14

<210> SEQ ID NO 1105
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

```
<400> SEQUENCE: 1105
caatctgcat acacca                                              16

<210> SEQ ID NO 1106
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1106
ggcaatctgc atac                                                14

<210> SEQ ID NO 1107
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1107
ctgtctcgtc aatg                                                14

<210> SEQ ID NO 1108
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1108
cataactcca cacatc                                              16

<210> SEQ ID NO 1109
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1109
agtcacacca taactc                                              16

<210> SEQ ID NO 1110
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1110
acagtcacac cataac                                              16

<210> SEQ ID NO 1111
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide
```

```
<400> SEQUENCE: 1111
ccccaaaagt catc                                                         14

<210> SEQ ID NO 1112
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1112
tcgtaaggtt tggc                                                         14

<210> SEQ ID NO 1113
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1113
gatcccatcg taag                                                         14

<210> SEQ ID NO 1114
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1114
caatggtgca gatg                                                         14

<210> SEQ ID NO 1115
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1115
gacatcaatg gtgc                                                         14

<210> SEQ ID NO 1116
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1116
gtagacatca atggtg                                                       16

<210> SEQ ID NO 1117
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1117
```
catgatcatg tagacatc                                              18

<210> SEQ ID NO 1118
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1118
ccatgatcat gtagac                                                16

<210> SEQ ID NO 1119
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1119
catttgacca tgatcatg                                              18

<210> SEQ ID NO 1120
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1120
ccaacatttg accatg                                                16

<210> SEQ ID NO 1121
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1121
tcatccaaca tttgacca                                              18

<210> SEQ ID NO 1122
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1122
gagtcaatca tccaacat                                              18

<210> SEQ ID NO 1123
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1123

-continued cagagtcaat catcca    16

<210> SEQ ID NO 1124
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1124
ccgacattca gagt    14

<210> SEQ ID NO 1125
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1125
gaattcagac accaac    16

<210> SEQ ID NO 1126
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1126
gatgaccaca aagc    14

<210> SEQ ID NO 1127
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1127
ccatcaaata catcgg    16

<210> SEQ ID NO 1128
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1128
tcaccatcaa atacatcg    18

<210> SEQ ID NO 1129
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1129
caacgtagcc atca    14

<210> SEQ ID NO 1130
<211> LENGTH: 14
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 1130
acgtctttga cgac                                                      14

<210> SEQ ID NO 1131
<211> LENGTH: 18
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 1131
caaaaacgtc tttgacga                                                  18

<210> SEQ ID NO 1132
<211> LENGTH: 16
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 1132
ggcaaaaacg tctttg                                                    16

<210> SEQ ID NO 1133
<211> LENGTH: 16
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 1133
caaaggcaaa aacgtc                                                    16

<210> SEQ ID NO 1134
<211> LENGTH: 14
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 1134
gtgtcaagta ctcg                                                      14

<210> SEQ ID NO 1135
<211> LENGTH: 16
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 1135
gtaatagagg ttgtcg                                                    16

-continued

```
<210> SEQ ID NO 1136
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1136
cccagtaata gagg                                                         14

<210> SEQ ID NO 1137
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1137
catggtgctc actg                                                         14

<210> SEQ ID NO 1138
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1138
gtgcctgtac gtac                                                         14

<210> SEQ ID NO 1139
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1139
tgcaggtgga tagt                                                         14

<210> SEQ ID NO 1140
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1140
catgtcgata gtcttgca                                                     18

<210> SEQ ID NO 1141
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1141
gtcgatagtc ttgc                                                         14
```

<210> SEQ ID NO 1142
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1142
ccatgtcgat agtc                                                        14

<210> SEQ ID NO 1143
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1143
ctccatgtcg atag                                                        14

<210> SEQ ID NO 1144
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1144
cttggacagg atct                                                        14

<210> SEQ ID NO 1145
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1145
tgctgttgta cagg                                                        14

<210> SEQ ID NO 1146
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1146
gtgctgttgt acag                                                        14

<210> SEQ ID NO 1147
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1147
ttggcgtagt agtc                                                        14

<210> SEQ ID NO 1148

```
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1148
tccaccatta gcac                                                          14

<210> SEQ ID NO 1149
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1149
gatttcgttg tggg                                                          14

<210> SEQ ID NO 1150
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1150
gtcatagatt tcgttgtg                                                      18

<210> SEQ ID NO 1151
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1151
tgtactctgc ttgaac                                                        16

<210> SEQ ID NO 1152
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1152
gtgtactctg cttg                                                          14

<210> SEQ ID NO 1153
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1153
tgctgtgtgt actc                                                          14

<210> SEQ ID NO 1154
<211> LENGTH: 18
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1154
ctgatgtgtt gaagaaca                                                18

<210> SEQ ID NO 1155
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1155
ctctgatgtg ttgaag                                                  16

<210> SEQ ID NO 1156
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1156
gctctgatgt gttg                                                    14

<210> SEQ ID NO 1157
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1157
gagctctgat gtgt                                                    14

<210> SEQ ID NO 1158
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1158
cacttttaac ttgagcct                                                18

<210> SEQ ID NO 1159
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1159
ctccactttt aacttgag                                                18

<210> SEQ ID NO 1160
<211> LENGTH: 18
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 1160
tgctgtattt ctggtaca                                                 18

<210> SEQ ID NO 1161
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1161
ccaggaattg ttgc                                                     14

<210> SEQ ID NO 1162
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1162
ttgctgaggt atcg                                                     14

<210> SEQ ID NO 1163
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1163
gataaccact ctgg                                                     14

<210> SEQ ID NO 1164
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1164
caaaagataa ccactctg                                                 18

<210> SEQ ID NO 1165
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1165
cggtgacatc aaaag                                                    15

<210> SEQ ID NO 1166
<211> LENGTH: 14
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 1166
cctcaatttc ccct                                                        14

<210> SEQ ID NO 1167
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1167
gttatccctg ctgt                                                        14

<210> SEQ ID NO 1168
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1168
gcagtgtgtt atcc                                                        14

<210> SEQ ID NO 1169
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1169
gatgtccact tgca                                                        14

<210> SEQ ID NO 1170
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1170
tagtgaaccc gttg                                                        14

<210> SEQ ID NO 1171
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1171
tgccatgaat ggtg                                                        14

<210> SEQ ID NO 1172
<211> LENGTH: 16
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 1172
gttcatgcca tgaatg                                                   16

<210> SEQ ID NO 1173
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1173
catgagaagc agga                                                     14

<210> SEQ ID NO 1174
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1174
gctttgcaga tgct                                                     14

<210> SEQ ID NO 1175
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1175
gagctttgca gatg                                                     14

<210> SEQ ID NO 1176
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1176
tagttggtgt ccag                                                     14

<210> SEQ ID NO 1177
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1177
ctgaagcaat agttgg                                                   16

<210> SEQ ID NO 1178
<211> LENGTH: 18
<212> TYPE: DNA
<213> ORGANISM: Artificial Sequence
<220> FEATURE:
<223> OTHER INFORMATION: Description of Artificial Sequence:
```

```
      antisense oligonucleotide

<400> SEQUENCE: 1178
agctgaagca atagttgg                                              18

<210> SEQ ID NO 1179
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1179
ggagctgaag caat                                                  14

<210> SEQ ID NO 1180
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1180
caatgtacag ctgc                                                  14

<210> SEQ ID NO 1181
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1181
ggaagtcaat gtacag                                                16

<210> SEQ ID NO 1182
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1182
cggaagtcaa tgtac                                                 15

<210> SEQ ID NO 1183
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1183
gcggaagtca atgt                                                  14

<210> SEQ ID NO 1184
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide
```

```
<400> SEQUENCE: 1184
agttggcatg gtag                                                    14

<210> SEQ ID NO 1185
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1185
gcagaagttg gcat                                                    14

<210> SEQ ID NO 1186
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1186
ctccaaatgt aggg                                                    14

<210> SEQ ID NO 1187
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1187
accttgctgt actg                                                    14

<210> SEQ ID NO 1188
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1188
tgctggttgt acag                                                    14

<210> SEQ ID NO 1189
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1189
ggttatgctg gttg                                                    14

<210> SEQ ID NO 1190
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide
```

```
-continued

<400> SEQUENCE: 1190
gtagtacacg atgg                                                    14

<210> SEQ ID NO 1191
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1191
cgtagtacac gatg                                                    14

<210> SEQ ID NO 1192
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1192
cacgtagtac acga                                                    14

<210> SEQ ID NO 1193
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1193
catgttggac agct                                                    14

<210> SEQ ID NO 1194
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1194
gcacgatcat gttg                                                    14

<210> SEQ ID NO 1195
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1195
cacacagtag tgca                                                    14

<210> SEQ ID NO 1196
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1196
```
gatcagaaaa gcgc                                                         14

<210> SEQ ID NO 1197
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1197
accgtgacca gatg                                                         14

<210> SEQ ID NO 1198
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1198
gtagacaggc tgag                                                         14

<210> SEQ ID NO 1199
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1199
tatcgagtgt gctg                                                         14

<210> SEQ ID NO 1200
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1200
ttgcgcatga actg                                                         14

<210> SEQ ID NO 1201
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1201
ttgctcagga tctg                                                         14

<210> SEQ ID NO 1202
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1202

-continued actggtgagc ttca                                                14

<210> SEQ ID NO 1203
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1203
gctcaggata gtct                                                14

<210> SEQ ID NO 1204
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1204
tgtagatgga aatcacct                                            18

<210> SEQ ID NO 1205
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1205
tggtgctgtt gtag                                                14

<210> SEQ ID NO 1206
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1206
ttctcctgga gcaa                                                14

<210> SEQ ID NO 1207
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1207
tactcttcgt cgct                                                14

<210> SEQ ID NO 1208
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1208
cttggcgtag tact                                                14

<210> SEQ ID NO 1209
<211> LENGTH: 18
<212> TYPE: DNA
<213> ORGANISM: Artificial Sequence
<220> FEATURE:
<223> OTHER INFORMATION: Description of Artificial Sequence: antisense oligonucleotide

<400> SEQUENCE: 1209
cggcatgtct attttgta                                                 18

<210> SEQ ID NO 1210
<211> LENGTH: 14
<212> TYPE: DNA
<213> ORGANISM: Artificial Sequence
<220> FEATURE:
<223> OTHER INFORMATION: Description of Artificial Sequence: antisense oligonucleotide

<400> SEQUENCE: 1210
cgggatggca tttt                                                     14

<210> SEQ ID NO 1211
<211> LENGTH: 14
<212> TYPE: DNA
<213> ORGANISM: Artificial Sequence
<220> FEATURE:
<223> OTHER INFORMATION: Description of Artificial Sequence: antisense oligonucleotide

<400> SEQUENCE: 1211
ctgtagaaag tggg                                                     14

<210> SEQ ID NO 1212
<211> LENGTH: 18
<212> TYPE: DNA
<213> ORGANISM: Artificial Sequence
<220> FEATURE:
<223> OTHER INFORMATION: Description of Artificial Sequence: antisense oligonucleotide

<400> SEQUENCE: 1212
acaattctga agtagggt                                                 18

<210> SEQ ID NO 1213
<211> LENGTH: 18
<212> TYPE: DNA
<213> ORGANISM: Artificial Sequence
<220> FEATURE:
<223> OTHER INFORMATION: Description of Artificial Sequence: antisense oligonucleotide

<400> SEQUENCE: 1213
attgctgaga cgtcaaat                                                 18

<210> SEQ ID NO 1214
<211> LENGTH: 14
<212> TYPE: DNA
<213> ORGANISM: Artificial Sequence
<220> FEATURE:
<223> OTHER INFORMATION: Description of Artificial Sequence: antisense oligonucleotide

<400> SEQUENCE: 1214
tctccattgc tgag                                                     14

```
<210> SEQ ID NO 1215
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1215
tcaccaaatt ggaagcat                                             18

<210> SEQ ID NO 1216
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1216
ctctgaactc tgct                                                 14

<210> SEQ ID NO 1217
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1217
aacgaaagac tctgaact                                             18

<210> SEQ ID NO 1218
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1218
tgggttctgc aaac                                                 14

<210> SEQ ID NO 1219
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1219
ctggcttttg ggtt                                                 14

<210> SEQ ID NO 1220
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1220
gttgttcagg cact                                                 14
```

```
<210> SEQ ID NO 1221
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1221
tctgatatag ctcaatcc                                                  18

<210> SEQ ID NO 1222
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1222
tctttggact tgagaatc                                                  18

<210> SEQ ID NO 1223
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1223
tgggttggag atgt                                                      14

<210> SEQ ID NO 1224
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1224
tgctgtcgat gtag                                                      14

<210> SEQ ID NO 1225
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1225
acaactttgc tgtcga                                                    16

<210> SEQ ID NO 1226
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1226
attcgccttc tgct                                                      14

<210> SEQ ID NO 1227
```

```
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1227
gaaggagagc catt                                                      14

<210> SEQ ID NO 1228
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1228
tcagttacat cgaagg                                                    16

<210> SEQ ID NO 1229
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1229
tgaagccatt catgaaca                                                  18

<210> SEQ ID NO 1230
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1230
tcctgtcttt atggtg                                                    16

<210> SEQ ID NO 1231
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1231
aaatcccagg ttcc                                                      14

<210> SEQ ID NO 1232
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1232
ggacagtgta agcttatt                                                  18

<210> SEQ ID NO 1233
<211> LENGTH: 16
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1233
gtacaaaagt gcagca                                                     16

<210> SEQ ID NO 1234
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1234
tagatggtac aaaagtgc                                                   18

<210> SEQ ID NO 1235
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1235
cacttttatt tgggatgatg                                                 20

<210> SEQ ID NO 1236
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1236
gcaaatcttg cttctagt                                                   18

<210> SEQ ID NO 1237
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1237
gtgccatcaa tacc                                                       14

<210> SEQ ID NO 1238
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1238
ggtatatgtg gagg                                                       14

<210> SEQ ID NO 1239
<211> LENGTH: 14
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 1239
tctgatcacc actg                                                        14

<210> SEQ ID NO 1240
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1240
tcctagtgga ctttatag                                                    18

<210> SEQ ID NO 1241
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1241
tttttcctag tggact                                                      16

<210> SEQ ID NO 1242
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1242
caataacatt agcagg                                                      16

<210> SEQ ID NO 1243
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1243
aagtctgtag gagg                                                        14

<210> SEQ ID NO 1244
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1244
tctgttgtga ctcaag                                                      16

<210> SEQ ID NO 1245
<211> LENGTH: 14
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 1245
gttggtctgt tgtg                                                        14

<210> SEQ ID NO 1246
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1246
caaagcacgc ttct                                                        14

<210> SEQ ID NO 1247
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1247
tttctaaagc aataggcc                                                    18

<210> SEQ ID NO 1248
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1248
gcaattatcc tgcaca                                                      16

<210> SEQ ID NO 1249
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1249
acgtaggcag caat                                                        14

<210> SEQ ID NO 1250
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1250
atcaatgtaa agtggacg                                                    18

<210> SEQ ID NO 1251
<211> LENGTH: 14
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 1251
ctagatccct cttg                                                          14

<210> SEQ ID NO 1252
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1252
ccatttccac ccta                                                          14

<210> SEQ ID NO 1253
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1253
tgggttcgtg tatc                                                          14

<210> SEQ ID NO 1254
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1254
tggcattgta ccct                                                          14

<210> SEQ ID NO 1255
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1255
tccagcacag aagt                                                          14

<210> SEQ ID NO 1256
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1256
ataaatacgg gcatgc                                                        16

<210> SEQ ID NO 1257
<211> LENGTH: 14
<212> TYPE: DNA
<213> ORGANISM: Artificial Sequence
<220> FEATURE:
<223> OTHER INFORMATION: Description of Artificial Sequence:
```

```
      antisense oligonucleotide

<400> SEQUENCE: 1257
agtgtctgaa ctcc                                                    14

<210> SEQ ID NO 1258
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1258
tgtgctgagt gtct                                                    14

<210> SEQ ID NO 1259
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1259
ataagctcag gacc                                                    14

<210> SEQ ID NO 1260
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1260
aggagaagca gatg                                                    14

<210> SEQ ID NO 1261
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1261
agcaaggaga agca                                                    14

<210> SEQ ID NO 1262
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1262
aatcttggga cacg                                                    14

<210> SEQ ID NO 1263
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide
```

```
<400> SEQUENCE: 1263
tagagaatgg ttagaggt                                                  18

<210> SEQ ID NO 1264
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1264
gttttgccaa tgtagtag                                                  18

<210> SEQ ID NO 1265
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1265
cttgggtgtt ttgc                                                      14

<210> SEQ ID NO 1266
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1266
gcaagacttt acaatc                                                    16

<210> SEQ ID NO 1267
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1267
gcatttgcaa gactttac                                                  18

<210> SEQ ID NO 1268
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1268
tttagctgca tttgcaag                                                  18

<210> SEQ ID NO 1269
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide
```

```
<400> SEQUENCE: 1269
gccacttttc caag                                                 14

<210> SEQ ID NO 1270
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1270
ttggtcttgc cact                                                 14

<210> SEQ ID NO 1271
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1271
cagcacacag tagt                                                 14

<210> SEQ ID NO 1272
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1272
cgatagtctt gcag                                                 14

<210> SEQ ID NO 1273
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1273
ctttcaccaa attggaag                                             18

<210> SEQ ID NO 1274
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1274
caccaaattg gaagc                                                15

<210> SEQ ID NO 1275
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1275
```
tcaccaaatt ggaagc                                                    16

<210> SEQ ID NO 1276
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1276
ctctggcttt tggg                                                      14

<210> SEQ ID NO 1277
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1277
cggcatgtct attttg                                                    16

<210> SEQ ID NO 1278
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1278
cactacagac gagc                                                      14

<210> SEQ ID NO 1279
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1279
cgtgcactac agacg                                                     15

<210> SEQ ID NO 1280
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1280
ggaacagttc gtcc                                                      14

<210> SEQ ID NO 1281
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1281

-continued gaacagttcg tccatg                          16

<210> SEQ ID NO 1282
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1282
ccagagtttc ggttc                           15

<210> SEQ ID NO 1283
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1283
ctaggactgg gacag                           15

<210> SEQ ID NO 1284
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1284
cgcacttgta gcg                             13

<210> SEQ ID NO 1285
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1285
ctcgcacttg tagc                            14

<210> SEQ ID NO 1286
<211> LENGTH: 11
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1286
gcacttgtag c                               11

<210> SEQ ID NO 1287
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1287
gcgcactgtc cctg                            14

<210> SEQ ID NO 1288
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1288
ccagggagat gcgc                                                      14

<210> SEQ ID NO 1289
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1289
gccggtgagg agg                                                       13

<210> SEQ ID NO 1290
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1290
ccggtgagga ggg                                                       13

<210> SEQ ID NO 1291
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1291
cggttcactc ggc                                                       13

<210> SEQ ID NO 1292
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1292
gagtttcggt tcactc                                                    16

<210> SEQ ID NO 1293
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1293
ggcacgattg tcaaag                                                    16

```
<210> SEQ ID NO 1294
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1294
caggcgtcac cccc                                                       14

<210> SEQ ID NO 1295
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1295
gcaggcgtca ccc                                                        13

<210> SEQ ID NO 1296
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1296
ctccctccta agc                                                        13

<210> SEQ ID NO 1297
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1297
ccctcctaag cgg                                                        13

<210> SEQ ID NO 1298
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1298
cgagtccgcg ttcg                                                       14

<210> SEQ ID NO 1299
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1299
catcttctgc cattc                                                      15
```

```
<210> SEQ ID NO 1300
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1300
gtgttttccc accag                                                        15

<210> SEQ ID NO 1301
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1301
ggttttggtt cactag                                                       16

<210> SEQ ID NO 1302
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1302
gcatcttcac gtctcc                                                       16

<210> SEQ ID NO 1303
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1303
cttcacgtct cctgtc                                                       16

<210> SEQ ID NO 1304
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1304
gtcaccgcgt agtc                                                         14

<210> SEQ ID NO 1305
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1305
caaataggca aggtc                                                        15

<210> SEQ ID NO 1306
```

```
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1306
cttgcaaata ggcaag                                                    16

<210> SEQ ID NO 1307
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1307
tgcttgcaaa tagg                                                      14

<210> SEQ ID NO 1308
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1308
ctgcttgcaa atagg                                                     15

<210> SEQ ID NO 1309
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1309
gcaggtggat attt                                                      14

<210> SEQ ID NO 1310
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1310
ctgctgttgg cag                                                       13

<210> SEQ ID NO 1311
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1311
cactagtttc caagt                                                     15

<210> SEQ ID NO 1312
<211> LENGTH: 15
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1312
gttttggttc actag                                                   15

<210> SEQ ID NO 1313
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1313
ctttgatttc aggatag                                                 17

<210> SEQ ID NO 1314
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1314
gcacttcttc tttatct                                                 17

<210> SEQ ID NO 1315
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1315
ccaagtcaga tttcc                                                   15

<210> SEQ ID NO 1316
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1316
gtttccaagt cagatttc                                                18

<210> SEQ ID NO 1317
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1317
ggttcactag tttcc                                                   15

<210> SEQ ID NO 1318
<211> LENGTH: 16
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 1318
ggttttggtt cactag                                                    16

<210> SEQ ID NO 1319
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1319
ccgaaaaatt gggca                                                     15

<210> SEQ ID NO 1320
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1320
ccgaaaaatt ggg                                                       13

<210> SEQ ID NO 1321
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1321
ctatccgaaa aattgg                                                    16

<210> SEQ ID NO 1322
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1322
gttgataatg tcatcag                                                   17

<210> SEQ ID NO 1323
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1323
ctcatgttga taatgtc                                                   17

<210> SEQ ID NO 1324
<211> LENGTH: 14
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 1324
ctgtcaccgc gtag                                                        14

<210> SEQ ID NO 1325
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1325
cgtctcctgt caccg                                                       15

<210> SEQ ID NO 1326
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1326
cttcacgtct cctg                                                        14

<210> SEQ ID NO 1327
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1327
gagaacttta tcatgtc                                                     17

<210> SEQ ID NO 1328
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1328
gctatatgca ggg                                                         13

<210> SEQ ID NO 1329
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1329
ccagctgcta tatgcagg                                                    18

<210> SEQ ID NO 1330
<211> LENGTH: 16
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 1330
aggctaaatt ttgcct                                                    16

<210> SEQ ID NO 1331
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1331
ggctaaattt tgcc                                                      14

<210> SEQ ID NO 1332
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1332
ggctaaattt tgccttc                                                   17

<210> SEQ ID NO 1333
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1333
gcaggctaaa ttttgcc                                                   17

<210> SEQ ID NO 1334
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1334
gagttaccca agcg                                                      14

<210> SEQ ID NO 1335
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1335
cagagttacc caagcg                                                    16

<210> SEQ ID NO 1336
<211> LENGTH: 14
<212> TYPE: DNA
<213> ORGANISM: Artificial Sequence
<220> FEATURE:
<223> OTHER INFORMATION: Description of Artificial Sequence:
``` antisense oligonucleotide

<400> SEQUENCE: 1336
cagagttacc caag                                                    14

<210> SEQ ID NO 1337
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1337
acagagttac ccaag                                                   15

<210> SEQ ID NO 1338
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1338
ggtgcaaaac agag                                                    14

<210> SEQ ID NO 1339
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1339
ctaggtgcaa aacag                                                   15

<210> SEQ ID NO 1340
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1340
gagaacttta tcatgtcc                                                18

<210> SEQ ID NO 1341
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1341
gctagatgaa tggc                                                    14

<210> SEQ ID NO 1342
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1342
gcaaacatgg caggc                                                            15

<210> SEQ ID NO 1343
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1343
cagcaaacat ggca                                                             14

<210> SEQ ID NO 1344
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1344
gcagcaaaca tggc                                                             14

<210> SEQ ID NO 1345
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1345
agcagcaaac atgg                                                             14

<210> SEQ ID NO 1346
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1346
cagcagcaaa catg                                                             14

<210> SEQ ID NO 1347
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1347
agcagcagca aaca                                                             14

<210> SEQ ID NO 1348
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide -continued

```
<400> SEQUENCE: 1348
cagcagcagc aaaca                                                    15

<210> SEQ ID NO 1349
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1349
cagcagcagc aaac                                                     14

<210> SEQ ID NO 1350
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1350
caccagcagc agca                                                     14

<210> SEQ ID NO 1351
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1351
gcattgacgt cagc                                                     14

<210> SEQ ID NO 1352
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1352
gatgttgtcg tgctc                                                    15

<210> SEQ ID NO 1353
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1353
tgagatgttg tcgtgct                                                  17

<210> SEQ ID NO 1354
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1354
```
tgagatgttg tcgtg                                                15

<210> SEQ ID NO 1355
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1355
gccaatgaga tgttg                                                15

<210> SEQ ID NO 1356
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1356
ctgccaatga gatg                                                 14

<210> SEQ ID NO 1357
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1357
cacatgggca tcac                                                 14

<210> SEQ ID NO 1358
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1358
tgtccacatg ggca                                                 14

<210> SEQ ID NO 1359
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1359
gtactgtcca catg                                                 14

<210> SEQ ID NO 1360
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1360

```
cagctgctat atgc                                                         14
```

<210> SEQ ID NO 1361
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1361

```
gttctccacc aggg                                                         14
```

<210> SEQ ID NO 1362
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1362

```
agttctccac cagg                                                         14
```

<210> SEQ ID NO 1363
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1363

```
caaagttctc caccag                                                       16
```

<210> SEQ ID NO 1364
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1364

```
ccaagagtca tccagg                                                       16
```

<210> SEQ ID NO 1365
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1365

```
cccaagagtc atcc                                                         14
```

<210> SEQ ID NO 1366
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1366

```
cctgcatttt cccaag                                                       16
```

<210> SEQ ID NO 1367
<211> LENGTH: 14
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 1367
tcctgcattt tccc                                                          14

<210> SEQ ID NO 1368
<211> LENGTH: 15
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 1368
gccatatcta gaggc                                                         15

<210> SEQ ID NO 1369
<211> LENGTH: 14
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 1369
tcacatcttc agcc                                                          14

<210> SEQ ID NO 1370
<211> LENGTH: 16
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 1370
gcttcacatc ttcagc                                                        16

<210> SEQ ID NO 1371
<211> LENGTH: 15
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 1371
cagcttcaca tcttc                                                         15

<210> SEQ ID NO 1372
<211> LENGTH: 17
<212> TYPE: DNA
<213> ORGANISM: Artificial Sequence
<220> FEATURE:
<223> OTHER INFORMATION: Description of Artificial Sequence:
    antisense oligonucleotide

<400> SEQUENCE: 1372
gtaacttata cagctgc                                                       17

```
<210> SEQ ID NO 1373
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1373
ccagtttttg tctgg                                                   15

<210> SEQ ID NO 1374
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1374
ccatttgtct cagg                                                    14

<210> SEQ ID NO 1375
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1375
gtgtagccca tttg                                                    14

<210> SEQ ID NO 1376
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1376
gcttcggtgt agcc                                                    14

<210> SEQ ID NO 1377
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1377
gatcacttca attgcttc                                                18

<210> SEQ ID NO 1378
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1378
cttgtggagg cagg                                                    14
```

```
<210> SEQ ID NO 1379
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1379
gctgccttgt ggag                                                      14

<210> SEQ ID NO 1380
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1380
ctatttgctg ccttgtgg                                                  18

<210> SEQ ID NO 1381
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1381
ggatgtctcc acgc                                                      14

<210> SEQ ID NO 1382
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1382
ggaaggatgt ctcc                                                      14

<210> SEQ ID NO 1383
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1383
tgcggaagga tgtc                                                      14

<210> SEQ ID NO 1384
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1384
gtttgcggaa ggatgtc                                                   17

<210> SEQ ID NO 1385
```

-continued

```
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1385
gctgagtttg cgga                                                     14

<210> SEQ ID NO 1386
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1386
ggtaaagctg agtttg                                                   16

<210> SEQ ID NO 1387
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1387
tcggtaaagc tgag                                                     14

<210> SEQ ID NO 1388
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1388
gactcggtaa agctg                                                    15

<210> SEQ ID NO 1389
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1389
agagactcgg taaagc                                                   16

<210> SEQ ID NO 1390
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1390
gaaattgtca gcaggc                                                   16

<210> SEQ ID NO 1391
<211> LENGTH: 15
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1391
gaaattgtca gcagg                                                          15

<210> SEQ ID NO 1392
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1392
ggaaattgtc agcagg                                                         16

<210> SEQ ID NO 1393
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1393
ggaaattgtc agcag                                                          15

<210> SEQ ID NO 1394
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1394
gggaaattgt cagc                                                           14

<210> SEQ ID NO 1395
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1395
gtgtgggaaa ttgtc                                                          15

<210> SEQ ID NO 1396
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1396
ggtttacacg gtgtg                                                          15

<210> SEQ ID NO 1397
<211> LENGTH: 15
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 1397
gctttggttt acacg                                                    15

<210> SEQ ID NO 1398
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1398
gcacctttgg gatgc                                                    15

<210> SEQ ID NO 1399
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1399
ccaggttctg cttcc                                                    15

<210> SEQ ID NO 1400
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1400
gctctgtcta gtggc                                                    15

<210> SEQ ID NO 1401
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1401
actctccatg tctc                                                     14

<210> SEQ ID NO 1402
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1402
caactctcca tgtctc                                                   16

<210> SEQ ID NO 1403
<211> LENGTH: 14
<212> TYPE: DNA
<213> ORGANISM: Artificial Sequence
```

-continued

```
<220> FEATURE:
<223> OTHER INFORMATION: Description of Artificial Sequence:
      antisense oligonucleotide

<400> SEQUENCE: 1403
caactctcca tgtc                                                        14

<210> SEQ ID NO 1404
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1404
agcaactctc catg                                                        14

<210> SEQ ID NO 1405
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1405
gtagcaactc tccatg                                                      16

<210> SEQ ID NO 1406
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1406
gtagcaactc tcca                                                        14

<210> SEQ ID NO 1407
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1407
ggttgtagca actctcc                                                     17

<210> SEQ ID NO 1408
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1408
cgggcagtcc tcca                                                        14

<210> SEQ ID NO 1409
<211> LENGTH: 13
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 1409
gcaccgggca gtc                                                          13

<210> SEQ ID NO 1410
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1410
aggcaccggg cag                                                          13

<210> SEQ ID NO 1411
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1411
gtgtgttacc aggtc                                                        15

<210> SEQ ID NO 1412
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1412
tgtgtgttac caggt                                                        15

<210> SEQ ID NO 1413
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1413
tgggtcactg tgtg                                                         14

<210> SEQ ID NO 1414
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1414
cagactgtgg gcatg                                                        15

<210> SEQ ID NO 1415
<211> LENGTH: 16
<212> TYPE: DNA
<213> ORGANISM: Artificial Sequence
<220> FEATURE:
<223> OTHER INFORMATION: Description of Artificial Sequence:
```

-continued

```
      antisense oligonucleotide

<400> SEQUENCE: 1415
cccaccagac tgtggg                                                     16

<210> SEQ ID NO 1416
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1416
ccaccagact gtgg                                                       14

<210> SEQ ID NO 1417
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1417
tgcccaccag actg                                                       14

<210> SEQ ID NO 1418
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1418
cggcttcctc ccc                                                        13

<210> SEQ ID NO 1419
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1419
ccttgtcttc cacc                                                       14

<210> SEQ ID NO 1420
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1420
accgaggctg ccac                                                       14

<210> SEQ ID NO 1421
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide
```

<400> SEQUENCE: 1421
ggaagaaacc gagg					14

<210> SEQ ID NO 1422
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1422
gggaagaaac cgag					14

<210> SEQ ID NO 1423
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1423
ggccatctgc gcc					13

<210> SEQ ID NO 1424
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1424
gcggccatct gcg					13

<210> SEQ ID NO 1425
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1425
gtggcggcca tctg					14

<210> SEQ ID NO 1426
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1426
accgtggcgg ccat					14

<210> SEQ ID NO 1427
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1427
gccgctcaat cttcatc                                                  17

<210> SEQ ID NO 1428
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1428
cttcatcttg tgatagg                                                  17

<210> SEQ ID NO 1429
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1429
gctcaatctt catcttg                                                  17

<210> SEQ ID NO 1430
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1430
cagaaacact gttacag                                                  17

<210> SEQ ID NO 1431
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1431
cagttgcaga aacactg                                                  17

<210> SEQ ID NO 1432
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1432
gtttcagttg cagaaac                                                  17

<210> SEQ ID NO 1433
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1433

```
cttccaccag aggg                                                    14
```

<210> SEQ ID NO 1434
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1434

```
gtcttccacc agag                                                    14
```

<210> SEQ ID NO 1435
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1435

```
cttgtcttcc accagag                                                 17
```

<210> SEQ ID NO 1436
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1436

```
tccttgtctt ccac                                                    14
```

<210> SEQ ID NO 1437
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1437

```
cttccttgtc ttccac                                                  16
```

<210> SEQ ID NO 1438
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1438

```
catcttgtga taggg                                                   15
```

<210> SEQ ID NO 1439
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1439

```
gctaggtgca gtggt                                                    15

<210> SEQ ID NO 1440
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1440
gatggctagg tgca                                                     14

<210> SEQ ID NO 1441
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1441
gtggatgatg gctag                                                    15

<210> SEQ ID NO 1442
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1442
cccgtggatg atgg                                                     14

<210> SEQ ID NO 1443
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1443
ctgcccgtgg atga                                                     14

<210> SEQ ID NO 1444
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1444
agagcctcca ccca                                                     14

<210> SEQ ID NO 1445
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1445
gttgtactct cgagc                                                    15
```

```
<210> SEQ ID NO 1446
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1446
cgttgtactc tcg                                                          13

<210> SEQ ID NO 1447
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1447
cgcgttgtac tctc                                                         14

<210> SEQ ID NO 1448
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1448
gagtctccat gccg                                                         14

<210> SEQ ID NO 1449
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1449
ctgagtctcc atgc                                                         14

<210> SEQ ID NO 1450
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1450
catggctgag tctc                                                         14

<210> SEQ ID NO 1451
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1451
tgcatggctg agtc                                                         14
```

```
<210> SEQ ID NO 1452
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1452
gcgttcacgt tggc                                                        14

<210> SEQ ID NO 1453
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1453
gtgcgagcgt tcac                                                        14

<210> SEQ ID NO 1454
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1454
aggtgcgagc gttc                                                        14

<210> SEQ ID NO 1455
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1455
gcaaaggtgc gagc                                                        14

<210> SEQ ID NO 1456
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1456
cctggtggct cagg                                                        14

<210> SEQ ID NO 1457
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1457
gtcagtcacc tgag                                                        14
```

```
<210> SEQ ID NO 1458
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1458
caggtcagtc acctg                                                        15

<210> SEQ ID NO 1459
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1459
cagcaggtca gtcac                                                        15

<210> SEQ ID NO 1460
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1460
gcagcaggtc agtc                                                         14

<210> SEQ ID NO 1461
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1461
catttagcag caaggtc                                                      17

<210> SEQ ID NO 1462
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1462
gcagcattta gcagc                                                        15

<210> SEQ ID NO 1463
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1463
ctgagcagca tttg                                                         14

<210> SEQ ID NO 1464
```

```
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1464
cccatgagaa tcct                                                     14

<210> SEQ ID NO 1465
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1465
ccttcccatg agaatcc                                                  17

<210> SEQ ID NO 1466
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1466
tcctcccctt ccca                                                     14

<210> SEQ ID NO 1467
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1467
gcctccagta gacc                                                     14

<210> SEQ ID NO 1468
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1468
gtcagacagg gcct                                                     14

<210> SEQ ID NO 1469
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1469
ccatgtcaga cagg                                                     14

<210> SEQ ID NO 1470
<211> LENGTH: 14
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1470
ggcccatgtc agac                                                         14

<210> SEQ ID NO 1471
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1471
gctattcctg aaatcac                                                      17

<210> SEQ ID NO 1472
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1472
cctcttgtct tcttacc                                                      17

<210> SEQ ID NO 1473
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1473
ggagaagaaa cctcttg                                                      17

<210> SEQ ID NO 1474
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1474
ccttgctgaa gtttctt                                                      17

<210> SEQ ID NO 1475
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1475
ccaagactcc ttgc                                                         14

<210> SEQ ID NO 1476
<211> LENGTH: 14
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 1476
ccctttcatg gagc                                                      14

<210> SEQ ID NO 1477
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1477
cctcttggtg tgac                                                      14

<210> SEQ ID NO 1478
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1478
gactaaggat gccg                                                      14

<210> SEQ ID NO 1479
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1479
gtggcaggac taagg                                                     15

<210> SEQ ID NO 1480
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1480
agacgtggca ggac                                                      14

<210> SEQ ID NO 1481
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1481
cttccagcag gcag                                                      14

<210> SEQ ID NO 1482
<211> LENGTH: 14
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 1482
gttcctctgc ctgg                                                        14

<210> SEQ ID NO 1483
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1483
gatgttcctc tgcctg                                                      16

<210> SEQ ID NO 1484
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1484
gagatgttcc tctgcc                                                      16

<210> SEQ ID NO 1485
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1485
gtgagatgtt cctctg                                                      16

<210> SEQ ID NO 1486
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1486
cagagagtga gatgttcc                                                    18

<210> SEQ ID NO 1487
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1487
ccagagagtg agatgttc                                                    18

<210> SEQ ID NO 1488
<211> LENGTH: 15
<212> TYPE: DNA
<213> ORGANISM: Artificial Sequence
<220> FEATURE:
```

-continued

<223> OTHER INFORMATION: Description of Artificial Sequence:
      antisense oligonucleotide

<400> SEQUENCE: 1488
ggtccagaga gtgag                                                     15

<210> SEQ ID NO 1489
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1489
gaggtccaga gagtg                                                     15

<210> SEQ ID NO 1490
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1490
ggtcctgtag tgcc                                                      14

<210> SEQ ID NO 1491
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1491
gattttatga tgcaggc                                                   17

<210> SEQ ID NO 1492
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1492
gacctgcatc ccttattg                                                  18

<210> SEQ ID NO 1493
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1493
tagttgattt tccagcag                                                  18

<210> SEQ ID NO 1494
<211> LENGTH: 16
<212> TYPE: DNA
<213> ORGANISM: Artificial Sequence
<220> FEATURE:
<223> OTHER INFORMATION: Description of Artificial Sequence:

antisense oligonucleotide

<400> SEQUENCE: 1494
gaatctcacg ttttgc                                                    16

<210> SEQ ID NO 1495
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1495
cagagaaaga atctcacg                                                  18

<210> SEQ ID NO 1496
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1496
tttcaccatc agagaaag                                                  18

<210> SEQ ID NO 1497
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1497
catttggaca tttcacc                                                   17

<210> SEQ ID NO 1498
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1498
ccttcatttg gacatttc                                                  18

<210> SEQ ID NO 1499
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1499
caatgtgctt gatgatcc                                                  18

<210> SEQ ID NO 1500
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide -continued

```
<400> SEQUENCE: 1500
cgcatcggat ttctc                                                    15

<210> SEQ ID NO 1501
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1501
caaaccgcat cggatttc                                                 18

<210> SEQ ID NO 1502
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1502
gaactgcaaa ccgc                                                     14

<210> SEQ ID NO 1503
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1503
gcagagaaga actgc                                                    15

<210> SEQ ID NO 1504
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1504
gcaagtaaac atggg                                                    15

<210> SEQ ID NO 1505
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1505
ggtccacgtt ttgg                                                     14

<210> SEQ ID NO 1506
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide
```

```
<400> SEQUENCE: 1506
gcaagggtcc acgttt                                                  16

<210> SEQ ID NO 1507
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1507
tggcttcttc ttcaggg                                                 17

<210> SEQ ID NO 1508
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1508
tcctgctggc ttcttc                                                  16

<210> SEQ ID NO 1509
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1509
gtcctgctgg cttc                                                    14

<210> SEQ ID NO 1510
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1510
ggtagtctag gaattgg                                                 17

<210> SEQ ID NO 1511
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1511
cttgcaggta gtctagg                                                 17

<210> SEQ ID NO 1512
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1512
```

```
gaaactcttg caggtag                                               17

<210> SEQ ID NO 1513
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1513
caccaagaaa ctcttgc                                               17

<210> SEQ ID NO 1514
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1514
cattacacca agaaactc                                              18

<210> SEQ ID NO 1515
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1515
ctcggtgttc attacacc                                              18

<210> SEQ ID NO 1516
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1516
ctttctatta tccactcg                                              18

<210> SEQ ID NO 1517
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1517
ccagtttagt ctcaactt                                              18

<210> SEQ ID NO 1518
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1518
```
aaccagttta gtctcaac                                                    18

<210> SEQ ID NO 1519
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1519
acaaaccagt ttagtctc                                                    18

<210> SEQ ID NO 1520
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1520
ctcgcgaaaa agtttctt                                                    18

<210> SEQ ID NO 1521
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1521
ccctcgcgaa aaagtttc                                                    18

<210> SEQ ID NO 1522
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1522
gtccctcgcg aaaaag                                                      16

<210> SEQ ID NO 1523
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1523
cagttgaacc gtccc                                                       15

<210> SEQ ID NO 1524
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1524
gctttcgaag tttcagtt                                                    18

```
<210> SEQ ID NO 1525
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1525
gatgctttcg aagtttc                                                      17

<210> SEQ ID NO 1526
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1526
ctgtctctgc aaataatg                                                     18

<210> SEQ ID NO 1527
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1527
cacttattac attcaccc                                                     18

<210> SEQ ID NO 1528
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1528
ttttcctcca gttcctc                                                      17

<210> SEQ ID NO 1529
<211> LENGTH: 20
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1529
ggacaatatg tacaaaactc                                                   20

<210> SEQ ID NO 1530
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1530
gttgatgaac atttggac                                                     18
```

```
<210> SEQ ID NO 1531
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1531
gtgttgatga acatttgg                                                 18

<210> SEQ ID NO 1532
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1532
caaaatttgg ccaggg                                                   16

<210> SEQ ID NO 1533
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1533
gcccaaaatt tggcc                                                    15

<210> SEQ ID NO 1534
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1534
cccagcccaa aatttgg                                                  17

<210> SEQ ID NO 1535
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1535
gtccccagcc caaaatt                                                  17

<210> SEQ ID NO 1536
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1536
aaatcgccag aggctg                                                   16
```

```
<210> SEQ ID NO 1537
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1537
accaaatcgc cagagg                                                       16

<210> SEQ ID NO 1538
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1538
catcaccaaa tcgccag                                                      17

<210> SEQ ID NO 1539
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1539
taggagtggt tgaggc                                                       16

<210> SEQ ID NO 1540
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1540
gtgtaggagt ggttgag                                                      17

<210> SEQ ID NO 1541
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1541
ctgtgtagga gtgg                                                         14

<210> SEQ ID NO 1542
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1542
cccacatgcc tgtg                                                         14

<210> SEQ ID NO 1543
```

```
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1543
cgatgaacaa cgag                                                        14

<210> SEQ ID NO 1544
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1544
ctggcgatga acaacg                                                      16

<210> SEQ ID NO 1545
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1545
cgctggcgat gaac                                                        14

<210> SEQ ID NO 1546
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1546
gagctagtcc cgttg                                                       15

<210> SEQ ID NO 1547
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1547
gcgaagagct agtcc                                                       15

<210> SEQ ID NO 1548
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1548
ccagttatgc gaagagc                                                     17

<210> SEQ ID NO 1549
<211> LENGTH: 16
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1549
ccccagttat gcgaag                                                        16

<210> SEQ ID NO 1550
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1550
cacatgcttg gcgc                                                          14

<210> SEQ ID NO 1551
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1551
gatcacatgc ttggcg                                                        16

<210> SEQ ID NO 1552
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1552
gacaaagagc atgatcac                                                      18

<210> SEQ ID NO 1553
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1553
gagtcacagg gacaaag                                                       17

<210> SEQ ID NO 1554
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1554
gagagtcaca gggac                                                         15

<210> SEQ ID NO 1555
<211> LENGTH: 15
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 1555
gcagagagtc acagg                                                      15

<210> SEQ ID NO 1556
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1556
ccatgcagag agtc                                                       14

<210> SEQ ID NO 1557
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1557
ccaccatgca gagag                                                      15

<210> SEQ ID NO 1558
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1558
tagccacgac cacc                                                       14

<210> SEQ ID NO 1559
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1559
gattagctgc ccatcctt                                                   18

<210> SEQ ID NO 1560
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1560
ggtatagatt agctgcc                                                    17

<210> SEQ ID NO 1561
<211> LENGTH: 18
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 1561
gtatcttctg tgaatggg                                                 18

<210> SEQ ID NO 1562
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1562
ctggcccaca gtct                                                     14

<210> SEQ ID NO 1563
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1563
ctctggccca cagt                                                     14

<210> SEQ ID NO 1564
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1564
tgcagggctc tctg                                                     14

<210> SEQ ID NO 1565
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1565
agtgcagggc tctc                                                     14

<210> SEQ ID NO 1566
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1566
cactgatcat gatggc                                                   16

<210> SEQ ID NO 1567
<211> LENGTH: 18
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 1567
gacactgatc atgatggc                                              18

<210> SEQ ID NO 1568
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1568
acaatgacac tgatcatg                                              18

<210> SEQ ID NO 1569
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1569
gaaccaccag gaggat                                                16

<210> SEQ ID NO 1570
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1570
gacacaaaac agccact                                               17

<210> SEQ ID NO 1571
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1571
gtggaccttt cggac                                                 15

<210> SEQ ID NO 1572
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1572
caaccagcat acgaagt                                               17

<210> SEQ ID NO 1573
<211> LENGTH: 14
<212> TYPE: DNA
<213> ORGANISM: Artificial Sequence
<220> FEATURE:
<223> OTHER INFORMATION: Description of Artificial Sequence:
``` antisense oligonucleotide

<400> SEQUENCE: 1573
tccctctggg cttc                                                        14

<210> SEQ ID NO 1574
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1574
actgtccctc tggg                                                        14

<210> SEQ ID NO 1575
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1575
gactgtccct ctgg                                                        14

<210> SEQ ID NO 1576
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1576
cctagatgac tgtccc                                                      16

<210> SEQ ID NO 1577
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1577
cagcgaggat actgc                                                       15

<210> SEQ ID NO 1578
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1578
cttcaccagc gaggat                                                      16

<210> SEQ ID NO 1579
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

```
<400> SEQUENCE: 1579
tttcctctgg gtcttcac                                           18

<210> SEQ ID NO 1580
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1580
ctttcctctg ggtcttc                                            17

<210> SEQ ID NO 1581
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1581
ctcccaatcc aagtttt                                            17

<210> SEQ ID NO 1582
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1582
ttcatcccgg agcc                                               14

<210> SEQ ID NO 1583
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1583
ttcttcatcc cggagc                                             16

<210> SEQ ID NO 1584
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1584
gctcagccag ttcttc                                             16

<210> SEQ ID NO 1585
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide
```

```
<400> SEQUENCE: 1585
gacagagagg gcac                                                     14

<210> SEQ ID NO 1586
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1586
cttcacctcc gacag                                                    15

<210> SEQ ID NO 1587
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1587
gaaaagtctg ggcagg                                                   16

<210> SEQ ID NO 1588
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1588
gaccctggaa cagaaaag                                                 18

<210> SEQ ID NO 1589
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1589
ctgaccctgg aacag                                                    15

<210> SEQ ID NO 1590
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1590
actacaggct gaccct                                                   16

<210> SEQ ID NO 1591
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1591
```

-continued attcactaca ggctgacc                                              18

<210> SEQ ID NO 1592
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1592
cgattcacta cagg                                                  14

<210> SEQ ID NO 1593
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1593
ggccgattca ctac                                                  14

<210> SEQ ID NO 1594
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1594
cgaacgtctg ttggtc                                                16

<210> SEQ ID NO 1595
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1595
cgcgaacgtc tgttg                                                 15

<210> SEQ ID NO 1596
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1596
cttctgtttg tcgaggat                                              18

<210> SEQ ID NO 1597
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1597

```
ttcaccacct tctgtttg                                                    18
```

<210> SEQ ID NO 1598
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1598

```
aggatgcgct tttcattc                                                    18
```

<210> SEQ ID NO 1599
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1599

```
agcttgcagg atgcg                                                       15
```

<210> SEQ ID NO 1600
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1600

```
gttgacagct tgcaggat                                                    18
```

<210> SEQ ID NO 1601
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1601

```
ggaacggaaa gttgacag                                                    18
```

<210> SEQ ID NO 1602
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1602

```
aactcgagtt tgacgagg                                                    18
```

<210> SEQ ID NO 1603
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1603

```
tgtccttgaa ggagaac                                                     17
```

```
<210> SEQ ID NO 1604
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1604
cgtactccat gaccatgt                                                 18

<210> SEQ ID NO 1605
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1605
gcacgtactc catgac                                                   16

<210> SEQ ID NO 1606
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1606
gattctccgg cttcag                                                   16

<210> SEQ ID NO 1607
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1607
tcaatgagca gattctcc                                                 18

<210> SEQ ID NO 1608
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1608
ggtcaatgag cagattc                                                  17

<210> SEQ ID NO 1609
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1609
ccctgctggt caatg                                                    15
```

```
<210> SEQ ID NO 1610
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1610
tagccctgct ggtc                                              14

<210> SEQ ID NO 1611
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1611
cgcttggcga aacc                                              14

<210> SEQ ID NO 1612
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1612
ccttcacgcg cttg                                              14

<210> SEQ ID NO 1613
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1613
aaggtccaag tgcg                                              14

<210> SEQ ID NO 1614
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1614
tgccgcacaa ggtc                                              14

<210> SEQ ID NO 1615
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1615
ggtgaggacc accattt                                           17
```

```
<210> SEQ ID NO 1616
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1616
gggtgtcaca ggtg                                                     14

<210> SEQ ID NO 1617
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1617
ataccatctt cttcaggg                                                 18

<210> SEQ ID NO 1618
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1618
ggtgatacca tcttcttc                                                 18

<210> SEQ ID NO 1619
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1619
ccaggtgata ccatcttc                                                 18

<210> SEQ ID NO 1620
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1620
cctcactgct ctggt                                                    15

<210> SEQ ID NO 1621
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1621
taagacctca ctgc                                                     14

<210> SEQ ID NO 1622
```

```
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1622
cagagcctaa gacctc                                                      16

<210> SEQ ID NO 1623
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1623
ccagagccta agacc                                                       15

<210> SEQ ID NO 1624
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1624
tcttcctttt tgtgaagc                                                    18

<210> SEQ ID NO 1625
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1625
gaccaaattc catcttcc                                                    18

<210> SEQ ID NO 1626
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1626
atcagtggac caaattcc                                                    18

<210> SEQ ID NO 1627
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1627
ggttctttct ggtccttt                                                    18

<210> SEQ ID NO 1628
<211> LENGTH: 18
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1628
tttttgggtt ctttctgg                                            18

<210> SEQ ID NO 1629
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1629
ggtcttattt ttgggttc                                            18

<210> SEQ ID NO 1630
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1630
aatgggcaga ctctcct                                             17

<210> SEQ ID NO 1631
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1631
tccaccatga cctcaatg                                            18

<210> SEQ ID NO 1632
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1632
aacggcatcc accatg                                              16

<210> SEQ ID NO 1633
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1633
gtgaacggca tccac                                               15

<210> SEQ ID NO 1634
<211> LENGTH: 18
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 1634
acttgagctt gtgaacgg                                              18

<210> SEQ ID NO 1635
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1635
ttcatacttg agcttgtg                                              18

<210> SEQ ID NO 1636
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1636
ctggtgtagt tttcatac                                              18

<210> SEQ ID NO 1637
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1637
agctgctggt gtagtttt                                              18

<210> SEQ ID NO 1638
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1638
aggaggacca gggt                                                  14

<210> SEQ ID NO 1639
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1639
aggtggtcca ggag                                                  14

<210> SEQ ID NO 1640
<211> LENGTH: 18
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 1640
tttctggcca aactgagg                                                   18

<210> SEQ ID NO 1641
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1641
ggaggtttct ggcc                                                       14

<210> SEQ ID NO 1642
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1642
tctggagtgg ccac                                                       14

<210> SEQ ID NO 1643
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1643
cttctggagc atgttgct                                                   18

<210> SEQ ID NO 1644
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1644
gccttctgga gcatg                                                      15

<210> SEQ ID NO 1645
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1645
gtttgtctgg ccttctg                                                    17

<210> SEQ ID NO 1646
<211> LENGTH: 18
<212> TYPE: DNA
<213> ORGANISM: Artificial Sequence
<220> FEATURE:
```

<223> OTHER INFORMATION: Description of Artificial Sequence:
      antisense oligonucleotide

<400> SEQUENCE: 1646
gagtttgtct ggccttct                                                 18

<210> SEQ ID NO 1647
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1647
ctagagtttg tctggcct                                                 18

<210> SEQ ID NO 1648
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1648
gcaagggtaa aattctag                                                 18

<210> SEQ ID NO 1649
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1649
agtgcaaggg taaaattc                                                 18

<210> SEQ ID NO 1650
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1650
aaacaggcct ccact                                                    15

<210> SEQ ID NO 1651
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1651
cttggttaat tccaatgg                                                 18

<210> SEQ ID NO 1652
<211> LENGTH: 18
<212> TYPE: DNA
<213> ORGANISM: Artificial Sequence
<220> FEATURE:
<223> OTHER INFORMATION: Description of Artificial Sequence:

antisense oligonucleotide

<400> SEQUENCE: 1652
aggcaactcc cattagtt                                           18

<210> SEQ ID NO 1653
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1653
tactactaag gcacaggg                                           18

<210> SEQ ID NO 1654
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1654
aatactacta aggcacag                                           18

<210> SEQ ID NO 1655
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1655
gtacatcttc aagtcttc                                           18

<210> SEQ ID NO 1656
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1656
ggagtggaca tgat                                               14

<210> SEQ ID NO 1657
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1657
aagaagatga agcctttg                                           18

<210> SEQ ID NO 1658
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

```
<400> SEQUENCE: 1658
ccgtcttact cttcttgg                                                 18

<210> SEQ ID NO 1659
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1659
ccgatacaat tccaagg                                                  17

<210> SEQ ID NO 1660
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1660 cctttteett ctgag                                                    15

<210> SEQ ID NO 1661
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1661
ctgttgcaag tacg                                                     14

<210> SEQ ID NO 1662
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1662
cagaagcaga gggc                                                     14

<210> SEQ ID NO 1663
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1663
cctcagaagc agagg                                                    15

<210> SEQ ID NO 1664
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide
```

```
<400> SEQUENCE: 1664
ctcctcagaa gcag                                              14

<210> SEQ ID NO 1665
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1665
acaggctggt ggca                                              14

<210> SEQ ID NO 1666
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1666
ccactctcaa acaggc                                            16

<210> SEQ ID NO 1667
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1667
acggtagccg aagc                                              14

<210> SEQ ID NO 1668
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1668
gacggtagcc gaagc                                             15

<210> SEQ ID NO 1669
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1669
ggccagacgg tagc                                              14

<210> SEQ ID NO 1670
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1670
```
gtgtagggcc agacggta                                               18

<210> SEQ ID NO 1671
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1671
ccgaagccat ttttcagg                                               18

<210> SEQ ID NO 1672
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1672
ccccgaagcc attttc                                                 17

<210> SEQ ID NO 1673
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1673
ggttgatgtc gtcc                                                   14

<210> SEQ ID NO 1674
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1674
gcttgagaca ctcgc                                                  15

<210> SEQ ID NO 1675
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1675
ccggacccgt ccat                                                   14

<210> SEQ ID NO 1676
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1676

```
gcttgcttta ctgc                                                    14

<210> SEQ ID NO 1677
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1677
ggttgctctg agac                                                    14

<210> SEQ ID NO 1678
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1678
gccacagtca tgcc                                                    14

<210> SEQ ID NO 1679
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1679
cgggcatgct ggcg                                                    14

<210> SEQ ID NO 1680
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1680
gtgaagttca ggatgatc                                                18

<210> SEQ ID NO 1681
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1681
ccagtgcctc atgg                                                    14

<210> SEQ ID NO 1682
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1682
cagtgttctc catgg                                                   15
```

```
<210> SEQ ID NO 1683
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1683
ctgtaccaga ccgag                                                        15

<210> SEQ ID NO 1684
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1684
gcatactgtt tcagc                                                        15

<210> SEQ ID NO 1685
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1685
gccatcagct ccttg                                                        15

<210> SEQ ID NO 1686
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1686
ccacaccata gatgg                                                        15

<210> SEQ ID NO 1687
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1687
gctggagcag tttcc                                                        15

<210> SEQ ID NO 1688
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1688
ctcgcttctg ctgc                                                         14
```

```
<210> SEQ ID NO 1689
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1689
accgtggcaa agcg                                                    14

<210> SEQ ID NO 1690
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1690
aggtgacacc gtgg                                                    14

<210> SEQ ID NO 1691
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1691
gacttgattc cttcag                                                  16

<210> SEQ ID NO 1692
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1692
ggatttgact tgattcc                                                 17

<210> SEQ ID NO 1693
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1693
gctgctgttc atgg                                                    14

<210> SEQ ID NO 1694
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1694
ccgtttcttt cagtagg                                                 17
```

```
<210> SEQ ID NO 1695
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1695
cttgaagtag gagc                                                     14

<210> SEQ ID NO 1696
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1696
cgctcctaca tggc                                                     14

<210> SEQ ID NO 1697
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1697
gatgaggtac aggcc                                                    15

<210> SEQ ID NO 1698
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1698
gtagatgagg tacag                                                    15

<210> SEQ ID NO 1699
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1699
gagtagatga ggtac                                                    15

<210> SEQ ID NO 1700
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1700
cctgggagta gatg                                                     14

<210> SEQ ID NO 1701
```

```
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1701
ggacctggga gtag                                                     14

<210> SEQ ID NO 1702
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1702
acatgggtgg aggg                                                     14

<210> SEQ ID NO 1703
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1703
gtgctcatgg tgtc                                                     14

<210> SEQ ID NO 1704
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1704
ctttcagtgc tcatg                                                    15

<210> SEQ ID NO 1705
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1705
tgctttcagt gctca                                                    15

<210> SEQ ID NO 1706
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1706
gatgatctga ctgcc                                                    15

<210> SEQ ID NO 1707
<211> LENGTH: 16
```

```
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1707
gttcgagaag atgatc                                                    16

<210> SEQ ID NO 1708
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1708
gggttcgaga agatg                                                     15

<210> SEQ ID NO 1709
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1709
ggtttgctac aacatg                                                    16

<210> SEQ ID NO 1710
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1710
cagcttgagg gtttg                                                     15

<210> SEQ ID NO 1711
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1711
tgcccctcag cttg                                                      14

<210> SEQ ID NO 1712
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1712
gacacacact atctc                                                     15

<210> SEQ ID NO 1713
<211> LENGTH: 16
<212> TYPE: DNA
```

```
<213> ORGANISM: Artificial Sequence
<220> FEATURE:
<223> OTHER INFORMATION: Description of Artificial Sequence:
      antisense oligonucleotide

<400> SEQUENCE: 1713
gcagccatct ttattc                                                  16

<210> SEQ ID NO 1714
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1714
gttcagcagc catc                                                    14

<210> SEQ ID NO 1715
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1715
tggttcagca gcca                                                    14

<210> SEQ ID NO 1716
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1716
ctactggttc agcagc                                                  16

<210> SEQ ID NO 1717
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1717
tctactggtt cagc                                                    14

<210> SEQ ID NO 1718
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1718
gccacaaagt tgatgc                                                  16

<210> SEQ ID NO 1719
<211> LENGTH: 16
<212> TYPE: DNA
<213> ORGANISM: Artificial Sequence
```

```
<220> FEATURE:
<223> OTHER INFORMATION: Description of Artificial Sequence:
      antisense oligonucleotide

<400> SEQUENCE: 1719
cattgccaca aagttg                                                  16

<210> SEQ ID NO 1720
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1720
gagaacttgg tcattc                                                  16

<210> SEQ ID NO 1721
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1721
ggtcaatgaa gagaac                                                  16

<210> SEQ ID NO 1722
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1722
cgatttcctt ggtc                                                    14

<210> SEQ ID NO 1723
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1723
ccgatttcct tggtc                                                   15

<210> SEQ ID NO 1724
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1724
caaatagagg ccgatttc                                                18

<210> SEQ ID NO 1725
<211> LENGTH: 14
<212> TYPE: DNA
<213> ORGANISM: Artificial Sequence
<220> FEATURE:
```

```
<223> OTHER INFORMATION: Description of Artificial Sequence:
      antisense oligonucleotide

<400> SEQUENCE: 1725
caaatagagg ccga                                                        14

<210> SEQ ID NO 1726
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1726
cctctaggct ggct                                                        14

<210> SEQ ID NO 1727
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1727
catacctcta ggctg                                                       15

<210> SEQ ID NO 1728
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1728
agccatacct ctag                                                        14

<210> SEQ ID NO 1729
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1729
cagccatacc tctag                                                       15

<210> SEQ ID NO 1730
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1730
cacagagata gttacag                                                     17

<210> SEQ ID NO 1731
<211> LENGTH: 17
<212> TYPE: DNA
<213> ORGANISM: Artificial Sequence
<220> FEATURE:
<223> OTHER INFORMATION: Description of Artificial Sequence:
``` antisense oligonucleotide

<400> SEQUENCE: 1731
gtcttcgttt tgaacag                                                  17

<210> SEQ ID NO 1732
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1732
ctagtcttcg ttttgaac                                                 18

<210> SEQ ID NO 1733
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1733
tagctagtct tcgttttg                                                 18

<210> SEQ ID NO 1734
<211> LENGTH: 13
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1734
gagccactgc gcc                                                      13

<210> SEQ ID NO 1735
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1735
cgtgagccac tgcg                                                     14

<210> SEQ ID NO 1736
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1736
cgtaacgatc actgg                                                    15

<210> SEQ ID NO 1737
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

```
<400> SEQUENCE: 1737
gcactcgtaa cgatc                                                    15

<210> SEQ ID NO 1738
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1738
ggagcactcg taac                                                     14

<210> SEQ ID NO 1739
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1739
catcatcctg aggt                                                     14

<210> SEQ ID NO 1740
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1740
cagtatcatc atcctg                                                   16

<210> SEQ ID NO 1741
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1741
ctcagtatca tcatcc                                                   16

<210> SEQ ID NO 1742
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1742
ctaaaagtat gtgccatc                                                 18

<210> SEQ ID NO 1743
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide
```

```
<400> SEQUENCE: 1743
cacatcgcct ctct                                                          14

<210> SEQ ID NO 1744
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1744
gcttcacagt cacatcgc                                                      18

<210> SEQ ID NO 1745
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1745
ggaaggcttc acagtc                                                        16

<210> SEQ ID NO 1746
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1746
cctgtgactt gagaattg                                                      18

<210> SEQ ID NO 1747
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1747
ggaagacctg tgac                                                          14

<210> SEQ ID NO 1748
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1748
ctctgctcca catatttg                                                      18

<210> SEQ ID NO 1749
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1749
```
caacgaagat ctctg					15

<210> SEQ ID NO 1750
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1750
caacaccaac gaag					14

<210> SEQ ID NO 1751
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1751
ggtcttctgt ttgc					14

<210> SEQ ID NO 1752
<211> LENGTH: 18
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1752
cgatgaagtg gtaggaag					18

<210> SEQ ID NO 1753
<211> LENGTH: 14
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1753
ggttgcatgg aagc					14

<210> SEQ ID NO 1754
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1754
ggtcacaaac ttgcc					15

<210> SEQ ID NO 1755
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1755
ctgatttggt ccactag                                                17

<210> SEQ ID NO 1756
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1756
catgttagca ctgttc                                                 16

<210> SEQ ID NO 1757
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1757
ggtcttgatg tactcc                                                 16

<210> SEQ ID NO 1758
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1758
ccacctaaag agagatc                                                17

<210> SEQ ID NO 1759
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1759
cttgtactgc accatc                                                 16

<210> SEQ ID NO 1760
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1760
gccagttaag aagatg                                                 16

<210> SEQ ID NO 1761
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1761
gagatcatga tccatgg                                                17

```
<210> SEQ ID NO 1762
<211> LENGTH: 17
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1762
gtagtgtccc aatagtg                                                    17

<210> SEQ ID NO 1763
<211> LENGTH: 16
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1763
cttcctcatc attccc                                                     16

<210> SEQ ID NO 1764
<211> LENGTH: 15
<212> TYPE: DNA
<213> ORGANISM: Artificial Sequence
<220> FEATURE:
<223> OTHER INFORMATION: Description of Artificial Sequence:
      antisense oligonucleotide

<400> SEQUENCE: 1764
cacaagcttt tcgac                                                      15
```